(12) United States Patent
Sootome

(10) Patent No.: US 10,124,003 B2
(45) Date of Patent: Nov. 13, 2018

(54) THERAPEUTIC AGENT FOR FGFR INHIBITOR-RESISTANT CANCER

(71) Applicant: TAIHO PHARMACEUTICAL CO., LTD., Chiyoda-ku, Tokyo (JP)

(72) Inventor: Hiroshi Sootome, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/905,047

(22) PCT Filed: Jul. 17, 2014

(86) PCT No.: PCT/JP2014/069105
§ 371 (c)(1),
(2) Date: Jan. 14, 2016

(87) PCT Pub. No.: WO2015/008844
PCT Pub. Date: Jan. 22, 2015

(65) Prior Publication Data
US 2016/0136168 A1    May 19, 2016

(30) Foreign Application Priority Data
Jul. 18, 2013    (JP) .................................. 2013-149958

(51) Int. Cl.
| | | |
|---|---|---|
| A61K 31/519 | (2006.01) | |
| A61K 31/437 | (2006.01) | |
| A61K 31/404 | (2006.01) | |
| A61K 31/44 | (2006.01) | |
| A61K 31/47 | (2006.01) | |
| A61K 31/496 | (2006.01) | |
| A61K 31/5025 | (2006.01) | |
| A61K 31/506 | (2006.01) | |
| A61K 31/53 | (2006.01) | |
| A61K 31/5377 | (2006.01) | |

(52) U.S. Cl.
CPC .......... *A61K 31/519* (2013.01); *A61K 31/404* (2013.01); *A61K 31/437* (2013.01); *A61K 31/44* (2013.01); *A61K 31/47* (2013.01); *A61K 31/496* (2013.01); *A61K 31/506* (2013.01); *A61K 31/5025* (2013.01); *A61K 31/53* (2013.01); *A61K 31/5377* (2013.01)

(58) Field of Classification Search
None
See application file for complete search history.

(56) References Cited

U.S. PATENT DOCUMENTS

| | | |
|---|---|---|
| 2009/0318468 A1 | 12/2009 | Buttar et al. |
| 2011/0275084 A1* | 11/2011 | Byron ............... C07K 14/70503 435/6.12 |
| 2012/0101064 A1 | 4/2012 | Howard et al. |
| 2013/0061403 A1 | 3/2013 | Bringewatt et al. |
| 2014/0005185 A1 | 1/2014 | Nakamura et al. |
| 2014/0343035 A1* | 11/2014 | Sagara ................ C07D 487/04 514/210.18 |
| 2015/0166544 A1 | 6/2015 | Zhang et al. |
| 2016/0136168 A1 | 5/2016 | Sootome |
| 2016/0193210 A1 | 7/2016 | Ochiiwa et al. |
| 2016/0250287 A1 | 9/2016 | Yauch et al. |
| 2017/0035773 A1 | 2/2017 | Tomimatsu et al. |

(Continued)

FOREIGN PATENT DOCUMENTS

| | | |
|---|---|---|
| EA | 201101566 A1 | 5/2012 |
| EP | 3279202 A1 | 2/2018 |
| JP | 2011-524888 A | 9/2011 |

(Continued)

OTHER PUBLICATIONS

Konecny et al. In Molecular Cancer Therapeutics 12(5); 632-642 (2013).*

(Continued)

*Primary Examiner* — Dennis Heyer

(74) *Attorney, Agent, or Firm* — Rothwell, Figg, Ernst & Manbeck, P.C.

(57) ABSTRACT

The problem to be solved by the present invention is to provide an anticancer agent for treating tumors resistant to other antitumor agents that inhibit FGFR, and a method for treating such tumors. The present invention provides an antitumor agent for administration to a tumor patient resistant to an FGFR inhibitor, the antitumor agent comprising a 3,5-disubstituted benzene alkynyl compound represented by Formula (I) below or a salt thereof. The present invention also provides a therapeutic method using the anticancer agent.

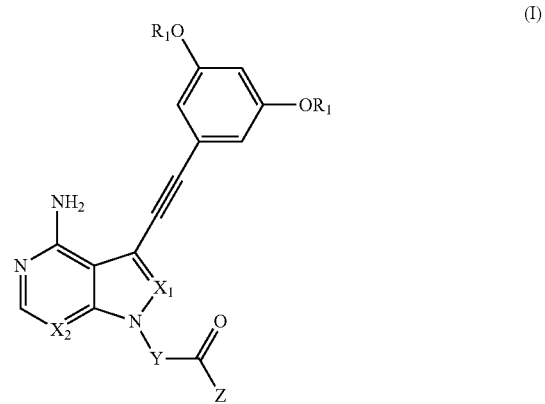

(I)

8 Claims, 1 Drawing Sheet

Specification includes a Sequence Listing.

(56) References Cited

U.S. PATENT DOCUMENTS

2017/0252317 A1  9/2017  Lyssikatos et al.

FOREIGN PATENT DOCUMENTS

| | | |
|---|---|---|
| JP | 2013-523428 A | 6/2013 |
| JP | 2015/008844 A1 | 1/2015 |
| JP | 2015-527336 A | 9/2015 |
| JP | 2016-104762 A | 6/2016 |
| RU | 20098127883 A | 7/2009 |
| RU | 2428421 C2 | 12/2009 |
| WO | 2007/041712 A1 | 4/2007 |
| WO | 2007/087395 A2 | 8/2007 |
| WO | 2008077557 A1 | 7/2008 |
| WO | 2008/121742 A2 | 10/2008 |
| WO | 2010/043865 A1 | 4/2010 |
| WO | 2011/093672 A2 | 8/2011 |
| WO | 2011/115937 A1 | 9/2011 |
| WO | 2011/153514 A2 | 12/2011 |
| WO | 2012/137870 A1 | 10/2012 |
| WO | 2013/108809 A1 | 7/2013 |
| WO | WO 2013/108809 * | 7/2013 |
| WO | WO2013/108809 * | 7/2013 |
| WO | 2014/138364 A2 | 9/2014 |
| WO | 2014/172644 A2 | 10/2014 |
| WO | 2015/008839 A1 | 1/2015 |
| WO | 2015/008844 A1 | 1/2015 |
| WO | 2016/159327 A1 | 10/2016 |
| WO | 2017/150725 A1 | 9/2017 |

OTHER PUBLICATIONS

Gangjee et al., "Synthesis of 5,7-disubstituted-4-methyl-7H-pyrrolo[2,3-d]pyrimidin-2-amines as microtubule inhibitors", Bioorganic Medical Chemistry, 2013, vol. 21, No. 5, pp. 1180-1189.
Nakatsuru et al., "Significant in vivo Antitumor Activity by a Highly Potent, irreversible FGFR inhibitor, TAS-2985", European Journal of Cancer, vol. 48, Suppl.6, p. 117, 383.
Hernandez et al., "Prospective Study of FGFR3 Mutations as a Prognostic Factor in Nonmuscle invasive Urothelial Bladder Carcinomas", Journal of Clinical Oncology, 2006, vol. 24, No. 22, pp. 3664-3671.
Gelsi-Boyer et al., "Comprehensive Profiling of 8p11-12 Amplification in Breast Cancer", Molecular Cancer Research, 2005, vol. 3, No. 12, pp. 655-667.
Turner et al., "FGFR1 Amplification Drives Endocrine Therapy Resistance and is a Therapeutic Target in Breast cancer", Cancer Research, 2010, vol. 70, No. 5, pp. 2085-2094.
Lieu et al., "Beyond VEGF: Inhibition of the Fibroblast Growth Factor Pathway and Antiangiogenesis", Clinical Cancer Research, 2011, vol. 17, No. 19, pp. 6130-6139.
Folkman, Angiogenesis in cancer, vascular, rheumatoid and other disease, Nature Medicine, 1995, vol. 1, No. 1, pp. 27-31.
International Search Report cited in PCT/JP2014/069105 dated Sep. 2, 2014, 4 pages.
Notification of Reasons for Refusal for the corresponding JP patent application No. 2015-527336 (with machine translation) Oct. 3, 2016, 7 pgs.
Office Action for the corresponding RU patent application No. 2016105133, dated Feb. 27, 2018.
Sootome et al., "Identification and Biological Characterization of a Highly Potent, Irreversible Inhibitor of FGFR, TAS-2985", European Journal of Cancer, 48:116, 2012.
Fukumoto et al., "FGF23 is a hormone-regulating phosphate metabolism—Unique biological characteristics of FGF23", Bone, 2007, vol. 40, pp. 1190-1195.
Gong et al., "A novel 3-arylethynyl-substituted pyrido[2,3-b]pyrazine derivatives and pharmacophore model as Wnt2/3-catenin pathway inhibitors in a non-small-cell lung cancer cell lines", Bioorganic &Medicinal Chemistry, vol. 19, 2011, pp. 5639-5647.
Yuki Kagobutsu Kessho Sakusei Handbook—Genri to Know-how-, Maruzen Co., Ltd., 2008, pp. 57-84 (See RU Office Action for a concise explanation).
Office Action for the JP patent application No. 2016-566309, dated Feb. 2, 2017.
Byrn et al., "Pharmaceutical Solids: A Strategic Approach to Regulatory Considerations", Pharmaceutical Research, 1995, 12(7), pp. 945-954.
Keiko Toyo Seizai no Sekkei to Hyoka, Kabushiki Kaisha Yakugyo Jihosha, 1995, pp. 76-79, 171-172 (See RU Office Action for a concise explanation).
Wilson et al., "Widespread potential for growth-factor-driven resistance to anticancer kinase inhibitors", Nature, 2012, 487(7408): 505-509.
Xie et al., "FGFR2 Gene Amplification in Gastric Cancer Predicts Sensitivity to the Selective FGFR Inhibitor AZD4547", Clinical Cancer Research, 2013, vol. 19, No. 9 pp. 2572-2583.
Chang et al., "Multiple receptor tyrosine kinase activation attenuates therapeutic efficacy of the fibroblast growth factor receptor 2 inhibitor AZD4547 in FGFR2 amplified gastric cancer", Oncotarget, vol. 6, No. 4, 2014, pp. 2009-2022.
Kleespies et al., "Tyrosine kinase inhibitors and gemcitabine: New treatment options in pancreatic cancer?", Drug Resistance Updates, (9) 2006, pp. 1-18.
Byron et al., "Fibroblast growth factor receptor inhibition synergizes with paclitaxel and doxorubicin in endometrial cancer cells", International Journal of Gynecological Cancer, 2012, vol. 22, No. 9, pp. 1517-1526.
Bavin, "Polymorphism in Process Development", Chemistry & Industry, 1989, (16), pp. 527-529.
Shimada et al., Targeted ablation of Fgf23 demonstrates an essential physiological role of FGF23 in phosphate and vitamin D metabolism, Journal of Clinical Investigation, 2004, vol. 113, No. 4, pp. 561-568.
Razzaque et al., "FGF-23, vitamin D and calcification: the unholy triad", Nephrol. Dial. Transplant, 2005, vol. 20, pp. 2032-2035.
Decision of Refusal for the corresponding JP patent application No. 2017-149671, dated May 2018.
Lectures of Experimental Chemistry (continued) 2 Separation and purification, 1967, pp. 159-162, 184-193.
Handbook of Solvents, 1985, pp. 47-51.
Version 4 Lectures on experimental chemistry 1 Basic operation I, 1990, pp. 184-189.
Impurities: Guideline for Residual Solvents, 1998, No. 307, pp. 1-11.
Office Action dated Apr. 24, 2017 for the corresponding RU patent application No. 2017134584, 15 pages.

* cited by examiner

```
  1 mvswgrficl vvvtmatlsl arpsfslved ttlepeeppt kyqisqpevy vaapgeslev
 61 rcllkdaavi swtkdgvhlg pnnrtvlige ylqikgatpr dsglyactas rtvdsetwyf
121 mvnvtdaiss gddeddtdga edfvsensnn krapywtnte kmekrlhavp aantvkfrcp
181 aggnpmptmr wlkngkefkq ehriggykvr nqhwslimes vvpsdkgnyt cvveneygsi
241 nhtyhldvve rsphrpilqa glpanastvv ggdvefvckv ysdaqphiqw ikhvekngsk
301 ygpdglpylk vlkhsginss naevlalfnv teadageyic kvsnyigqan qsawltvlpk
361 qqapgrekei taspdyleia iycigvflia cmvvtvilcr mknttkkpdf ssqpavhklt
421 kriplrrqvt vsaessssmn sntplvritt rlsstadtpm lagvseyelp edpkwefprd
481 kltlgkplge gcfgqvvmae avgidkdkpk eavtvavkml kddatekdls dlvsememmk
541 migkhkniin llgactqdgp lyviveyask gnlreylrar rppgmeysyd inrvpeeqmt
601 fkdlvsctyq largmeylas qkcihrdlaa rnvlvtennv mkiadfglar dinnidyykk
661 ttngrlpvkw mapealfdrv ythqsdvwsf gvlmweiftl ggspypgipv eelfkllkeg
721 hrmdkpanct nelymmmrdc whavpsqrpt fkqlvedldr iltlttneey ldlsqpleqy
781 spsypdtrss cssgddsvfs pdpmpyepcl pqyphingsv kt
```

THERAPEUTIC AGENT FOR FGFR INHIBITOR-RESISTANT CANCER

CROSS REFERENCE TO RELATED APPLICATION

This application is a 35 U.S.C. 371 National Phase Entry Application from PCT/JP2014/069105, filed Jul. 17, 2014, which claims the benefit of Japanese Patent Application No. 2013-149958 filed on Jul. 18, 2013, the disclosure of which are incorporated by reference in their entirety.

TECHNICAL FIELD

The present invention relates to an antitumor agent comprising an FGFR inhibitor as an active ingredient.

BACKGROUND ART

Fibroblast growth factors (FGFs) are involved in the regulation of various physiological processes, such as cell proliferation, chemotaxis, and differentiation. The physiological activity of the FGFs is mediated by fibroblast growth factor receptors (FGFRs), which are specific cell surface receptors. FGFRs belong to a receptor protein tyrosine kinase family, and comprise an extracellular ligand-binding domain, a single transmembrane domain, and an intracellular tyrosine kinase domain. Four types of FGFRs (FGFR1, FGFR2, FGFR3, and FGFR4) have been heretofore identified. FGFRs bind to FGFs to form dimers, and are activated by phosphorylation. Activation of the receptors induces dimerization and activation of specific downstream signal transduction molecules, thereby developing physiological functions.

Many reports have been made about the relationship between aberrant FGF/FGFR signaling and various human cancers (e.g., NPL 1, NPL 2, and NPL 3). Aberrant activation of FGF/FGFR signaling in human cancer is considered to be attributable to overexpression of FGFRs and/or gene amplification, gene mutation, chromosomal translocation, or an autocrine or paracrine mechanism by overproduction of FGFs (ligands). Moreover, such aberrant signaling is considered to be partly responsible for therapeutic resistance to existing chemotherapeutic anticancer drugs or other receptor tyrosine kinase inhibitors in human cancer (NPL 4). Furthermore, the aberrant signaling is known to be associated with various diseases caused by abnormal angiogenic processes, such as solid tumor, rheumatoid arthritis, psoriasis, retinopathy, and age-related macular degeneration (NPL 5).

Accordingly, therapies targeted for FGF/FGFR signaling not only have a direct antitumor effect on tumor cells that are highly dependent on FGF/FGFR signaling, but also exhibit an inhibitory effect on tumor angiogenesis induced by FGF/FGFR signaling; thus, such therapies are expected to be promising targeted therapies having sufficient antitumor effects. In addition, such therapies are expected to provide drug effect enhancers for existing chemotherapeutic anticancer drugs or other receptor tyrosine kinase inhibitors, or effective therapeutic remedies for cancer types that are resistant or unresponsive to these drugs.

PTL 1 discloses a wide range of fused bicyclic compounds having mTOR inhibitory activity; however, the specifically disclosed compounds are all imidazopyrazine compounds, and FGFR inhibitory activity is nowhere mentioned in PTL 1. PTL 2 discloses BTK inhibitor compounds having a characteristic substituent at the 3-position of the pyrazolopyrimidine ring, but is silent about FGFR inhibitory activity. PTL 3 discloses HSP90 inhibitor compounds having a characteristic substituent at the 5-position of the pyrrolopyrimidine ring, but is silent about FGFR inhibitory activity.

Further, in the treatment of a tumor using an FGFR inhibitor, the tumor becomes resistant to the inhibitor due to FGFR mutations, which may adversely affect the prognosis of the tumor patient (PTL 4).

CITATION LIST

Patent Literature

PTL 1: WO 2007/087395
PTL 2: WO 2008/121742
PTL 3: WO 2010/043865
PTL 4: WO 2011/115937

Non-Patent Literature

NPL 1: J. Clin. Oncol. 24, 3664-3671 (2006)
NPL 2: Mol. Cancer Res. 3, 655-667 (2005)
NPL 3: Cancer Res. 70, 2085-2094 (2010)
NPL 4: Clin. Cancer Res. 17, 6130-6139 (2011)
NPL 5: Nat. Med. 1, 27-31 (1995)

SUMMARY OF INVENTION

Technical Problem

The problem to be solved by the present invention is to provide an anticancer agent for treating tumors resistant to other antitumor agents that inhibit FGFR, and a method for treating such tumors.

Solution to Problem

The present inventors further conducted various studies on methods for treating tumors resistant to conventional FGFR inhibitors, and consequently found that a 3,5-disubstituted benzene alkynyl compound or a salt thereof exhibits antitumor effects, and is very effective as a method for treating such tumors. The present invention is based on this novel finding.

Therefore, the present invention provides the following items:

Item 1. An antitumor agent for administration to a tumor patient resistant to an FGFR inhibitor, the antitumor agent comprising a 3,5-disubstituted benzene alkynyl compound represented by Formula (I):

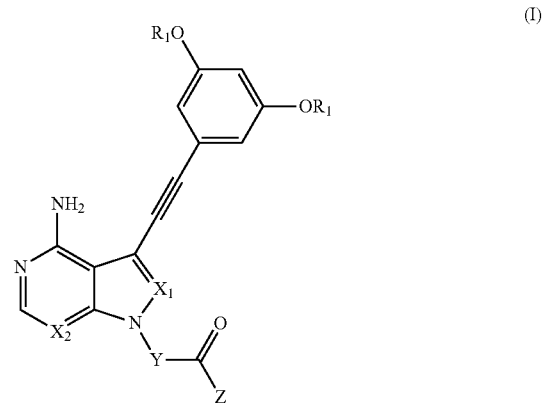

or a salt thereof, wherein $R_1$ is the same or different, and each represents $C_1$-$C_6$ alkyl;
$X_1$ and $X_2$ independently represent N or CH;
Y is a group represented by Formula (A):

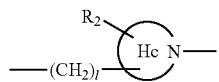
(A)

wherein the divalent moiety represented by

is a nitrogen-containing $C_3$-$C_{10}$ heterocycloalkylene group, a group represented by Formula (B):

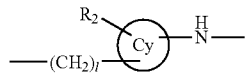
(B)

wherein the divalent moiety represented by

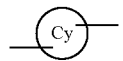

is a $C_3$-$C_{10}$ cycloalkylene group, or
a group represented by Formula (C):

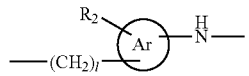
(C)

wherein the divalent moiety represented by

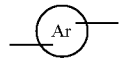

is a $C_6$-$C_{12}$ arylene group;
$R_2$ is hydrogen, $C_2$-$C_6$ alkynyl, —C(=O)O$R_x$, —C(=O)N($R_x$)($R_y$), hydroxy-$C_1$-$C_6$ alkyl, di($C_1$-$C_6$ alkyl)amino-$C_1$-$C_6$ alkyl, or $C_2$-$C_9$ heteroaryl optionally having $R_3$; and
$R_3$ is $C_1$-$C_6$ alkyl or di($C_1$-$C_6$ alkyl)amino-$C_1$-$C_6$ alkyl;
Z is —C($R_4$)=C($R_5$)($R_6$) or —C≡C—$R_7$;
$R_4$, $R_5$, and $R_6$ are the same or different, and each represents hydrogen, halogen, $C_1$-$C_6$ alkyl optionally having $R_8$, or a group represented by Formula (D):

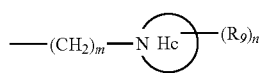
(D)

wherein the monovalent moiety represented by

is a nitrogen-containing $C_3$-$C_{10}$ heterocycloalkyl group,
$R_7$ is hydrogen, $C_1$-$C_6$ alkyl, or hydroxy-$C_1$-$C_6$ alkyl;
$R_8$ is —OR$_x$ or —N($R_x$)($R_y$);
$R_9$ is $C_1$-$C_6$ alkyl, halogen, or —OR$_x$;
$R_x$ and $R_y$ are the same or different, and each represents hydrogen, $C_1$-$C_6$ alkyl, $C_3$-$C_{10}$ cycloalkyl, di($C_1$-$C_6$ alkyl)amino-$C_1$-$C_6$ alkyl, or $C_1$-$C_6$ alkoxy-$C_1$-$C_6$ alkyl;
l is an integer of 0 to 3;
m is an integer of 1 to 3; and
n is an integer of 0 to 2.

Item 2. A method for treating a tumor patient resistant to an FGFR inhibitor, the method comprising administering an antitumor agent comprising a 3,5-disubstituted benzene alkynyl compound represented by Formula (I) above, wherein $R_1$, $X_1$, $X_2$, Y, and Z are as defined above, or a salt thereof.

Item 3. A 3,5-disubstituted benzene alkynyl compound represented by Formula (I) above, wherein $R_1$, $X_1$, $X_2$, Y, and Z are as defined above, or a salt thereof for treatment of a tumor patient resistant to an FGFR inhibitor.

Item 4. Use of a 3,5-disubstituted benzene alkynyl compound represented by Formula (I) above, wherein $R_1$, $X_1$, $X_2$, Y, and Z are as defined above, or a salt thereof for producing an antitumor agent for administration to a tumor patient resistant to an FGFR inhibitor.

Item 5. The antitumor agent according to item 1, the method according to item 2, the compound or a salt thereof according to item 3, or the use according to item 4, wherein in Formula (I), (1) when $X_2$ is N, $X_1$ is N or CH, and (2) when $X_2$ is CH, $X_1$ is CH.

Item 6. The antitumor agent, method, compound or a salt thereof, or use according to any one of items 1 to 5, wherein in Formula (I), l is 0 or 1.

Item 7. The antitumor agent, method, compound or a salt thereof, or use according to any one of items 1 to 6, wherein in Formula (I), (1) when Y is a group represented by Formula (A), the group represented by

is azetidinylene, pyrrolidinylene, piperidinylene, piperazinylene, or morpholinylene, (2) when Y is a group represented by Formula (B), the group represented by

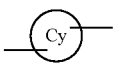

is cyclopropylene or cyclobutylene, and (3) when Y is a group represented by Formula (C), the group represented by

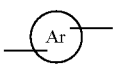

is phenylene.

Item 8. The antitumor agent, method, compound or a salt thereof, or use according to any one of items 1 to 7, wherein in Formula (I), (1) when Y is a group represented by Formula (A), Z is —C(R$_4$)=C(R$_5$)(R$_6$) or —C≡C—R$_7$, and (2) when Y is a group represented by Formula (B) or (C), Z is —C(R$_4$)=C(R$_5$)(R$_6$).

Item 9. The antitumor agent, method, compound or a salt thereof, or use according to any one of items 1 to 8, wherein in Formula (I), R$_1$ is methyl or ethyl.

Item 10. The antitumor agent, method, compound or a salt thereof, or use according to any one of items 1 to 9, wherein in Formula (I), when X$_2$ is N, X$_1$ is N or CH, and (2) when X$_2$ is CH, X$_1$ is CH; l is 0 or 1; and (1) when Y is a group represented by Formula (A), the group represented by

is azetidinylene, pyrrolidinylene, piperidinylene, piperazinylene, or morpholinylene, (2) when Y is a group represented by Formula (B), the group represented by

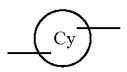

is cyclopropylene or cyclobutylene, and (3) when Y is a group represented by Formula (C), the group represented by

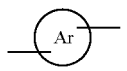

is phenylene.

Item 11. The antitumor agent, method, compound or a salt thereof, or use according to any one of items 1 to 8, wherein the 3,5-disubstituted benzene alkynyl compound is selected from the following group of compounds:

(1) (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one,
(2) (S)-1-(3-(4-amino-3-((3,5-dimethoxyphenyl)ethynyl)-1H-pyrazolo[3,4-d]pyrimidin-1-yl)pyrrolidin-1-yl)prop-2-yn-1-one,
(3) (S)-1-(3-(4-amino-3-((3,5-diethoxyphenyl)ethynyl)-1H-pyrazolo[3,4-d]pyrimidin-1-yl)pyrrolidin-1-yl)prop-2-en-1-one,
(4) 1-(3-(4-amino-3-((3,5-dimethoxyphenyl)ethynyl)-1H-pyrazolo[3,4-d]pyrimidin-1-yl)azetidin-1-yl)prop-2-en-1-one,
(5) 1-(3-(4-amino-3-((3,5-dimethoxyphenyl)ethynyl)-1H-pyrazolo[3,4-d]pyrimidin-1-yl)-4-hydroxybut-2-yn-1-one,
(6) 1-(3-(4-amino-3-((3,5-dimethoxyphenyl)ethynyl)-1H-pyrazolo[3,4-d]pyrimidin-1-yl)azetidin-1-yl)-4-(dimethylamino)but-2-en-1-one,
(7) 1-(3-(4-amino-3-((3,5-dimethoxyphenyl)ethynyl)-1H-pyrazolo[3,4-d]pyrimidin-1-yl)azetidin-1-yl)-4-(cyclopropylamino)but-2-en-1-one,
(8) 1-(3-(4-amino-3-((3, 5-dimethoxyphenyl)ethynyl)-1H-pyrazolo[3,4-d]pyrimidin-1-yl)azetidin-1-yl)-4-(isopropylamino)but-2-en-1-one,
(9) 1-(3-(4-amino-3-((3,5-dimethoxyphenyl)ethynyl)-1H-pyrazolo[3,4-d]pyrimidin-1-yl)azetidin-1-yl)-4-(ethyl(methyl)amino)but-2-en-1-one,
(10) 1-(3-(4-amino-3-((3,5-dimethoxyphenyl)ethynyl)-1H-pyrazolo[3,4-d]pyrimidin-1-yl)azetidin-1-yl)-4-(cyclobutylamino) but-2-en-1-one,
(11) 1-(3-(4-amino-3-((3,5-dimethoxyphenyl)ethynyl)-1H-pyrazolo[3,4-d]pyrimidin-1-yl)azetidin-1-yl)-4-(diethylamino)but-2-en-1-one,
(12) 1-(3-(4-amino-3-((3, 5-dimethoxyphenyl)ethynyl)-1H-pyrazolo[3,4-d]pyrimidin-1-yl)azetidin-1-yl)-4-(tert-butylamino)but-2-en-1-one,
(13) 1-(3-(4-amino-3-((3,5-dimethoxyphenyl)ethynyl)-1H-pyrazolo[3,4-d]pyrimidin-1-yl)azetidin-1-yl)-4-(isopropyl(methyl)amino)but-2-en-1-one,
(14) 1-(3-(4-amino-3-((3,5-dimethoxyphenyl)ethynyl)-1H-pyrazolo[3,4-d]pyrimidin-1-yl)azetidin-1-yl)-4-(piperidin-1-yl)but-2-en-1-one,
(15) (S)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one,
(16) (R)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one,
(17) 1-((2S,4S)-4-(4-amino-3-((3,5-dimethoxyphenyl)ethynyl)-1H-pyrazolo[3,4-d]pyrimidin-1-yl)-2-(hydroxymethyl)pyrrolidin-1-yl)prop-2-en-1-one,
(18) 1-(2S,4S)-4-(4-amino-3-((3,5-dimethoxyphenyl)ethynyl)-1H-pyrazolo[3,4-d]pyrimidin-1-yl)-2-ethynylpyrrolidin-1-yl)prop-2-en-1-one,
(19) (S)-1-(3-(4-amino-5-((3,5-dimethoxyphenyl)ethynyl)-7H-pyrrolo[2,3-d]pyrimidin-7-yl)pyrrolidin-1-yl)-4-(dimethylamino)but-2-en-1-one,
(20) (S)-1-(3-(4-amino-5-((3,5-dimethoxyphenyl)ethynyl)-7H-pyrrolo[2,3-d]pyrimidin-7-yl)pyrrolidin-1-yl)prop-2-en-1-one,
(21) (S)-1-(3-(4-amino-5-((3,5-dimethoxyphenyl)ethynyl)-7H-pyrrolo[2,3-d]pyrimidin-7-yl)pyrrolidin-1-yl)-4-(pyrrolidin-1-yl)but-2-en-1-one,
(22) (S)-1-(3-(4-amino-5-((3,5-dimethoxyphenyl)ethynyl)-7H-pyrrolo[2,3-d]pyrimidin-7-yl)pyrrolidin-1-yl)-4-(4-hydroxypiperidin-1-yl)but-2-en-1-one,
(23) (S)-1-(3-(4-amino-5-((3,5-dimethoxyphenyl)ethynyl)-7H-pyrrolo[2,3-d]pyrimidin-7-yl)pyrrolidin-1-yl)but-2-yn-1-one,
(24) (S)-1-(3-(4-amino-5-((3,5-dimethoxyphenyl)ethynyl)-7H-pyrrolo[2,3-d]pyrimidin-7-yl)pyrrolidin-1-yl)-4-hydroxy-4-methylpent-2-yn-1-one,
(25) 1-((S)-3-(4-amino-5-((3,5-dimethoxyphenyl)ethynyl)-7H-pyrrolo[2,3-d]pyrimidin-7-yl)pyrrolidin-1-yl)-4-((S)-3-fluoropyrrolidin-1-yl)but-2-en-1-one,
(26) (S)-1-(3-(4-amino-5-((3,5-dimethoxyphenyl)ethynyl)-7H-pyrrolo[2,3-d]pyrimidin-7-yl)pyrrolidin-1-yl)-4-(piperidin-1-yl)but-2-en-1-one,
(27) 1-(3-(4-amino-5-((3,5-dimethoxyphenyl)ethynyl)-7H-pyrrolo[2,3-d]pyrimidin-7-yl)azetidin-1-yl)prop-2-en-1-one,
(28) 1-(3-(4-amino-5-((3,5-dimethoxyphenyl)ethynyl)-7H-pyrrolo[2,3-d]pyrimidin-7-yl)azetidin-1-yl)-4-(dimethylamino)but-2-en-1-one,
(29) 1-(3-(4-amino-5-((3,5-dimethoxyphenyl)ethynyl)-7H-pyrrolo[2,3-d]pyrimidin-7-yl)azetidin-1-yl)-4-(pyrrolidin-1-yl)but-2-en-1-one,
(30) 1-(3-(4-amino-5-((3,5-dimethoxyphenyl)ethynyl)-7H-pyrrolo[2,3-d]pyrimidin-7-yl)azetidin-1-yl)-4-(azetidin-1-yl)but-2-en-1-one,

(31) 1-(3-(4-amino-5-((3,5-dimethoxyphenyl)ethynyl)-7H-pyrrolo[2,3-d]pyrimidin-7-yl)azetidin-1-yl)-4-(ethyl(methyl)amino)but-2-en-1-one,
(32) 1-(3-(4-amino-5-((3,5-dimethoxyphenyl)ethynyl)-7H-pyrrolo[2,3-d]pyrimidin-7-yl)azetidin-1-yl)-4-(isopropylamino)but-2-en-1-one,
(33) 1-(3-(4-amino-5-((3,5-dimethoxyphenyl)ethynyl)-7H-pyrrolo[2,3-d]pyrimidin-7-yl)azetidin-1-yl)-4-(diethylamino)but-2-en-1-one,
(34) 1-(3-(4-amino-5-((3,5-dimethoxyphenyl)ethynyl)-7H-pyrrolo[2,3-d]pyrimidin-7-yl)azetidin-1-yl)-4-((2-methoxyethyl)(methyl)amino)but-2-en-1-one,
(35) 1-(3-(4-amino-5-((3,5-dimethoxyphenyl)ethynyl)-7H-pyrrolo[2,3-d]pyrimidin-7-yl)azetidin-1-yl)-4-(4-hydroxypiperidin-1-yl)but-2-en-1-one,
(36) (S)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one,
(37) (R)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one,
(38) (2S,4S)-methyl-1-acryloyl-4-(4-amino-5-((3,5-dimethoxyphenyl)ethynyl)-7H-pyrrolo[2,3-d]pyrimidin-7-yl)pyrrolidine-2-carboxylate,
(39) 1-((2S,4S)-4-(4-amino-5-((3,5-dimethoxyphenyl)ethynyl)-7H-pyrrolo[2,3-d]pyrimidin-7-yl)-2-(1,3,4-oxadiazol-2-yl)pyrrolidin-1-yl)prop-2-en-1-one, and
(40) (S)-1-(3-(4-amino-3-((3,5-dimethoxyphenyl)ethynyl)-1H-pyrrolo[3,2-c]pyridin-1-yl)pyrrolidin-1-yl)prop-2-en-1-one.

Item 12. The antitumor agent, method, compound or a salt thereof, or use according to any one of items 1 to 11, wherein the 3,5-disubstituted benzene alkynyl compound or a salt thereof is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or a salt thereof.

Item 13. The antitumor agent, method, compound or a salt thereof, or use according to any one of items 1 to 12, wherein the tumor patient is resistant to at least one of ponatinib, regorafenib, intedanib, dovitinib lactate, lenvatinib mesylate, cediranib, oratinib, brivanib alaninate, AZD4547, NVP-BGJ398, sulfatinib, ARQ-087, S-49076, IMCA1, PRO001, and R3Mab.

Item 14. The antitumor agent, method, compound or a salt thereof, or use according to any one of items 1 to 13, wherein the tumor patient has a mutation at at least one of N550, V565, E566, and K660 of FGFR2.

Item 15. The antitumor agent, method, compound or a salt thereof, or use according to any one of items 1 to 13, wherein the tumor patient has a mutation at N550 of FGFR2.

Item 16. The antitumor agent, method, compound or a salt thereof, or use according to any one of items 1 to 13, wherein the tumor patient has a mutation at V565 of FGFR2.

Item 17. The antitumor agent, method, compound or a salt thereof, or use according to any one of items 1 to 13, wherein the tumor patient has a mutation at E566 of FGFR2.

Item 18. The antitumor agent, method, compound or a salt thereof, or use according to any one of items 1 to 13, wherein the tumor patient has a mutation at K660 of FGFR2.

Advantageous Effects of Invention

It was revealed that the compound represented by Formula (I) above or a salt thereof, which is the active ingredient of the present invention, unexpectedly exhibited antitumor effects on tumors resistant to conventional FGFR inhibitors. Therefore, the compound represented by Formula (I) or a salt thereof is very effective for, among various tumors, tumors resistant to conventional FGFR inhibitors.

BRIEF DESCRIPTION OF DRAWING

FIG. 1 shows the amino acid sequence (SEQ ID NO: 1) encoded by GenBank accession number NP_075259.

DESCRIPTION OF EMBODIMENTS

The present invention provides an antitumor agent comprising a 3,5-disubstituted benzene alkynyl compound represented by Formula (I) above or a salt thereof for administration to tumor patients resistant to FGFR inhibitors.

The tumor resistant to an FGFR inhibitor to be prevented and/or treated in the present invention refers to a tumor that responded to a conventionally known FGFR inhibitor, but has become resistant to the antitumor effect of the inhibitor due to the continuous administration thereof. Conventional FGFR inhibitors are, for example, ponatinib, regorafenib, intedanib, dovitinib lactate, lenvatinib mesylate, cediranib, oratinib, brivanib alaninate, AZD4547, NVP-BGJ398, sulfatinib, ARQ-087, S-49076, IMCA1, PRO001, R3Mab, and the like; and typically AZD4547, NVP-BGJ398, and the like. Therefore, in the present invention, examples of tumors resistant to FGFR inhibitors include tumors resistant to at least one of these FGFR inhibitors.

Examples of tumor patients resistant to FGFR inhibitors in the present invention include patients with a mutation at at least one of N550, V565, E566, and K660 of FGFR2. In particular, V565 corresponds to a characteristic amino acid residue called a "gatekeeper" in the kinase. Patients with a mutation at the gatekeeper residue are also included. In this specification, the term "FGFR2" includes a protein having an amino acid sequence (SEQ ID NO: 1; FIG. 1) encoded by GenBank accession number NP_075259, a homologue, isoform, mutant, or derivative thereof, a protein cut from the precursor protein, and the like. In the present invention, the position of the FGFR2 mutation denotes a position corresponding to the position in the amino acid sequence represented by SEQ ID NO: 1. The "mutation at N550" in FGFR2 indicates that asparagine in FGFR2 at a position corresponding to the 550th amino acid of SEQ ID NO: 1 is mutated. Examples of such FGFR2 mutations include N550H, V565I, E566G, K660M, and the like. Therefore, even if the mutation position in a certain FGFR2 is different from the mutation position of the amino acid number encoded by NP_075259 due to the presence of splicing variants, deletions, insertions, etc., the mutation at the position corresponding to the amino acid sequence encoded by NP_075259 is also included.

The compound represented by Formula (I) above, which is the active ingredient of the antitumor agent of the present invention, is a 3,5-disubstituted benzene alkynyl compound containing a condensed heteroaryl group substituted for an α,β-unsaturated amide via a spacer moiety, and is not disclosed in any of the above prior art documents.

In the present specification, the term "$C_1$-$C_6$ alkyl" refers to a straight or branched alkyl group having 1 to 6 carbon atoms. Specific examples thereof include methyl, ethyl, n-propyl, isopropyl, n-butyl, isobutyl, sec-butyl, tert-butyl, pentyl, hexyl, and the like. The $C_1$-$C_6$ alkyl is preferably a straight or branched alkyl group having 1 to 4 carbon atoms (a $C_1$-$C_4$ alkyl group), and more preferably methyl, ethyl, isopropyl, and tert-butyl.

In this specification, the term "$C_3$-$C_{10}$ cycloalkyl" refers to a monocyclic or polycyclic cycloalkyl group having 3 to 10 carbon atoms, and is preferably a monocyclic cycloalkyl group having 3 to 6 carbon atoms (a $C_3$-$C_6$ cycloalkyl group). Specific examples thereof include cyclopropyl, cyclobutyl, cyclopentyl, cyclohexyl, cycloheptyl, decalyl, and the like. Cyclopropyl and cyclobutyl are preferable. In this specification, the divalent moiety represented by

of the group represented by Formula (A)

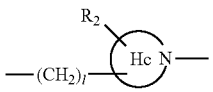

(A)

(wherein $R_2$ and l are as defined above)
is a $C_3$-$C_{10}$ divalent heterocycloalkylene group containing at least one nitrogen atom in the ring and further containing 0 to 2 same or different heteroatoms selected from oxygen and sulfur atoms in the ring (a nitrogen-containing $C_3$-$C_{10}$ heterocycloalkylene group), and is preferably a $C_3$-$C_5$ heterocycloalkylene group containing 1 to 3 nitrogen atoms in the ring and further containing 0 to 1 oxygen atom in the ring (a nitrogen-containing $C_3$-$C_5$ heterocycloalkylene group). Specific examples thereof include azetidinylene, pyrrolidinylene, piperidinylene, piperazinylene, morpholinylene, octahydroquinolinylene, octahydroindolylene, and the like. Among them, azetidinylene, pyrrolidinylene, piperidinylene, piperazinylene, and morpholinylene are preferable.

The group represented by Formula (A)

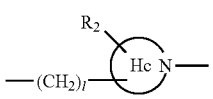

(A)

refers to a divalent nitrogen-containing $C_3$-$C_{10}$ heterocycloalkylene group represented by

wherein the nitrogen atom has one arm and the other arm is connected to a substituent (—(CH$_2$)$_l$—), and a substituent $R_2$ is present on the ring.

In this specification, the divalent moiety represented by

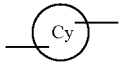

of the group represented by Formula (B)

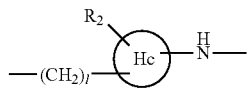

(B)

(wherein $R_2$ and l are as defined above)
refers to a monocyclic or polycyclic divalent cycloalkylene group having 3 to 10 carbon atoms (a $C_3$-$C_{10}$ cycloalkylene group), and preferably a monocyclic divalent cycloalkylene group having 3 to 6 carbon atoms (a $C_3$-$C_6$ cycloalkylene group). Specific examples thereof include cyclopropylene, cyclobutylene, cyclopentylene, cyclohexylene, cycloheptylene, decalylene, and the like. Cyclopropylene and (1,2- or 1,3-)cyclobutylene are preferable.

Formula (B)

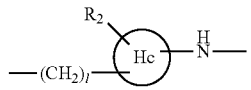

(B)

refers to a divalent $C_3$-$C_{10}$ cycloalkylene group represented by

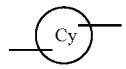

wherein one arm is connected to an adjacent amino group (NH) and the other arm is connected to a substituent (—(CH$_2$)$_l$—), and a substituent $R_2$ is present on the ring.

In the present specification, the divalent moiety represented by

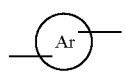

of the group represented by Formula (C)

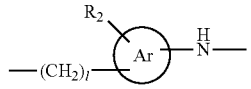

(C)

(wherein $R_2$ and l are as defined above)
refers to a divalent arylene group having 6 to 12 carbon atoms (a $C_6$-$C_{12}$ arylene group). Specific examples thereof include phenylene, naphthylene, biphenylene, and the like. Phenylene is preferable.

Formula (C)

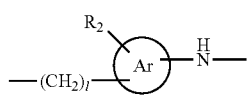

(C)

refers to a divalent $C_6$-$C_{12}$ arylene group represented by

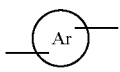

wherein one arm is connected to an adjacent amino group (NH) and the other arm is connected to a substituent (—$(CH_2)_l$—), and a substituent $R_2$ is present on the ring.

In this specification, the monovalent moiety represented by

of the group represented by Formula (D)

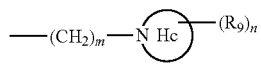

(D)
(wherein $R_9$, m, and n are as defined above)
refers to a $C_3$-$C_{10}$ heterocycloalkyl group containing at least one nitrogen atom in the ring and further containing 0 to 2 same or different heteroatoms selected from oxygen and sulfur atoms in the ring (a nitrogen-containing $C_3$-$C_{10}$ heterocycloalkyl group), and is preferably a $C_3$-$C_5$ heterocycloalkyl group containing 1 to 3 nitrogen atoms in the ring and further containing 0 to 1 oxygen atom in the ring (a nitrogen-containing $C_3$-$C_5$ heterocycloalkyl group). Specific examples thereof include azetidinyl, pyrrolidinyl, piperidinyl, piperazinyl, morpholinyl, octahydroquinolinyl, octahydroindolyl, and the like. Azetidinyl, pyrrolidinyl, piperidinyl, piperazinyl, and morpholinyl are preferable.

Formula (D)

Formula (D)

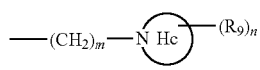

denotes a nitrogen-containing $C_3$-$C_{10}$ heterocycloalkyl group represented by

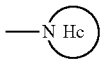

wherein the nitrogen atom is bound to a substituent (—$(CH_2)_m$—), and n substituents (—$(R_9)_n$) are present on the ring.

In this specification, the "$C_2$-$C_9$ heteroaryl" refers to a monocyclic or bicyclic $C_2$-$C_9$ heteroaryl group containing 1 to 3 same or different heteroatoms selected from nitrogen, oxygen, and sulfur atoms; and is preferably a monocyclic $C_2$-$C_5$ heteroaryl group containing 1 to 3 same or different heteroatoms selected from nitrogen, oxygen, and sulfur atoms (a $C_2$-$C_5$ heteroaryl group). Specific examples thereof include thienyl, furyl, pyrrolyl, triazolyl, imidazolyl, pyrazolyl, oxadiazolyl, isothiazolyl, isoxazolyl, pyridyl, pyrazinyl, pyrimidinyl, pyridazinyl, isobenzofuryl, indolizinyl, isoindolyl, indolyl, indazolyl, quinolyl, isoquinolyl, phthalazinyl, naphthyridinyl, and the like. 1,3,4-Oxadiazolyl is preferable.

In this specification, the term "$C_2$-$C_6$ alkynyl" refers to a straight or branched $C_2$-$C_6$ alkynyl group having at least one carbon-carbon triple bond. Specific examples thereof include ethynyl, 2-propynyl, 2-hexynyl, and the like. Ethynyl is preferable.

In this specification, the term "hydroxy-$C_1$-$C_6$ alkyl" refers to a straight or branched $C_1$-$C_6$ alkyl group having one hydroxy group. Specific examples thereof include hydroxymethyl, hydroxyethyl, hydroxypropyl, hydroxybutyl, hydroxypentyl, hydroxyhexyl, and the like. Among them, hydroxymethyl, 2-hydroxyethyl, 2-hydroxypropyl, and 2-hydroxybutyl are preferable.

In this specification, the term "di($C_1$-$C_6$ alkyl)amino-$C_1$-$C_6$ alkyl" refers to a straight or branched $C_1$-$C_6$ alkyl group having an amino group having two straight or branched $C_1$-$C_6$ alkyl groups. A straight or branched $C_1$-$C_4$ alkyl group having an amino group having two straight or branched $C_1$-$C_4$ alkyl groups (a di($C_1$-$C_4$ alkyl)amino-$C_1$-$C_4$ alkyl group) is preferable. Specific examples thereof include dimethylaminomethyl, dimethylaminoethyl, dimethylaminopropyl, dimethylaminobutyl, dimethylaminopentyl, dimethylaminohexyl, diethylaminomethyl, diethylaminoethyl, diethylaminopropyl, diethylaminobutyl, diethylaminopentyl, diethylaminohexyl, dipropylaminomethyl, dibutylaminomethyl, dipentylaminomethyl, dihexylaminomethyl, ethyl(methyl)aminomethyl, and the like. Dimethylaminomethyl and diethylaminomethyl are preferable.

In this specification, the term "$C_1$-$C_6$ alkoxy-$C_1$-$C_6$ alkyl" refers to a straight or branched $C_1$-$C_6$ alkyl group having a straight or branched $C_1$-$C_6$ alkoxy group. It is preferably a straight or branched $C_1$-$C_4$ alkyl group having a straight or branched $C_1$-$C_4$ alkoxy group (a $C_1$-$C_4$ alkoxy-$C_1$-$C_4$ alkyl group). Specific examples of such groups include methoxymethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, ethoxyhexyl, propoxymethyl, butoxymethyl, pentyloxymethyl, hexyloxymethyl, and the like. Among them, 2-methoxyethyl is preferable.

In this specification, examples of the "halogen" include chlorine, bromine, fluorine, and iodine. Fluorine is preferable.

In Formula (I), the following combinations of $X_1$ and $X_2$ are preferable. (1) When $X_2$ is N, $X_1$ is N or CH. (2) When $X_2$ is CH, $X_2$ is CH.

In Formula (I), l is preferably 0 or 1.

In Formula (I), Y is preferably a group represented by Formula (A)

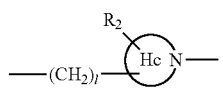

(wherein $R_2$ and l are as defined above) or a group represented by Formula (C)

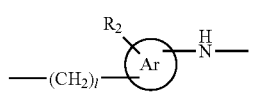

(wherein $R_2$ and l are as defined above). More preferably, the divalent moiety represented by

of a group represented by Formula (A) is pyrrolidinylene, azetidinylene, or piperidinylene, or the divalent moiety represented by

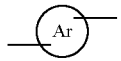

of a group represented by Formula (C) is phenylene.

In Formula (I), the following combinations of Y and Z are preferable. When Y is a group represented by Formula (A)

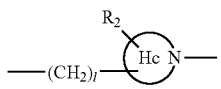
(A)

(wherein $R_2$ and l are as defined above), Z is $-C(R_4)=C(R_5)(R_6)$ or $-C\equiv C-R_7$. When Y is a group represented by Formula (B) or (C):

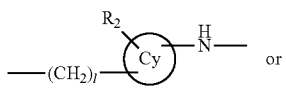
(B)

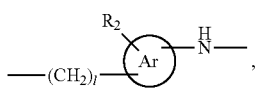
(C)

or

, (wherein $R_2$ and l are as defined above), Z is $-C(R_4)=C(R_5)(R_6)$.

In Formula (I), $R_1$ is preferably $C_1$-$C_4$ alkyl, and more preferably methyl or ethyl.

In Formula (I), $R_2$ is preferably hydrogen, $C_2$-$C_6$ alkynyl, $-C(=O)OR_x$, hydroxy-$C_1$-$C_4$ alkyl, or $C_2$-$C_9$ heteroaryl optionally having $R_3$, and more preferably ethynyl, methoxycarbonyl, hydroxymethyl, or 1,3,4-oxadiazolyl optionally having $R_3$.

In Formula (I), $R_3$ is preferably $C_1$-$C_4$ alkyl or di-($C_1$-$C_4$ alkyl)amino-$C_1$-$C_4$ alkyl, and more preferably methyl or dimethylaminomethyl.

In Formula (I), $R_4$ is preferably hydrogen or halogen, more preferably hydrogen or fluorine, and even more preferably hydrogen.

In Formula (I), $R_5$ and $R_6$ are preferably hydrogen, $C_1$-$C_4$ alkyl group optionally having $R_8$, or a group represented by Formula (D)

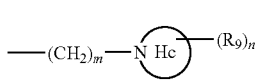
(D)

(wherein $R_9$, m and n are as defined above), and more preferably hydrogen, methyl having $R_8$, or a group represented by Formula (D)

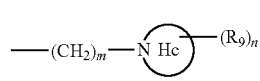
(D)

(wherein $R_9$, m, and n are as defined above).

In Formula (I), m is preferably 1.
In Formula (I), $R_9$ is preferably $C_1$-$C_4$ alkyl, fluorine, or hydroxy, and more preferably methyl, fluorine, or hydroxy.
In Formula (I), n is preferably 0 or 1.
In Formula (I), $R_7$ is preferably hydrogen, $C_1$-$C_4$ alkyl, or hydroxy-$C_1$-$C_4$ alkyl, and more preferably hydrogen, hydroxymethyl, methyl, or 2-hydroxy-2-methyl-ethyl.
In Formula (I), $R_8$ is preferably hydroxy or $-N(R_x)(R_y)$. In this formula, $R_x$ and $R_y$ are preferably hydrogen, $C_1$-$C_4$ alkyl, $C_3$-$C_{10}$ cycloalkyl, or $C_1$-$C_4$ alkoxy-$C_1$-$C_4$ alkyl, and more preferably hydrogen, methyl, ethyl, tert-butyl, isopropyl, cyclopropyl, cyclobutyl, or 2-methoxyethyl.

Preferable Compounds (I) are compounds represented by Formula (I) wherein $R_1$ is $C_1$-$C_4$ alkyl; $X_1$ and $X_2$ are independently N or CH; Y is a group represented by Formula (A) or (C):

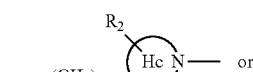
(A)

or

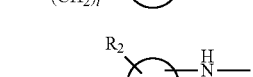
(C)

;

$R_2$ is hydrogen, $C_2$-$C_6$ alkynyl, $-C(=O)OR_x$, hydroxy-$C_1$-$C_4$ alkyl, or $C_2$-$C_9$ heteroaryl optionally having $R_3$; $R_3$ is $C_1$-$C_4$ alkyl or di($C_1$-$C_4$ alkyl)amino-$C_1$-$C_4$ alkyl; Z is $-C(R_4)=C(R_5)(R_6)$ or $-C\equiv C-R_7$; $R_4$ is hydrogen or halogen; $R_5$ and $R_6$ are the same or different, and each represents hydrogen, $C_3$-$C_4$ alkyl optionally having $R_8$, or a group represented by Formula (D)

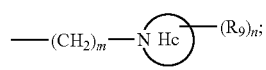
(D)

;

$R_7$ is hydrogen, $C_1$-$C_4$ alkyl, or hydroxy-$C_1$-$C_4$ alkyl; $R_8$ is hydroxy or $-N(R_x)(R_y)$; $R_9$ is $C_1$-$C_4$ alkyl, fluorine, or hydroxy; $R_x$ and $R_y$ are the same or different, and each represents hydrogen, $C_1$-$C_4$ alkyl, $C_3$-$C_{10}$ cycloalkyl, or $C_1$-$C_4$ alkoxy-$C_1$-$C_4$ alkyl; and l is 0 or 1, m is 1, and n is 0 or 1.

More preferable Compounds (I) are compounds represented by Formula (I) wherein $R_1$ is $C_1$-$C_4$ alkyl; $X_1$ and $X_2$ are such that (1) when $X_4$ is N, $X_1$ is N or CH, and (2) when $X_2$ is CH, $X_1$ is CH; in Y, the divalent moiety represented by

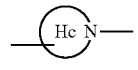

of the group represented by Formula (A)

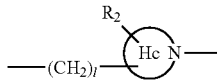

(A)

is pyrrolidinylene, azetidinylene, or piperidinylene, or the divalent moiety represented by

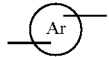

of the group represented by Formula (C)

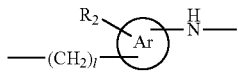

(C)

is phenylene;
(a) when Y is a group represented by Formula (A)

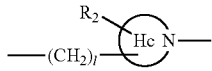

(A)

(wherein $R_2$ is hydrogen, ethynyl, methoxycarbonyl, hydroxymethyl, or 1,3,4-oxadiazolyl optionally having $R_3$; $R_3$ is $C_1$-$C_4$ alkyl; and l is 0 or 1), Z is —C($R_4$)=C($R_5$)($R_6$) or —C≡C—$R_7$, (b) when Y is a group represented by Formula (C)

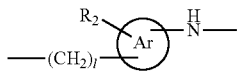

(C)

(wherein $R_2$ is hydrogen; and l is 0 or 1), Z is —C($R_4$)=C($R_5$)($R_6$); $R_4$ is hydrogen or fluorine; $R_5$ and $R_6$ are the same or different, and each represents hydrogen, $C_1$-$C_4$ alkyl optionally having $R_8$, or a group represented by Formula (D)

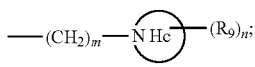

(D)

$R_7$ is hydrogen, hydroxymethyl, methyl, or 2-hydroxy-2-methyl-ethyl; $R_8$ is —N($R_x$)($R_y$); $R_9$ is $C_1$-$C_4$ alkyl, fluorine, or hydroxy; $R_x$ and $R_y$ are the same or different, and each represents hydrogen, $C_1$-$C_4$ alkyl, $C_3$-$C_{10}$ cycloalkyl, or $C_1$-$C_4$ alkoxy-$C_1$-$C_4$ alkyl, m is 1, and n is 0 or 1.

Even more preferable Compounds (I) are compounds represented by Formula (I) wherein $R_1$ is methyl or ethyl; $X_1$ and $X_2$ are such that (1) when $X_2$ is N, $X_1$ is N or CH, and (2) when $X_2$ is CH, $X_1$ is CH; in Y, the divalent moiety represented by

is pyrrolidinylene, azetidinylene, piperidinylene, or the divalent moiety represented by

is phenylene;
(a) when Y is a group represented by Formula (A)

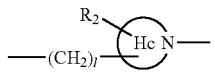

(A)

(wherein $R_2$ is hydrogen, ethynyl, methoxycarbonyl, hydroxymethyl, or 1,3,4-oxadiazolyl optionally having methyl; and l is 0 or 1), Z is —C($R_4$)=C($R_5$)($R_6$) or —C≡C—$R_7$, (b) when Y is a group represented by Formula (C)

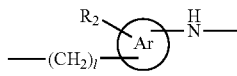

(C)

(wherein $R_2$ is hydrogen; and l is 1),
Z is —C($R_4$)=C($R_5$)($R_6$); $R_4$ is hydrogen; $R_5$ and $R_6$ are the same or different, and each represents hydrogen, methyl having $R_8$, or the monovalent moiety represented by

of the group represented by Formula (D)

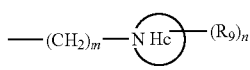

(D)

is pyrrolidinyl, piperidinyl, azetidinyl, piperazinyl, or morpholinyl; $R_7$ is hydrogen, hydroxymethyl, methyl, or 2-hydroxy-2-methyl-ethyl; $R_8$ is —N($R_x$)($R_y$); $R_9$ is methyl, fluorine, or hydroxy and; $R_x$ and $R_y$ are the same or different, and each represents hydrogen, methyl, ethyl, tert-butyl, isopropyl, cyclopropyl, cyclobutyl, or 2-methoxyethyl; and m is 1, and n is 0 or 1.

Specific examples of preferable Compounds (I) include the following:
(1) (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one (Compound of Example 2),
(2) (S)-1-(3-(4-amino-3-((3,5-dimethoxyphenyl)ethynyl)-1H-pyrazolo[3,4-d]pyrimidin-1-yl)pyrrolidin-1-yl)prop-2-yn-1-one (Compound of Example 5),
(3) (S)-1-(3-(4-amino-3-((3,5-diethoxyphenyl)ethynyl)-1H-pyrazolo[3,4-d]pyrimidin-1-yl)pyrrolidin-1-yl)prop-2-en-1-one (Compound of Example 8), (4) 1-(3-(4-amino-3-((3,5-dimethoxyphenyl)ethynyl)-1H-pyrazolo[3,4-d]pyrimidin-1-yl)azetidin-1-yl)prop-2-en-1-one (Compound of Example 9),
(5) 1-(3-(4-amino-3-((3,5-dimethoxyphenyl)ethynyl)-1H-pyrazolo[3,4-d]pyrimidin-1-yl)azetidin-1-yl)-4-hydroxy-but-2-yn-1-one (Compound of Example 10),
(6) 1-(3-(4-amino-3-((3,5-dimethoxyphenyl)ethynyl)-1H-pyrazolo[3,4-d]pyrimidin-1-yl)azetidin-1-yl)-4-(dimethylamino)but-2-en-1-one (Compound of Example 12),
(7) 1-(3-(4-amino-3-((3,5-dimethoxyphenyl)ethynyl)-1H-pyrazolo[3,4-d]pyrimidin-1-yl)azetidin-1-yl)-4-(cyclopropylamino)but-2-en-1-one (Compound of Example 13),
(8) 1-(3-(4-amino-3-((3,5-dimethoxyphenyl)ethynyl)-1H-pyrazolo[3,4-d]pyrimidin-1-yl)azetidin-1-yl)-4-(isopropylamino)but-2-en-1-one (Compound of Example 14),
(9) 1-(3-(4-amino-3-((3,5-dimethoxyphenyl)ethynyl)-1H-pyrazolo[3,4-d]pyrimidin-1-yl)azetidin-1-yl)-4-(ethyl(methyl)amino)but-2-en-1-one (Compound of Example 15),
(10) 1-(3-(4-amino-3-((3,5-dimethoxyphenyl)ethynyl)-1H-pyrazolo[3,4-d]pyrimidin-1-yl)azetidin-1-yl)-4-(cyclobutylamino)but-2-en-1-one (Compound of Example 16),
(11) 1-(3-(4-amino-3-((3,5-dimethoxyphenyl)ethynyl)-1H-pyrazolo[3,4-d]pyrimidin-1-yl)azetidin-1-yl)-4-(diethylamino)but-2-en-1-one (Compound of Example 17),
(12) 1-(3-(4-amino-3-((3,5-dimethoxyphenyl)ethynyl)-1H-pyrazolo[3,4-d]pyrimidin-1-yl)azetidin-1-yl)-4-(tert-butylamino)but-2-en-1-one (Compound of Example 18),
(13) 1-(3-(4-amino-3-((3,5-dimethoxyphenyl)ethynyl)-1H-pyrazolo[3,4-d]pyrimidin-1-yl)azetidin-1-yl)-4-(isopropyl(methyl)amino)but-2-en-1-one (Compound of Example 19),
(14) 1-(3-(4-amino-3-((3,5-dimethoxyphenyl)ethynyl)-1H-pyrazolo[3,4-d]pyrimidin-1-yl)azetidin-1-yl)-4-(piperidin-1-yl)but-2-en-1-one (Compound of Example 20),
(15) (S)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one (Compound of Example 22),
(16) (R)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one (Compound of Example 23),
(17) 1-((2S,4S)-4-(4-amino-3-((3,5-dimethoxyphenyl)ethynyl)-1H-pyrazolo[3,4-d]pyrimidin-1-yl)-2-(hydroxymethyl)pyrrolidin-1-yl)prop-2-en-1-one (Compound of Example 28),
(18) 1-(2S,4S)-4-(4-amino-3-((3,5-dimethoxyphenyl)ethynyl)-1H-pyrazolo[3,4-d]pyrimidin-1-yl)-2-ethynylpyrrolidin-1-yl)prop-2-en-1-one (Compound of Example 32),
(19) (S)-1-(3-(4-amino-5-((3,5-dimethoxyphenyl)ethynyl)-7H-pyrrolo[2,3-d]pyrimidin-7-yl)pyrrolidin-1-yl)-4-(dimethylamino)but-2-en-1-one (Compound of Example 38),
(20) (S)-1-(3-(4-amino-5-((3,5-dimethoxyphenyl)ethynyl)-7H-pyrrolo[2,3-d]pyrimidin-7-yl)pyrrolidin-1-yl)prop-2-en-1-one (Compound of Example 39),
(21) (S)-1-(3-(4-amino-5-((3,5-dimethoxyphenyl)ethynyl)-7H-pyrrolo[2,3-d]pyrimidin-7-yl)pyrrolidin-1-yl)-4-(pyrrolidin-1-yl)but-2-en-1-one (Compound of Example 40),
(22) (S)-1-(3-(4-amino-5-((3,5-dimethoxyphenyl)ethynyl)-7H-pyrrolo[2,3-d]pyrimidin-7-yl)pyrrolidin-1-yl)-4-(4-hydroxypiperidin-1-yl)but-2-en-1-one (Compound of Example 42),
(23) (S)-1-(3-(4-amino-5-((3,5-dimethoxyphenyl)ethynyl)-7H-pyrrolo[2,3-d]pyrimidin-7-yl)pyrrolidin-1-yl)but-2-yn-1-one (Compound of Example 46),
(24) (S)-1-(3-(4-amino-5-((3,5-dimethoxyphenyl)ethynyl)-7H-pyrrolo[2,3-d]pyrimidin-7-yl)pyrrolidin-1-yl)-4-hydroxy-4-methylpent-2-yn-1-one (Compound of Example 47),
(25) 1-((S)-3-(4-amino-5-((3,5-dimethoxyphenyl)ethynyl)-7H-pyrrolo[2,3-d]pyrimidin-7-yl)pyrrolidin-1-yl)-4-((S)-3-fluoropyrrolidin-1-yl)but-2-en-1-one (Compound of Example 49),
(26) (S)-1-(3-(4-amino-5-((3,5-dimethoxyphenyl)ethynyl)-7H-pyrrolo[2,3-d]pyrimidin-7-yl)pyrrolidin-1-yl)-4-(piperidin-1-yl)but-2-en-1-one (Compound of Example 50),
(27) 1-(3-(4-amino-5-((3,5-dimethoxyphenyl)ethynyl)-7H-pyrrolo[2,3-d]pyrimidin-7-yl)azetidin-1-yl)prop-2-en-1-one (Compound of Example 51),
(28) 1-(3-(4-amino-5-((3,5-dimethoxyphenyl)ethynyl)-7H-pyrrolo[2,3-d]pyrimidin-7-yl)azetidin-1-yl)-4-(dimethylamino)but-2-en-1-one (Compound of Example 52),
(29) 1-(3-(4-amino-5-((3,5-dimethoxyphenyl)ethynyl)-7H-pyrrolo[2,3-d]pyrimidin-7-yl)azetidin-1-yl)-4-(pyrrolidin-1-yl)but-2-en-1-one (Compound of Example 53),
(30) 1-(3-(4-amino-5-((3,5-dimethoxyphenyl)ethynyl)-7H-pyrrolo[2,3-d]pyrimidin-7-yl)azetidin-1-yl)-4-(azetidin-1-yl)but-2-en-1-one (Compound of Example 55),
(31) 1-(3-(4-amino-5-((3,5-dimethoxyphenyl)ethynyl)-7H-pyrrolo[2,3-d]pyrimidin-7-yl)azetidin-1-yl)-4-(ethyl(methyl)amino)but-2-en-1-one (Compound of Example 56),
(32) 1-(3-(4-amino-5-((3,5-dimethoxyphenyl)ethynyl)-7H-pyrrolo[2,3-d]pyrimidin-7-yl)azetidin-1-yl)-4-(isopropylamino)but-2-en-1-one (Compound of Example 57),
(33) 1-(3-(4-amino-5-((3,5-dimethoxyphenyl)ethynyl)-7H-pyrrolo[2,3-d]pyrimidin-7-yl)azetidin-1-yl)-4-(diethylamino)but-2-en-1-one (Compound of Example 59),
(34) 1-(3-(4-amino-5-((3,5-dimethoxyphenyl)ethynyl)-7H-pyrrolo[2,3-d]pyrimidin-7-yl)azetidin-1-yl)-4-((2-methoxyethyl)(methyl)amino)but-2-en-1-one (Compound of Example 60),
(35) 1-(3-(4-amino-5-((3,5-dimethoxyphenyl)ethynyl)-7H-pyrrolo[2,3-d]pyrimidin-7-yl)azetidin-1-yl)-4-(4-hydroxypiperidin-1-yl)but-2-en-1-one (Compound of Example 61),
(36) (S)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Compound of Example 62),
(37) (R)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Compound of Example 63),
(38) (2S,4S)-methyl-1-acryloyl-4-(4-amino-5-((3,5-dimethoxyphenyl)ethynyl)-7H-pyrrolo[2,3-d]pyrimidin-7-yl)pyrrolidine-2-carboxylate (Compound of Example 66),
(39) 1-((2S,4S)-4-(4-amino-5-((3,5-dimethoxyphenyl)ethynyl)-7H-pyrrolo[2,3-d]pyrimidin-7-yl)-2-(1,3,4-oxadiazol-2-yl)pyrrolidin-1-yl)prop-2-en-1-one (Compound of Example 68), and
(40) (S)-1-(3-(4-amino-3-((3,5-dimethoxyphenyl)ethynyl)-1H-pyrrolo[3,2-c]pyridin-1-yl)pyrrolidin-1-yl)prop-2-en-1-one (Compound of Example 73).

Next, the method for producing Compound (I), which is the active ingredient of the antitumor agent according to the present invention, will be explained. Compound (I) can be produced, for example, by the following production methods or by the methods described in Examples. However, the method for producing Compound (I) is not limited to these reaction examples.

Production method 1

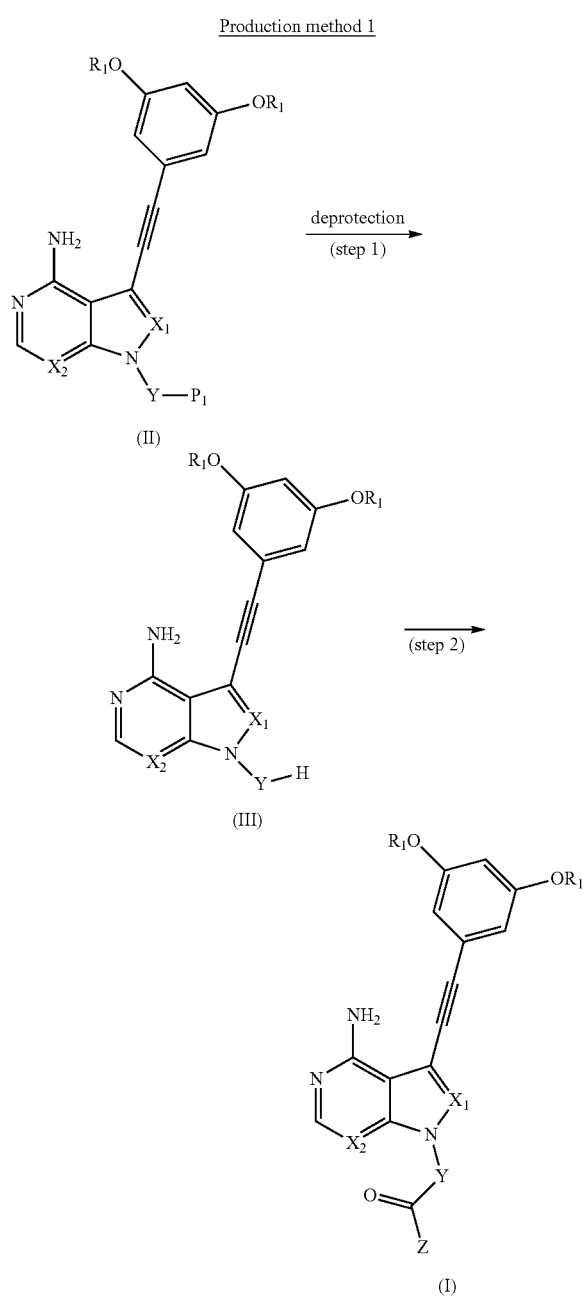

(wherein $P_1$ is a protecting group of the amino group contained in Y; and $R_1$, $X_1$, $X_2$, Y, and Z are as defined above.)

(Step 1) In this step, the protected amino group of the compound of Formula (II) is deprotected to produce the compound of Formula (III). The method for the deprotection can be performed according to a known method, such as the method described in Protective Groups in Organic Synthesis, T. W. Greene, John Wiley & Sons (1981); or methods similar thereto. An example of the protecting group is tert-butyloxycarbonyl. If a tert-butyloxycarbonyl group is used as a protecting group, the deprotection is preferably performed under acidic conditions. Examples of acids that can be used include hydrochloric acid, acetic acid, trifluoroacetic acid, sulfuric acid, methanesulfonic acid, tosic acid, and the like. Such an acid is preferably used in an amount of 1 to 100 moles per mole of Compound (II).

Any solvent that does not adversely affect the reaction can be used. Examples thereof include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), or a mixture thereof. The reaction time is 0.1 to 100 hours, and preferably 0.5 to 24 hours. The reaction temperature is 0 to 120° C., and preferably 0 to 90° C.

The thus-obtained compound of Formula (III) can be subjected to the subsequent step after or without isolation and purification by known separation and purification means, such as concentration, vacuum concentration, crystallization, solvent extraction, reprecipitation, and chromatography.

(Step 2) In this step, the compound of Formula (III) is amidated with a carboxylic acid represented by Z—COOH or with an acid halide represented by Z—C(=O)-L (wherein L is chlorine or bromine) to produce the compound of Formula (I).

When a carboxylic acid represented by Z—COOH is used as an amidation reagent, the reaction is performed by using the carboxylic acid in an amount of 0.5 to 10 moles, and preferably 1 to 3 moles, per mole of the compound of Formula (III) in the presence of a suitable condensing agent. The carboxylic acid may be a commercially available product, or can be produced according to a known method.

Any reaction solvent that does not adversely affect the reaction can be used. Examples of preferable solvents include isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, and mixed solvents thereof. The reaction temperature is usually −78 to 200° C., and preferably 0 to 50° C. The reaction time is typically 5 minutes to 3 days, and preferably 5 minutes to 10 hours.

Examples of the condensing agent include diphenylphosphoryl azide, N,N'-dicyclohexylcarbodiimide, benzotriazol-1-yloxy-trisdimethylaminophosphonium salts, 4-(4,6-dimethoxy-1,3,5-triazin-2-yl)-4-methylmopholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, O-(7-azabenzotriazo-1-yl)-N,N,N',N'-tetramethyluronium hexafluorophosphate, and the like.

A base can be optionally added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base is added in an amount of 1 to 100 moles, and preferably 1 to 10 moles, per mole of the compound of Formula (III).

When an acid halide represented by Z—C(=O)-L (wherein L is chlorine or bromine) is used as an amidation reagent, the acid halide is used in an amount of 0.5 to 5 moles, and preferably 0.9 to 1.1 moles, per mole of the compound of Formula (III). The acid halide may be a commercially available product, or can be produced according to a known method.

Any reaction solvent that does not adversely affect the reaction can be used. Examples of preferable solvents include toluene, benzene, methylene chloride, chloroform, tetrahydrofuran, 1,4-dioxane, dimethylformamide, dimethylacetamide, N-methylpyrrolidinone, and mixed solvents thereof. The reaction temperature is typically −78 to 200° C., and preferably −20 to 50° C. The reaction time is typically 5 minutes to 3 days, and preferably 5 minutes to 10 hours.

A base can be optionally added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base is added in an amount of 1 to 100 moles, preferably 1 to 10 moles, per mole of the compound of Formula (III).

The thus-obtained compound of Formula (I) can be isolated and purified by known separation and purification means, such as concentration, vacuum concentration, crystallization, solvent extraction, reprecipitation, and chromatography.

Among Compounds (I), compound of Formula (I') or (I") can also be produced by production method 2 using, for example, Compound (III) obtained in step 1 of production method 1 as a starting compound, and using a specific amine.

Production method 2

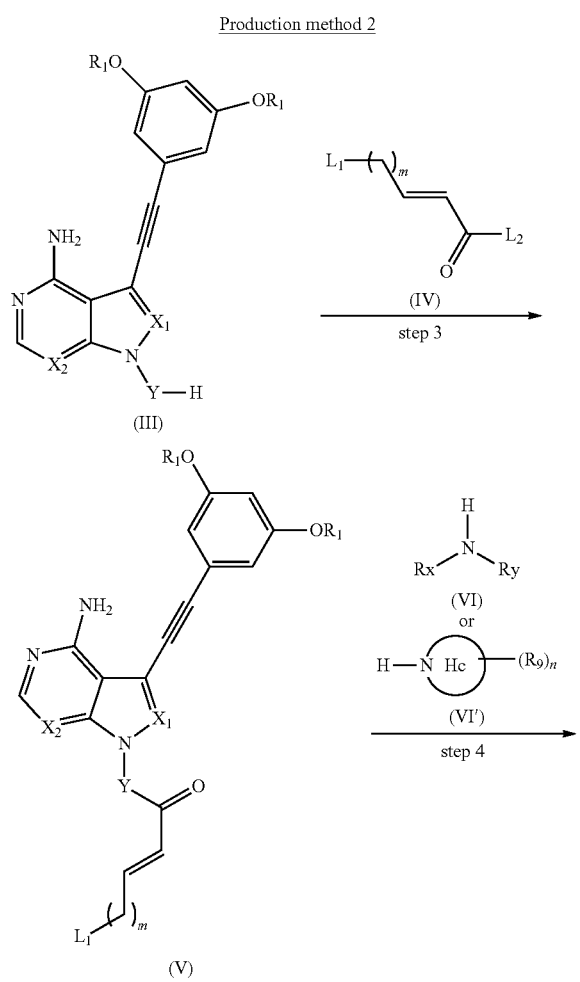

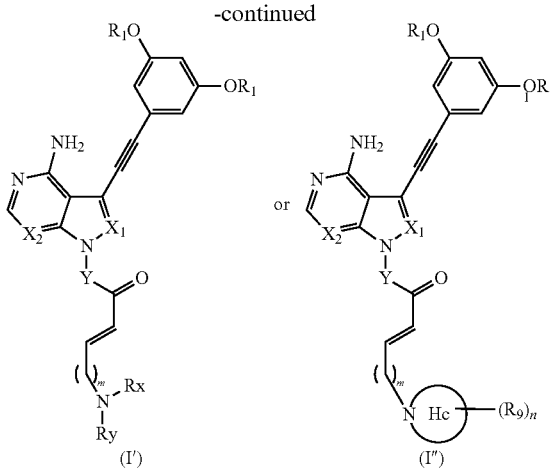

(wherein $L_1$ and $L_2$ are halogen; H of Y—H is hydrogen directly bound to a nitrogen atom; and $X_1$, $X_2$, Y, $R_x$, $R_y$, $R_1$,

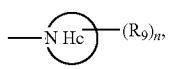

m, and n are as defined above.)

(Step 3) In this step, the compound of Formula (III) is amidated with an acid halide represented by Formula (IV) to produce the compound of Formula (V).

Examples of halogen atoms represented by $L_1$ or $L_2$ in Formula (IV) include bromine and chlorine. The compound represented by Formula (IV) may be a commercially available product, or can be produced according to a known method.

The compound of Formula (IV) is used in an amount of 0.5 to 5 moles, and preferably 0.9 to 1.1 moles, per mole of Compound (III).

A base can be optionally added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 10 moles, per mole of the compound of Formula (III).

Any reaction solvent that does not adversely affect the reaction can be used. Examples of preferable reaction solvents include toluene, benzene, methylene chloride, chloroform, tetrahydrofuran, 1,4-dioxane, dimethylformamide, dimethylacetamide, N-methylpyrrolidinone, and mixed solvents thereof. The reaction temperature is typically −78 to 200° C., and preferably 0 to 50° C. The reaction time is typically 5 minutes to 3 days, and preferably 5 minutes to 10 hours.

The thus-obtained compound of Formula (V) can be subjected to the subsequent step after or without isolation and purification by known separation and purification means, such as concentration, vacuum concentration, crystallization, solvent extraction, reprecipitation, and chromatography.

(Step 4) In this step, the compound of Formula (V) is alkylated with an amine represented by Formula (VI) or (VI') to produce the compound of Formula (I') or (I").

The compound of Formula (VI) or (VI') can be used in an amount of 1 to 20 moles, and preferably 1 to 10 moles, per mole of the compound of Formula (V).

Further, a base can optionally be added for the reaction. Examples of such bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 20 moles, per mole of the compound of Formula (V).

Any reaction solvent that does not adversely affect the reaction can be used. For example, N,N-dimethylformamide, N,N-dimethylacetamide, dimethyl sulfoxide, tetrahydrofuran, 1,4-dioxane, N-methylpyrrolidin-2-one, acetonitrile, and the like can be used singly, or as a mixture. The reaction time is 0.1 to 100 hours, and preferably 0.5 to 24 hours. The reaction temperature is 0° C. to the boiling temperature of the solvent, and preferably 0 to 100° C.

The thus-obtained compound of Formula (I') or (I") can be isolated and purified by known separation and purification means, such as concentration, vacuum concentration, crystallization, solvent extraction, reprecipitation, and chromatography.

The compound of Formula (II) used for producing Compound (I) can be produced, for example, by production method 3 or 4.

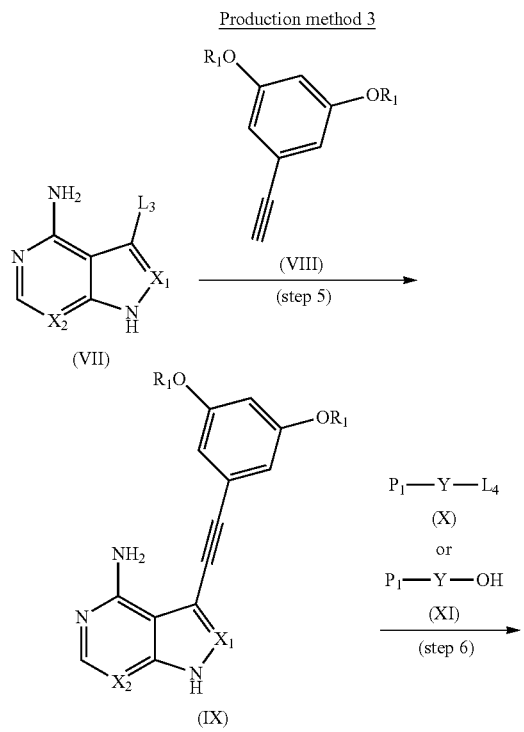

Production method 3

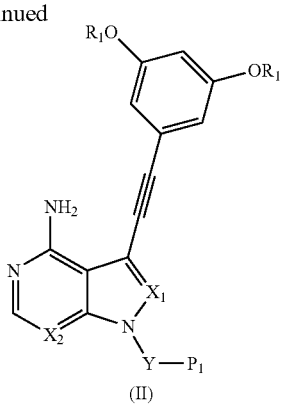

(wherein $L_3$ and $L_4$ are leaving groups; and $R_1$, $X_1$, $X_2$, Y, and $P_1$ are as defined above.)

(Step 5) In this step, the compound of Formula (VII) is subjected to a coupling (Sonogashira) reaction with the compound of Formula (VIII) to produce the compound of Formula (IX). This step can be performed according to a generally known method (see, for example, Chemical Reviews, vol. 107, p. 874, 2007), for example, in the presence of a transition metal catalyst and a base in a solvent that does not adversely affect the reaction.

In Formula (VII), the leaving group represented by $L_3$ is bromine or iodine. The compound of Formula (VII) may be a commercially available product, or can be produced by a known method.

In this step, the compound of Formula (VIII) can be used in an amount of 1 to 10 moles, and preferably 1 to 3 moles, per mole of the compound of Formula (VII).

Examples of transition metal catalysts that can be used in this step include palladium catalysts (e.g., palladium acetate, tris(dibenzylideneacetone)dipalladium, and 1,1'-bis(diphenylphosphino)ferrocene-palladium(II) dichloride dichloromethane complex). If necessary, a ligand (e.g., triphenylphosphine and tri-tert-butylphosphine) can be added and a copper reagent (e.g., copper iodide and copper acetate) can be used as a cocatalyst. The amount of the transition metal catalyst used may vary depending on the type of catalyst. The transition metal catalyst is typically used in an amount of 0.0001 to 1 mole, and preferably 0.01 to 0.5 moles, per mole of the compound of Formula (VII). The amount of the ligand used is typically 0.0001 to 4 moles, and preferably 0.01 to 2 moles, per mole of the compound of Formula (VII). The amount of the cocatalyst used is typically 0.0001 to 4 moles, and preferably 0.01 to 2 moles, per mole of the compound of Formula (VII).

A base may optionally be added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Among them, organic bases such as triethylamine and diisopropylethylamine are preferable. The amount of the base used is typically 0.1 to 50 moles, preferably 1 to 20 moles, per mole of the compound of Formula (VII).

Any reaction solvent that does not adversely affect the reaction can be used. Examples of usable solvents include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethyl sulfoxide, and hexamethylphosphoramide), water, and mixtures thereof. The reaction time is 0.1 to 100 hours, and preferably 0.5 to 24 hours. The reaction temperature is 0° C. to the boiling temperature of the solvent, and preferably 0 to 150° C.

The thus-obtained compound of Formula (IX) can be subjected to the subsequent step after or without isolation and purification by known separation and purification means, such as concentration, vacuum concentration, crystallization, solvent extraction, reprecipitation, and chromatography.

(Step 6) In this step, the compound of Formula (IX) is used with the compound of Formula (X) or (XI) to produce the compound of Formula (II).

When the compound of Formula (X) is used as an alkylating reagent, the compound of Formula (II) can be produced in the presence of a base. In Formula (X), $L_4$ may be a leaving group, such as chlorine, bromine, iodine, a methanesulfonic acid ester, or a p-toluenesulfonic acid ester. The alkylating reagent may be a commercially available product, or can be produced according to a known method. The compound of Formula (X) can be used in an amount of 1 to 10 moles, preferably 1 to 5 moles, per mole of the compound of Formula (IX).

Examples of usable bases include inorganic bases such as sodium hydrogen carbonate, sodium carbonate, potassium carbonate, cesium carbonate, cesium hydroxide, sodium hydride, and potassium hydride; and organic amines such as trimethylamine, triethylamine, tripropylamine, diisopropylethylamine, N-methylmorpholine, pyridine, 4-(N,N-dimethylamino)pyridine, lutidine, and collidine. Such a base can be used in an amount of 1 to 100 moles, preferably 2 to 10 moles, per mole of the compound of Formula (IX).

As the solvent, N,N-dimethylformamide, N,N-dimethylacetamide, dimethyl sulfoxide, tetrahydrofuran, 1,4-dioxane, N-methylpyrrolidin-2-one, acetonitrile, and the like can be used singly, or as a mixture. The reaction time is 0.1 to 100 hours, and preferably 0.5 to 24 hours. The reaction temperature is 0° C. to the boiling temperature of the solvent, and preferably 0 to 100° C.

When the compound of Formula (XI) is used as an alkylating reagent, the compound of Formula (II) can be produced by using a Mitsunobu reaction. This step can be performed according to a generally known method (see, for example, Chemical Reviews, Vol. 109, p. 2551, 2009), for example, in the presence of Mitsunobu reagents and a phosphine reagent in a solvent that does not adversely affect the reaction. This step is performed using the compound of Formula (XI) in an amount of 1 to 10 moles per mole of the compound of Formula (IX).

Examples of Mitsunobu reagents include diethyl azodicarboxylate, diisopropyl azodicarboxylate, and the like. Such Mitsunobu reagents are used in an amount of 1 to 10 moles, and preferably 1 to 5 moles, per mole of the compound of Formula (IX).

Examples of phosphine reagents include triphenylphosphine, tributylphosphine, and the like. Such a phosphine reagent is used in an amount of 1 to 10 moles, and preferably 1 to 5 moles, per mole of the compound of Formula (IX).

Any reaction solvent that does not adversely affect the reaction can be used. Examples of preferable reaction solvents include toluene, benzenetetrahydrofuran, 1,4-dioxane, dimethylformamide, dimethylacetamide, N-methylpyrrolidinone, dimethyl sulfoxide, and mixed solvents thereof.

The reaction temperature is typically −78 to 200° C., and preferably 0 to 50° C. The reaction time is typically 5 minutes to 3 days, and preferably 10 minutes to 10 hours.

The thus-obtained compound of Formula (II) can be utilized after or without isolation and purification by known separation and purification means, such as concentration, vacuum concentration, crystallization, solvent extraction, reprecipitation, and chromatography, to produce Compound (I).

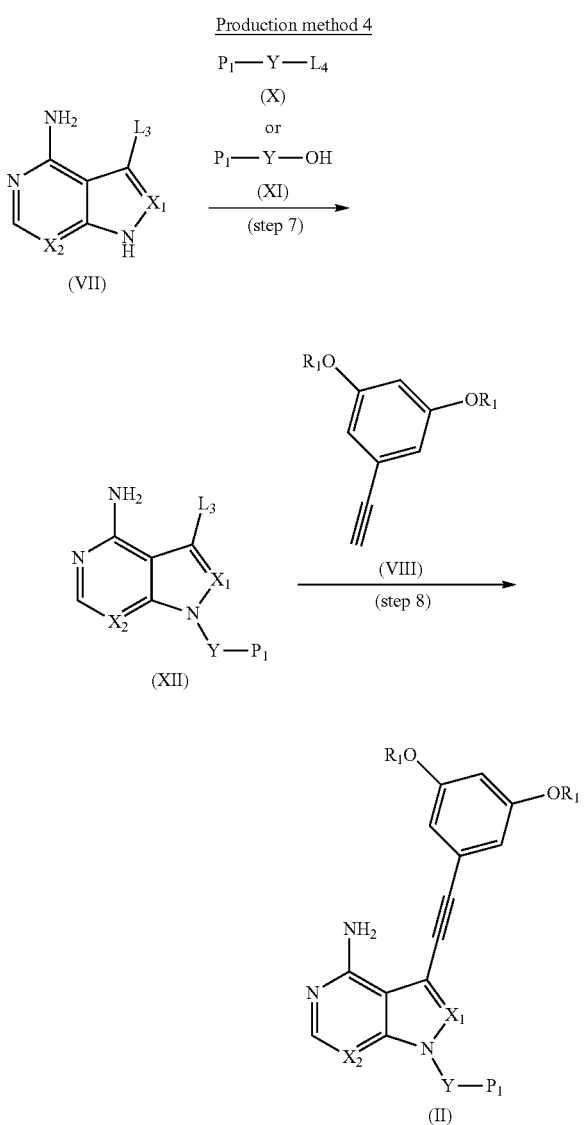

(wherein $L_3$, $L_4$, $X_1$, $X_2$, Y, and $P_1$ are as defined above.)

(Step 7) This step can be performed in a manner similar to step 6.

(Step 8) This step can be performed in a manner similar to step 5.

The compound of Formula (XII) used in the production of Compound (I) can also be produced, for example, by production method 5.

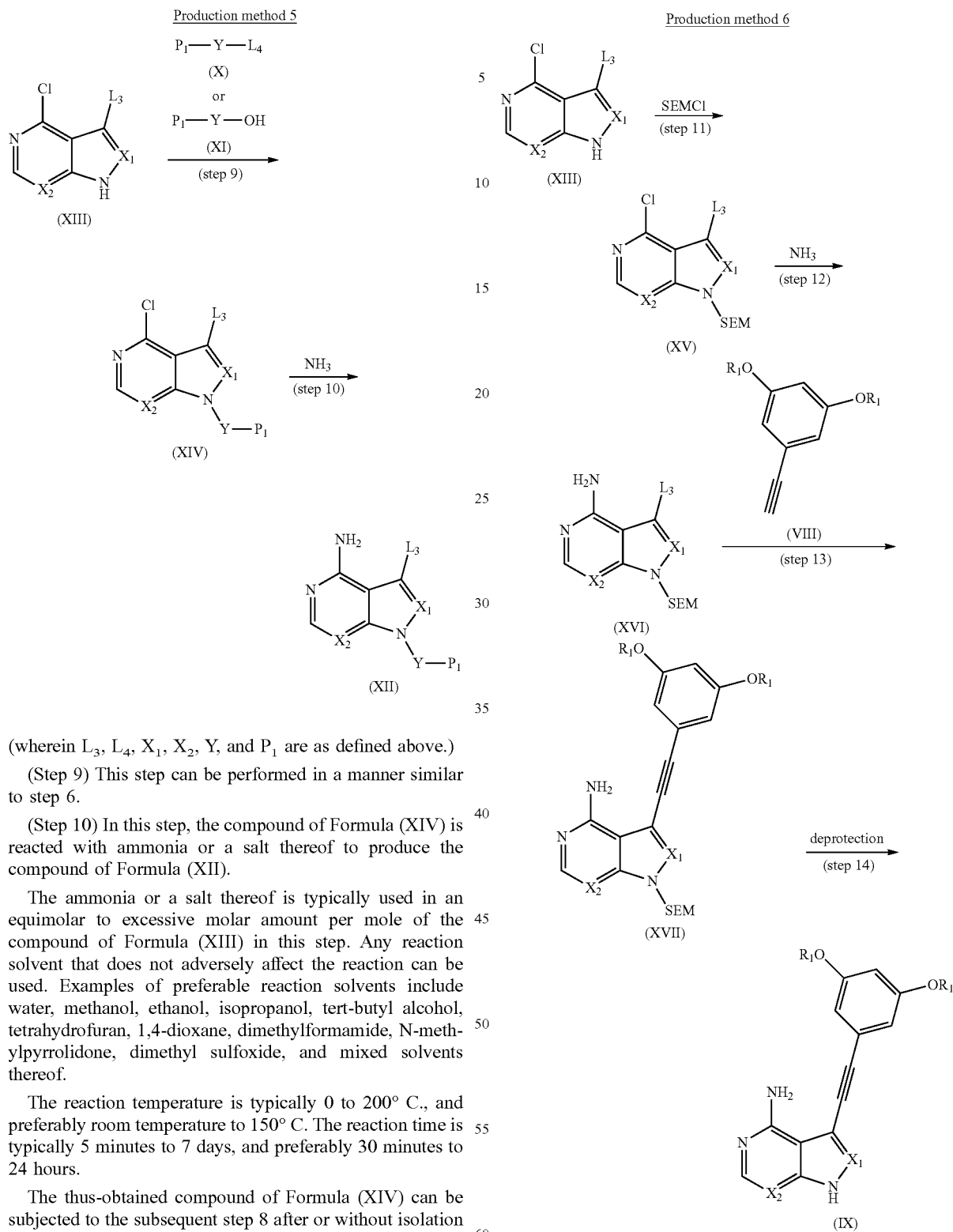

(wherein $L_3$, $L_4$, $X_1$, $X_2$, Y, and $P_1$ are as defined above.)

(Step 9) This step can be performed in a manner similar to step 6.

(Step 10) In this step, the compound of Formula (XIV) is reacted with ammonia or a salt thereof to produce the compound of Formula (XII).

The ammonia or a salt thereof is typically used in an equimolar to excessive molar amount per mole of the compound of Formula (XIII) in this step. Any reaction solvent that does not adversely affect the reaction can be used. Examples of preferable reaction solvents include water, methanol, ethanol, isopropanol, tert-butyl alcohol, tetrahydrofuran, 1,4-dioxane, dimethylformamide, N-methylpyrrolidone, dimethyl sulfoxide, and mixed solvents thereof.

The reaction temperature is typically 0 to 200° C., and preferably room temperature to 150° C. The reaction time is typically 5 minutes to 7 days, and preferably 30 minutes to 24 hours.

The thus-obtained compound of Formula (XIV) can be subjected to the subsequent step 8 after or without isolation and purification by known separation and purification means, such as concentration, vacuum concentration, crystallization, solvent extraction, reprecipitation, and chromatography.

The compound of Formula (IX) used in the production of Compound (I) can also be produced, for example, by production method 6.

(wherein $L_3$, $X_1$, and $X_2$ are as defined above, and SEM is trimethylsilylethoxymethyl.)

(Step 11) In this step, the compound of Formula (XIII) is reacted with SEMCl (trimethylsilylethoxymethylchloride) in the presence of a base to produce the compound of Formula (XV). The compound of Formula (XIII) may be a commercially available product, or can be produced according to a known method.

SEMCl is typically used in an equimolar to excessive molar amount per mole of the compound of Formula (XIII) in this step. Any reaction solvent that does not adversely affect the reaction can be used. Examples of preferable reaction solvents include tetrahydrofuran, 1,4-dioxane, chloroform, methylene chloride, dimethylformamide, N-methylpyrrolidone, and mixed solvents thereof.

Examples of usable bases include organic bases such as triethylamine, diisopropylethylamine, pyridine, and 4-dimethylaminopyridine; and inorganic bases such as sodium hydrogen carbonate, sodium carbonate, potassium carbonate, cesium carbonate, sodium hydroxide, sodium hydride, and potassium tert-butyrate.

Such a base is typically used in an equimolar to excessive molar amount, and preferably 1 to 3 moles, per mole of the compound of Formula (XIII).

The reaction temperature is typically −78 to 50° C., and preferably 0° C. to room temperature. The reaction time is typically 5 minutes to 7 days, and preferably 10 minutes to 24 hours.

The thus-obtained compound of Formula (XV) can be subjected to the subsequent step after or without isolation and purification by known separation and purification means, such as concentration, vacuum concentration, crystallization, solvent extraction, reprecipitation, and chromatography.

(Step 12) This step can be performed in a manner similar to step 10.

The thus-obtained compound of Formula (XVI) can be subjected to the subsequent step after or without isolation and purification by known separation and purification means, such as concentration, vacuum concentration, crystallization, solvent extraction, reprecipitation, and chromatography.

(Step 13) This step can be performed in a manner similar to step 5.

(Step 14) In this step, the compound of Formula (XVII) is deprotected under acidic conditions to produce the compound of Formula (IX). The deprotection can be performed by a known method, such as the method described in Protective Groups in Organic Synthesis, T. W. Greene, John Wiley & Sons (1981); or a method similar thereto.

Examples of usable acids include hydrochloric acid, acetic acid, trifluoroacetic acid, sulfuric acid, methanesulfonic acid, tosic acid, and the like. Such an acid is used in an amount of 1 to 100 moles per mole of the compound of Formula (XVII).

Any solvent that does not adversely affect the reaction can be used. Examples of usable solvents include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane, tetrahydrofuran, and 1,4-dioxane), aprotic polar solvents (e.g., N,N-dimethylformamide, dimethyl sulfoxide, and hexamethylphosphoramide), and mixtures thereof. The reaction time is 0.1 to 100 hours, and preferably 0.5 to 24 hours. The reaction temperature is 0° C. to the boiling temperature of the solvent, and preferably 0 to 100° C.

The thus-obtained compound of Formula (IX) can be used in step 6 after or without isolation and purification by known separation and purification means, such as concentration, vacuum concentration, crystallization, solvent extraction, reprecipitation, and chromatography.

In the above production methods 1 to 6, for functional groups having an active proton, such as amino, imino, hydroxy, carboxy, and amide groups, and indole, protected reagents can be used or a protecting group is introduced into such a functional group according to a usual method, and then the protecting group can be removed in an appropriate step in each production method.

The "protecting group of an amino group or protecting group of an imino group" is not particularly limited insofar as it has a protecting function. Examples of such protecting groups include aralkyl groups such as benzyl, p-methoxybenzyl, 3,4-dimethoxybenzyl, o-nitrobenzyl, p-nitrobenzyl, benzhydryl, trityl, and cumyl; lower alkanoyl groups such as formyl, acetyl, propionyl, butyryl, pivaloyl, trifluoroacetyl, and trichloroacetyl; benzoyl; arylalkanoyl groups such as phenylacetyl and phenoxyacetyl; lower alkoxycarbonyl groups such as methoxycarbonyl, ethoxycarbonyl, propyloxycarbonyl, and tert-butoxycarbonyl; aralkyloxycarbonyl groups such as p-nitrobenzyloxycarbonyl and phenethyloxycarbonyl; lower alkylsilyl groups such as trimethylsilyl and tert-butyldimethylsilyl; tetrahydropyranyl; trimethylsilylethoxymethyl; lower alkylsulfonyl groups such as methylsulfonyl, ethylsulfonyl, and tert-butylsulfonyl; lower alkylsulfinyl groups such as tert-butylsulfinyl; arylsulfonyl groups such as benzenesulfonyl and toluenesulfonyl; and imido groups such as phthalimido. In particular, trifluoroacetyl, acetyl, tert-butoxycarbonyl, benzyloxycarbonyl, trimethylsilylethoxymethyl, cumyl, and the like are preferable.

The "protecting group of a hydroxy group" is not particularly limited insofar as it has a protecting function. Examples of such protecting groups include lower alkyl groups such as methyl, ethyl, propyl, isopropyl, and tert-butyl; lower alkylsilyl groups such as trimethylsilyl and tert-butyldimethylsilyl; lower alkoxymethyl groups such as methoxymethyl and 2-methoxyethoxymethyl; tetrahydropyranyl; trimethylsilylethoxymethyl; aralkyl groups such as benzyl, p-methoxybenzyl, 2,3-dimethoxybenzyl, o-nitrobenzyl, p-nitrobenzyl, and trityl; and acyl groups such as formyl, acetyl, and trifluoroacetyl. In particular, methyl, methoxymethyl, tetrahydropyranyl, trimethylsilylethoxymethyl, tert-butyldimethylsilyl, acetyl, and the like are preferable.

The "protecting group of a carboxy group" is not particularly limited insofar as it has a protecting function. Examples of such protecting groups include lower alkyl groups such as methyl, ethyl, propyl, isopropyl, and tert-butyl; halo-lower-alkyl groups such as 2,2,2-trichloroethyl; lower alkenyl groups such as allyl; trimethylsilylethoxymethyl; and aralkyl groups such as benzyl, p-methoxybenzyl, p-nitrobenzyl, benzhydryl, and trityl. In particular, methyl, ethyl, tert-butyl, allyl, benzyl, p-methoxybenzyl, trimethylsilylethoxymethyl, and the like are preferable.

The "protecting group of a carbonyl group" is not particularly limited insofar as it has a protecting function. Examples of such protecting groups include ketals and acetals, such as ethylene ketal, trimethylene ketal, dimethyl ketal, ethylene acetal, trimethylene acetal, and dimethyl acetal.

The method for removing such a protecting group may vary depending on the type of protecting group, stability of the desired compound (I), etc. For example, the following methods can be used: solvolysis using an acid or a base according to the method disclosed in a publication (Protective Groups in Organic Synthesis, third edition, T. W. Green, John Wiley & Sons (1999)) or a method similar thereto, i.e., a reaction method using, for example, 0.01 moles or a large excess of an acid, preferably trifluoroacetic acid, formic acid, or hydrochloric acid, or an equimolar amount to a large excess of a base, preferably potassium hydroxide or calcium hydroxide; chemical reduction using a metal hydride complex or the like; or catalytic reduction using a palladium-carbon catalyst, Raney nickel catalyst, or the like.

Compound (I) can easily be isolated and purified by usual isolation and purification means. Examples of such means include solvent extraction, recrystallization, preparative reversed-phase high-performance liquid chromatography, column chromatography, preparative thin-layer chromatography, and the like.

When Compound (I) has isomers such as optical isomers, stereoisomers, positional isomers, and rotational isomers, any of the isomers and mixtures thereof are included within the scope of Compound (I). For example, when Compound (I) has optical isomers, optical isomers separated from a racemic mixture are also included within the scope of Compound (I). Each of these isomers can be obtained as a single compound by known synthesis and separation means (e.g., concentration, solvent extraction, column chromatography, and recrystallization).

Compound (I) or a salt thereof may be crystalline. A single crystal form thereof and a polymorphic mixture thereof are both included within the scope of Compound (I) or a salt thereof. These crystals can be produced by crystallization according to a crystallization method known per se in the art. Compound (I) or a salt thereof may be a solvate (e.g., a hydrate) or a non-solvate. Any of such forms are included within the scope of Compound (I) or a salt thereof. Compounds labeled with an isotope (such as $^3$H, $^{14}$C, $^{35}$S, or $^{125}$I) are also included within the scope of Compound (I) or a salt thereof.

A prodrug of Compound (I) or a salt thereof refers to a compound that can be converted to Compound (I) or a salt thereof through a reaction with an enzyme, gastric acid, or the like under physiological conditions in vivo, i.e., a compound that can be converted to Compound (I) or a salt thereof by enzymatic oxidation, reduction, hydrolysis, or the like; or a compound that can be converted to Compound (I) or a salt thereof by hydrolysis with gastric acid or the like. Further, the prodrug of Compound (I) or a salt thereof may be compounds that can be converted to Compound (I) or a salt thereof under physiological conditions, such as those described in "Iyakuhin no Kaihatsu [Development of Pharmaceuticals]," Vol. 7, Molecular Design, published in 1990 by Hirokawa Shoten Co., pp. 163-198.

The salt of Compound (I) refers to a common salt used in the field of organic chemistry. Examples of such salts include base addition salts to carboxyl when the compound has carboxyl, and acid addition salts to an amino or basic heterocyclic group when the compound has an amino or basic heterocyclic group.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

Compound (I) or a salt thereof has excellent FGFR inhibitory activity, and is useful as an antitumor agent. Further, Compound (I) or a salt thereof has excellent selectivity toward FGFR, and has advantageously fewer side effects caused by other kinases. Although the target cancer is not particularly limited, examples thereof include head and neck cancer, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, blood cancer, multiple myeloma, skin cancer, brain tumor, and mesothelioma. Preferably, the target cancer is blood cancers such as B-cell lymphoma, chronic lymphocytic leukemia, peripheral T-cell lymphoma, myelodysplastic syndrome, acute myeloid leukemia, and acute lymphocytic leukemia.

When Compound (I) or a salt thereof is used as a pharmaceutical preparation, a pharmaceutical carrier can be added, if required, thereby forming a suitable dosage form according to prevention and treatment purposes. Examples of the dosage form include oral preparations, injections, suppositories, ointments, patches, and the like. Of these, oral preparations are preferable. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations can be prepared as follows. An excipient, optionally together with a binder, disintegrant, lubricant, colorant, taste-masking or flavoring agent, etc., is added to Compound (I) or a salt thereof to produce tablets, coated tablets, granules, powders, capsules, or the like, using an ordinary method.

When an injection agent is prepared, a pH adjuster, buffer, stabilizer, isotonizing agent, local anesthetic, etc., may be added to Compound (I) or a salt thereof; and the mixture may be processed into a subcutaneous, intramuscular, or intravenous injection according to an ordinary method.

The amount of Compound (I) or a salt thereof to be contained in such a dosage unit form varies depending on the condition of the patient, the dosage form, etc. The desirable amount in dosage unit form is generally 0.05 to 1,000 mg in the case of an oral preparation, 0.01 to 500 mg in the case of an injection, and 1 to 1,000 mg in the case of a suppository.

Moreover, the daily dose of the medicine having the above-described dosage form may vary depending on the condition, body weight, age, and sex of a patient, etc., and cannot be generalized. Usually, the daily dose is preferably 0.05 to 5000 mg per adult (body weight: 50 kg) per day, and more preferably 0.1 to 1000 mg per adult (body weight: 50 kg) per day. Such a dose of the medicine is preferably administered in one dose, or in two to three divided doses, per day.

EXAMPLES

The present invention is explained in more detail below with reference to Examples and Test Examples; however, the scope of the present invention is not limited to these Examples.

In the Examples, commercially available reagents were used, unless otherwise specified. Purif-Pack (registered trademark) SI, produced by Moritex Corp.; KP-Sil (registered trademark) Silica prepacked column, produced by Biotage; or HP-Sil (registered trademark) Silica prepacked column, produced by Biotage was used as the silica gel column chromatography. Purif-Pack (registered trademark) NH, produced by Moritex Corp; or KP-NH (registered trademark) prepacked column, produced by Biotage was used as the basic silica gel column chromatography. Kieselgel TM 60F 254, Art. 5744, produced by Merck, or $NH_2$ Silica Gel 60F254 Plate, produced by Wako, was used as the preparative thin-layer chromatography. NMR spectrum was measured by using AL400 (400 MHz; produced by JEOL), Mercury 400 (400 MHz; produced by Agilent Technologies, Inc.) spectrometer, or Inova 400 (400 MHz; produced by Agilent Technologies, Inc.) model spectrometer equipped with an OMNMR probe (produced by Protasis). When its deuterated solvent contains tetramethylsilane, the tetramethylsilane was used as the internal reference; and when tetramethylsilane is not contained, an NMR solvent was used as the reference. All the delta values are shown by ppm. The microwave reaction was performed using Discover S-class, produced by CEM Corporation.

The LCMS spectrum was measured using an Acquity SQD (quadrupole), produced by Waters Corporation, under the following conditions.
Column: YMC-Triart C18, 2.0×50 mm, 1.9 μm (produced by YMC)
MS detection: ESI positive
UV detection: 254 and 210 nm
Column flow rate: 0.5 mL/min
Mobile phase: Water/acetonitrile (0.1% formic acid)
Injection volume: 1 μL

TABLE 1

| Gradient | | |
|---|---|---|
| Time (min) | Water | Acetonitrile |
| 0 | 95 | 5 |
| 0.1 | 95 | 5 |
| 2.1 | 5 | 95 |
| 3.0 | STOP | |

Preparative reversed-phase HPLC purification was performed using a preparative separation system available from Waters Corporation, under the following conditions.
Column: Connected YMC-Actus Triart C18, 20×50 mm, 5 μm (produced by YMC) and YMC-Actus Triart C18, 20×10 mm, 5 μm (produced by YMC).
UV detection: 254 nm
MS detection: ESI positive
Column flow rate: 25 mL/min
Mobile phase: Water/acetonitrile (0.1% formic acid)
Injection volume: 0.1 to 0.5 mL Each symbol stands for the following.
s: Singlet
d: Doublet
t: Triplet
q: Quartet
dd: Double Doublet
dt: Double Triplet
td: Triple Doublet
tt: Triple Triplet
ddd: Double Double Doublet
ddt: Double Double Triplet
dtd: Double Triple Doublet
tdd: Triple Double Doublet
m: Multiplet
br: Broad
brs: Broad Singlet
DMSO-d: Deuterated dimethyl sulfoxide
$CDCl_3$: Deuterated chloroform
$CD_3OD$: Deuterated methanol
THF: Tetrahydrofuran
DMF: N,N-dimethylformamide
NMP: 1-Methyl-2-pyrrolidinone
DMSO: Dimethyl sulfoxide
TFA: Trifluoroacetic acid
SEMCl: 2-(Trimethylsilyl)ethoxymethyl chloride
$PdCl_2$(dppf) $CH_2Cl_2$: 1,1'-bis(diphenylphosphino) ferrocene-palladium (II) dichloride-dichloromethane complex
WSC: 1-(3-Dimethylaminopropyl)-3-ethylcarbodiimide hydrochloride
HOBt: 1-Hydroxybenzotriazole monohydrate
HATU: O-(7-azabenzotriazol-1-yl)-N,N,N',N'-tetramethyluronium hexafluorophosphate
HBTU: O-benzotriazol-N,N,N',N'-tetramethyluronium hexafluorophosphate
DIAD: Diisopropyl azodicarboxylate
TBAF: Tetrabutylammoniumfluoride
DIPEA: Diisopropylethylamine
$Boc_2O$: Di-tert-butyl dicarbonate
DMAP: Dimethylaminopyridine Example 1

Synthesis of 1-(3-(4-amino-3-((3,5-dimethoxyphenyl)ethynyl)-1H-pyrazolo[3,4-d]pyrimidin-1-yl)pyrrolidin-1-yl)prop-2-en-1-one (compound of Example 1)

(Step 1) Synthesis of 3-((3,5-dimethoxyphenyl) ethynyl)-1H-pyrazolo[3,4-d]pyrimidin-4-amine $PdCl_2$ (dppf) $CH_2Cl_2$ (163 mg) was added to a mixture of 3-iodo-1H-pyrazolo[3,4-d]pyrimidin-4-amine (520 mg) synthesized by the method disclosed in WO 2007/126841, 1-ethynyl-3,5-dimethoxybenzene (504 mg), copper (I) iodide (57.3 mg), and triethylamine (0.56 ml) in DMF (10 ml). After nitrogen purging, the resulting mixture was stirred at 90° C. for 6 hours. Chloroform and water were added to the reaction mixture to separate the organic layer. After being washed with a saturated sodium chloride solution, the organic layer was dried over anhydrous sodium sulfate, and the solvent was then distilled off under reduced pressure. The resulting residue was purified by basic silica gel column chromatography (developing solvent: chloroform/methanol) to obtain the title compound as a dark-brown solid (120 mg). Physical properties: m/z[M+H]$^+$ 296.0.

(Step 2) Synthesis of tert-butyl 3-(methylsulfonyloxy)pyrrolidine-1-carboxylate

N-Boc-3-pyrrolidinol (1000 mg) was dissolved in chloroform (20 ml). Triethylamine (1.15 ml) and methanesulfonyl chloride (498 µl) were added thereto at 0° C. After stirring at room temperature for 1.0 hour, ethyl acetate and water were added thereto to separate the organic layer. After being washed with a saturated aqueous sodium bicarbonate solution, a saturated aqueous ammonium chloride solution and water, the organic layer was dried over anhydrous sodium sulfate. The solvent was distilled off under reduced pressure to obtain the title compound as a colorless, oily compound (1.2 g). Physical properties: m/z[M+H]$^+$ 266.1.

(Step 3) Synthesis of tert-butyl 3-(4-amino-3-((3,5-dimethoxyphenyl)ethynyl)-1H-pyrazolo[3,4-d]pyrimidin-1-yl)pyrrolidine-1-carboxylate A suspension of 3-((3,5-dimethoxyphenyl)ethynyl)-1H-pyrazolo[3,4-d]pyrimidin-4-amine (62 mg) obtained in Step 1, tert-butyl 3-(methylsulfonyloxy)pyrrolidine-1-carboxylate (217 mg) obtained in Step 2, and potassium carbonate (221 mg) in DMF (2.0 ml) was stirred at 70° C. for 1 hour. Ethyl acetate and water were added thereto to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a light-yellow, amorphous substance (36.2 mg). Physical properties: m/z[M+H]$^+$ 465.1.

(Step 4) Synthesis of Compound of Example 1

4N-Hydrochloric acid/1,4-dioxane (4 ml) was added to the tert-butyl 3-(4-amino-3-((3,5-dimethoxyphenyl)ethynyl)-1H-pyrazolo[3,4-d]pyrimidin-1-yl)pyrrolidine-1-carboxylate (32 mg) obtained in Step 3, and the mixture was stirred at room temperature for 1.5 hours. After distilling the solvent of the resulting reaction mixture off under reduced pressure, toluene azeotropic distillation was subsequently performed to obtain a crude product of 3-((3,5-dimethoxyphenyl)ethynyl)-1-(pyrrolidin-3-yl)-1H-pyrazolo[3,4-d]pyrimidin-4-amine (32 mg). Chloroform (2.0 ml) and triethylamine (20 µl) were added to a portion of the resulting crude product (12 mg). After cooling to 0° C., acrylic chloride (2.3 µl) dissolved in chloroform (100 µl) was added thereto, and the mixture was stirred at room temperature for 10 minutes. After halting the reaction using a saturated aqueous sodium bicarbonate solution, the resulting product was extracted with ethyl acetate. After drying the result over anhydrous sodium sulfate, the solvent was distilled off under reduced pressure. The resulting residue was purified by silica gel column chromatography (developing solvent: ethyl acetate/methanol) to obtain the title compound as a white solid (6.5 mg). Table 1 shows the physical properties thereof.

Example 2

Synthesis of (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one (compound of Example 2)

(Step 1) Synthesis of (R)-tert-butyl 3-(methylsulfonyloxy) pyrrolidine-1-carboxylate (R)—N-Boc-3-pyrrolidinol (935 mg) was dissolved in chloroform (15 ml), and triethylamine (1.04 ml) and methanesulfonyl chloride (467 µl) were added thereto at 0° C.

After stirring at room temperature for 1.5 hours, ethyl acetate and water were added thereto to separate the organic layer. After being washed with a saturated aqueous sodium bicarbonate solution, a saturated aqueous ammonium chloride solution and water, the organic layer was dried over anhydrous sodium sulfate, and the solvent was distilled off under reduced pressure to obtain the title compound as a colorless, oily compound (1.1 g). Physical properties: m/z [M+H]$^+$ 266.1.

(Step 2) Synthesis of (S)-tert-butyl 3-(4-amino-3-((3,5-dimethoxyphenyl)ethynyl)-1H-pyrazolo[3,4-d]pyrimidin-1-yl)pyrrolidine-1-carboxylate A suspension of 3-((3,5-dimethoxyphenyl)ethynyl)-1H-pyrazolo[3,4-d]pyrimidin-4-amine (334 mg) obtained in Example 1 (Step 1), (R)-tert-butyl 3-(methylsulfonyloxy) pyrrolidine-1-carboxylate (379 mg) obtained in (Step 1) above, and potassium carbonate (391 mg) in DMF (4.0 ml) was stirred at 70° C. for 3 hours. Ethyl acetate and water were added thereto to separate the organic layer. The organic layer was dried over anhydrous sodium sulfate, and the solvent was then distilled off under reduced pressure. The resulting residue was purified by basic silica gel column chromatography (developing solvent: hexane/ethyl acetate) to obtain the title compound as a light-yellow, amorphous substance (149 mg). Physical properties: m/z[M+H]$^+$ 465.1.

(Step 3) Synthesis of Compound of Example 2

In accordance with Example 1 (Step 4), except that (S)-tert-butyl 3-(4-amino-3-((3,5-dimethoxyphenyl)ethynyl)-1H-pyrazolo[3,4-d]pyrimidin-1-yl)pyrrolidine-1-carboxylate obtained in (Step 2) above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of (S)-3-((3,5-dimethoxyphenyl)ethynyl)-1-(pyrrolidin-3-yl)-1H-pyrazolo[3,4-d]pyrimidin-4-amine was obtained by removing a Boc group under acidic conditions. Thereafter, amidation was conducted to obtain the title compound as a white solid. Table 1 shows the physical properties thereof.

Example 3

Synthesis of 1-(3-(4-amino-3-((3,5-dimethoxyphenyl)ethynyl)-1H-pyrazolo[3,4-d]pyrimidin-1-yl)pyrrolidin-1-yl)but-2-en-1-one (compound of Example 3)

In accordance with Example 1 (Step 4), except that 2-butenoyl chloride was used in place of acrylic chloride, the title compound was obtained as a white solid. Table 1 shows the physical properties thereof.

Example 4

Synthesis of (S)-1-(3-(4-amino-3-((3,5-dimethoxyphenyl)ethynyl)-1H-pyrazolo[3,4-d]pyrimidin-1-yl) pyrrolidin-1-yl)-4-(dimethylamino)but-2-en-1-one (compound of Example 4)

The crude product (5.6 mg) of (S)-3-((3,5-dimethoxyphenyl)ethynyl)-1-(pyrrolidin-3-yl)-1H-pyrazolo[3,4-d]pyrimidin-4-amine obtained in Example 2 as an intermediate, 4-(dimethylamino)but-2-enoic acid hydrochloride (6.3 mg), and HATU (15 mg) were dissolved in DMF (1.0 ml). DIPEA (50 µl) was added thereto, followed by stirring overnight. Chloroform and water were added to the reaction mixture to separate the organic layer. After being washed with a saturated sodium chloride solution, the organic layer was dried over anhydrous sodium sulfate, and the solvent was then distilled off under reduced pressure. The resulting residue was purified by preparative reversed-phase HPLC purification (water/acetonitrile (0.1% formic acid)) to obtain the title compound as a colorless, amorphous substance (2.3 mg). Table 1 shows the physical properties thereof.

Example 5

Synthesis of (S)-1-(3-(4-amino-3-((3,5-dimethoxyphenyl)ethynyl)-1H-pyrazolo[3,4-d]pyrimidin-1-yl)pyrrolidin-1-yl)prop-2-yn-1-one (compound of Example 5)

The crude product (16 mg) of (S)-3-((3,5-dimethoxyphenyl)ethynyl)-1-(pyrrolidin-3-yl)-1H-pyrazolo[3,4-d]pyrimidin-4-amine obtained in Example 2 as an intermediate, 3-(trimethylsilyl)propionic acid (10 mg), HATU (28 mg) were dissolved in DMF (0.5 ml). DIPEA (31 µl) was added thereto, followed by stirring overnight. Ethyl acetate and a saturated aqueous sodium bicarbonate solution were added to the reaction mixture to separate the organic layer. After drying the organic layer over anhydrous sodium sulfate, the solvent was distilled off under reduced pressure. The resulting residue was purified by silica gel column chromatography (developing solvent: ethyl acetate/methanol) to obtain the title compound as a white solid (0.7 mg). Table 2 shows the physical properties thereof.

Example 6

Synthesis of (S)-1-(3-(4-amino-3-((3,5-dimethoxyphenyl)ethynyl)-1H-pyrazolo[3,4-d]pyrimidin-1-yl)pyrrolidin-1-yl)-2-fluoroprop-2-en-1-one (compound of Example 6)

In accordance with Example 4, except that 2-fluoroacrylic acid was used in place of 4-(dimethylamino)but-2-enoic acid hydrochloride, the title compound was obtained as a colorless, amorphous substance. Table 2 shows the physical properties thereof.

Example 7

Synthesis of (S)-1-(3-(4-amino-3-((3,5-dimethoxyphenyl)ethynyl)-1H-pyrazolo[3,4-d]pyrimidin-1-yl)pyrrolidin-1-yl)-2-(pyrrolidin-1-ylmethyl)prop-2-en-1-one (compound of Example 7)

In accordance with Example 4, except that 2-(pyrrolidin-1-ylmethyl)acetic acid (Synth. Commun. 1995, 641) was used in place of 4-(dimethylamino)but-2-enoic acid hydrochloride, the title compound was obtained as a colorless, amorphous substance. Table 2 shows the physical properties thereof.

Example 8

Synthesis of (S)-1-(3-(4-amino-3-((3,5-diethoxyphenyl)ethynyl)-1H-pyrazolo[3,4-d]pyrimidin-1-yl)pyrrolidin-1-yl)prop-2-en-1-one (compound of Example 8)

(Step 1) Synthesis of 1,3-diethoxy-5-ethynylbenzene

Carbon tetrabromide (4.78 g) was dissolved in dichloroethane (14 mL), and triphenylphosphine (7.56 g) was added thereto at 0° C. After stirring at 0° C. for 5 minutes, a solution of 3,5-diethoxybenzaldehyde (1.40 g) in dichloromethane (7 mL) was added thereto, followed by stirring for 20 minutes. Without performing further treatment, the reaction mixture was purified by silica gel chromatography (developing solvent: hexane/ethyl acetate) to obtain 1-(2,2-dibromovinyl)-3,5-diethoxybenzene. The obtained compound was used for the subsequent reaction without further purification. The compound obtained above was dissolved in THF (30 mL). A 1.63 M n-butyllithium solution in hexane (10.5 mL) was added thereto at −78° C. The resulting mixture was stirred at −78° C. for 30 minutes. After adding a saturated aqueous ammonium chloride solution, the reaction mixture was subjected to extraction using ethyl acetate. The resulting organic layer was washed with a saturated sodium chloride solution, and the organic layer was then dried over anhydrous sodium sulfate. The solvent was concentrated under reduced pressure. The resulting residue was purified by silica gel column chromatography (developing solvent: hexane/ethyl acetate) to obtain the title compound as a colorless, oily substance (1.31 g). Physical properties: m/z [M+H]$^+$ 191.0.

(Step 2) In accordance with Example 1, except that 1,3-diethoxy-5-ethynylbenzene obtained in Step 1 was used in place of 1-ethynyl-3,5-dimethoxybenzene, the title compound was obtained as a colorless, amorphous substance. Table 2 shows the physical properties thereof.

Example 9

Synthesis of 1-(3-(4-amino-3-((3,5-dimethoxyphenyl)ethynyl)-1H-pyrazolo[3,4-d]pyrimidin-1-yl)azetidin-1-yl)prop-2-en-1-one (compound of Example 9)

(Step 1) Synthesis of tert-butyl 3-(methylsulfonyloxy)azetidine-1-carboxylate

N-Boc-3-hydroxyazetidine (1.73 g) was dissolved in chloroform (20 ml). Triethylamine (2.09 ml) and methanesulfonyl chloride (856 µl) were added thereto at 0° C. After stirring at room temperature for 0.5 hours, ethyl acetate and water were added thereto to separate the organic layer. After being washed with a saturated aqueous sodium bicarbonate solution, a saturated aqueous ammonium chloride solution, and water, the organic layer was dried over anhydrous sodium sulfate. The solvent was then distilled off under reduced pressure to obtain the title compound as a colorless, oily compound (2.32 g). Physical properties: m/z[M+H]$^+$ 252.0.

(Step 2) Synthesis of tert-butyl 3-(4-amino-3-iodo-1H-pyrazolo[3,4-d]pyrimidin-1-yl)azetidine-1-carboxylate A suspension of tert-butyl 3-(methylsulfonyloxy)azetidine-1-carboxylate (1.32 g) obtained in Step 1 above, 3-iodo-1H-pyrazolo[3,4-d]pyrimidin-4-amine (1.37 g), and cesium carbonate (3.47 g) in DMF (10 ml) was stirred at 90° C. for 10 hours. Ethyl acetate and water were added thereto to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a light-yellow amorphous substance (482 mg). Physical properties: m/z[M+H]⁺ 417.0.

(Step 3) Synthesis of tert-butyl 3-(4-amino-3-((3,5-dimethoxyphenyl)ethynyl)-1H-pyrazolo[3,4-d]pyrimidin-1-yl)azetidine-1-carboxylate PdCl$_2$(dppf) CH$_2$Cl$_2$ (39 mg) was added to a mixture of tert-butyl 3-(4-amino-3-iodo-1H-pyrazolo[3,4-d]pyrimidin-1-yl)azetidine-1-carboxylate (200 mg) obtained in Step 2 above, 1-ethynyl-3,5-dimethoxybenzene (117 mg), copper (I) iodide (14 mg), and triethylamine (0.5 ml) in THF (5 ml). After nitrogen purging, the resulting mixture was stirred at 80° C. for 1.5 hours. Ethyl acetate and water were added to the reaction mixture to separate the organic layer. After being washed with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (185 mg). Physical properties: m/z[M+H]⁺ 451.1.

(Step 4) Synthesis of Compound of Example 9

In accordance with Example 1 (Step 4), except that tert-butyl 3-(4-amino-3-iodo-1H-pyrazolo[3,4-d]pyrimidin-1-yl)azetidine-1-carboxylate obtained in Step 3 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of 1-(azetidin-3-y)-3-((3,5-dimethoxyphenyl)ethynyl)-1H-pyrazolo[3,4-d]pyrimidin-4-amine was obtained by removing a Boc group under acidic conditions. Thereafter, amidation was conducted to obtain the title compound as a white solid. Table 2 shows the physical properties thereof.

Example 10

Synthesis of 1-(3-(4-amino-3-((3,5-dimethoxyphenyl)ethynyl)-1H-pyrazolo[3,4-d]pyrimidin-1-yl)azetidin-1-yl)-4-hydroxybut-2-yn-1-one (compound of Example 10)

A crude product (6.0 mg) of 1-(azetidin-3-yl)-3-((3,5-dimethoxyphenyl)ethynyl)-1H-pyrazolo[3,4-d]pyrimidin-4-amine obtained in Example 9 as an intermediate, 4-hydroxybut-2-ynoic acid (3.7 mg), and HATU (11 mg) were dissolved in DMF (1.0 ml). DIPEA (30 μl) was added thereto, followed by stirring overnight.

Chloroform and water were added to the reaction mixture to separate the organic layer. After being washed with a saturated sodium chloride solution, the organic layer was dried over anhydrous sodium sulfate, and the solvent was distilled off under reduced pressure. The resulting residue was purified by preparative reversed-phase HPLC purification (water/acetonitrile (0.1% formic acid)) to obtain the title compound as a colorless, amorphous substance (1.4 mg). Table 3 shows the physical properties thereof.

Example 11

Synthesis of 1-(3-(4-amino-3-((3,5-dimethoxyphenyl)ethynyl)-1H-pyrazolo[3,4-d]pyrimidin-1-yl)azetidin-1-yl)-4-hydroxy-4-methylpent-2-yn-1-one (compound of Example 11)

In accordance with Example 10, except that 4-hydroxy-4-methylpent-2-ynoic acid was used in place of 4-hydroxybut-2-ynoic acid, the title compound was obtained as a colorless, amorphous substance. Table 3 shows the physical properties thereof.

Example 12

Synthesis of 1-(3-(4-amino-3-((3,5-dimethoxyphenyl)ethynyl)-1H-pyrazolo[3,4-d]pyrimidin-1-yl)azetidin-1-yl)-4-(dimethylamino)but-2-en-1-one (compound of Example 12)

In accordance with Example 10, except that 4-(dimethylamino)but-2-enoic acid hydrochloride was used in place of 4-hydroxybut-2-ynoic acid, the title compound was obtained as a colorless, amorphous substance. Table 3 shows the physical properties thereof.

Example 13

Synthesis of 1-(3-(4-amino-3-((3,5-dimethoxyphenyl)ethynyl)-1H-pyrazolo[3,4-d]pyrimidin-1-yl)azetidin-1-yl)-4-(cyclopropylamino)but-2-en-1-one (compound of Example 13)

(Step 1) Synthesis of 4-bromobut-2-enoyl chloride Thionyl chloride (3.0 ml) was added to 4-bromocrotonic acid (329 mg), and the mixture was stirred at 80° C. for 5 hours. The reaction mixture was concentrated under reduced pressure, and toluene azeotropic distillation was subsequently performed to obtain the title compound as a crude product (394 mg).

(Step 2) Synthesis of 1-(3-(4-amino-3-((3,5-dimethoxyphenyl)ethynyl)-1H-pyrazolo[3,4-d]pyrimidin-1-yl)azetidin-1-yl)-4-bromobut-2-en-1-one A crude product (140 mg) of 1-(azetidin-3-yl)-3-((3,5-dimethoxyphenyl)ethynyl)-1H-pyrazolo[3,4-d]pyrimidin-4-amine obtained in Example 9 as an intermediate was suspended in THF (4.5 ml), DIPEA (178 μl) was added thereto, and the mixture was cooled to 0° C. A solution of 4-bromobut-2-enoyl chloride (66 mg) obtained in Step 1 above in THF (0.5 ml) was added to the mixture dropwise and stirred at room temperature for 15 minutes. After halting the reaction using a saturated aqueous sodium bicarbonate solution, the resulting product was extracted with ethyl acetate. After drying the result over anhydrous sodium sulfate, the solvent was distilled off under reduced pressure to obtain the title compound as a crude product (160 mg). Physical properties: m/z[M+H]⁺ 497.0, 499.0.

(Step 3) Synthesis of Compound of Example 13

The crude product (12 mg) of 1-(3-(4-amino-3-((3,5-dimethoxyphenyl)ethynyl)-1H-pyrazolo[3,4-d]pyrimidin-1-yl)azetidin-1-yl)-4-bromobut-2-en-1-one obtained in Step 2 above was dissolved in DMF (0.5 ml). Cyclopropylamine (5 μl) and DIPEA (10 μl) were added thereto, and the mixture was stirred at room temperature for 1 hour. After concentrating under reduced pressure, the resulting residue was purified by preparative reversed-phase HPLC purification (water/acetonitrile (0.1% formic acid)) to obtain the title compound as a colorless, amorphous substance (3.4 mg). Table 3 shows the physical properties thereof.

Example 14

Synthesis of 1-(3-(4-amino-3-((3,5-dimethoxyphenyl)ethynyl)-1H-pyrazolo[3,4-d]pyrimidin-1-yl)azetidin-1-yl)-4-(isopropylamino)but-2-en-1-one (compound of Example 14)

In accordance with Example 13 (Step 3), except that isopropylamine was used in place of cyclopropylamine, the title compound was obtained as a colorless, amorphous substance. Table 4 shows the physical properties thereof.

Example 15

Synthesis of 1-(3-(4-amino-3-((3,5-dimethoxyphenyl)ethynyl)-1H-pyrazolo[3,4-d]pyrimidin-1-yl)azetidin-1-yl)-4-(ethyl(methyl) amino)but-2-en-1-one (compound of Example 15)

In accordance with Example 13 (Step 3), except that ethylmethylamine was used in place of cyclopropylamine, the title compound was obtained as a colorless, amorphous substance. Table 4 shows the physical properties thereof.

Example 16

Synthesis of 1-(3-(4-amino-3-((3,5-dimethoxyphenyl)ethynyl)-1H-pyrazolo[3,4-d]pyrimidin-1-yl)azetidin-1-yl)-4-(cyclobutylamino)but-2-en-1-one (compound of Example 16)

In accordance with Example 13 (Step 3), except that cyclobutylamine was used in place of cyclopropylamine, the title compound was obtained as a colorless, amorphous substance. Table 4 shows the physical properties thereof.

Example 17

Synthesis of 1-(3-(4-amino-3-((3,5-dimethoxyphenyl)ethynyl)-H-pyrazolo[3,4-d]pyrimidin-1-yl)azetidin-1-yl)-4-(diethylamino)but-2-en-1-one (compound of Example 17)

In accordance with Example 13 (Step 3), except that diethylamine was used in place of cyclopropylamine, the title compound was obtained as a colorless, amorphous substance. Table 5 shows the physical properties thereof.

Example 18

Synthesis of 1-(3-(4-amino-3-((3,5-dimethoxyphenyl)ethynyl)-1H-pyrazolo[3,4-d]pyrimidin-1-yl)azetidin-1-yl)-4-(tert-butylamino)but-2-en-1-one (compound of Example 18)

In accordance with Example 13 (Step 3), except that tert-butylamine was used in place of cyclopropylamine, the title compound was obtained as a colorless, amorphous substance. Table 5 shows the physical properties thereof.

Example 19

Synthesis of 1-(3-(4-amino-3-((3,5-dimethoxyphenyl)ethynyl)-1H-pyrazolo[3,4-d]pyrimidin-1-yl)azetidin-1-yl)-4-(isopropyl(methyl) amino)but-2-en-1-one (compound of Example 19)

In accordance with Example 13 (Step 3), except that isopropylmethylamine was used in place of cyclopropylamine, the title compound was obtained as a colorless, amorphous substance. Table 5 shows the physical properties thereof.

Example 20

Synthesis of 1-(3-(4-amino-3-((3,5-dimethoxyphenyl)ethynyl)-1H-pyrazolo[3,4-d]pyrimidin-1-yl)azetidin-1-yl)-4-(piperidin-1-yl)but-2-en-1-one (compound of Example 20)

In accordance with Example 13 (Step 3), except that piperidine was used in place of cyclopropylamine, the title compound was obtained as a colorless, amorphous substance. Table 5 shows the physical properties thereof.

Example 21

Synthesis of 1-(3-(4-amino-3-((3,5-dimethoxyphenyl)ethynyl)-1H-pyrazolo[3,4-d]pyrimidin-1-yl)azetidin-1-yl)-4-morpholinobut-2-en-1-one (compound of Example 21)

In accordance with Example 13 (Step 3), except that morpholine was used in place of cyclopropylamine, the title compound was obtained as a colorless, amorphous substance. Table 6 shows the physical properties thereof.

Example 22

Synthesis of (S)-1-(3-(4-amino-3-((3,5-dimethoxyphenyl)ethynyl)-1H-pyrazolo[3,4-d]pyrimidin-1-yl) azetidin-1-yl)-4-(3-fluoropyrrolidin-1-yl)but-2-en-1-one In accordance with Example 13 (Step 3), except that (S)-3-fluoropyrrolidine was used in place of cyclopropylamine, the title compound was obtained as a colorless, amorphous substance. Table 6 shows the physical properties thereof.

Example 23

Synthesis of (R)-1-(3-(4-amino-3-((3,5-dimethoxyphenyl)ethynyl)-1H-pyrazolo[3,4-d]pyrimidin-1-yl) azetidin-1-yl)-4-(3-fluoropyrrolidin-1-yl)but-2-en-1-one In accordance with Example 13 (Step 3), except that (R)-3-fluoropyrrolidine was used in place of cyclopropylamine, the title compound was obtained as a colorless, amorphous substance. Table 6 shows the physical properties thereof.

Example 24

Synthesis of 1-(3-(4-amino-3-((3,5-diethoxyphenyl) ethynyl)-1H-pyrazolo[3,4-d]pyrimidin-1-yl)azetidin-1-yl)prop-2-en-1-one (compound of Example 24)

In accordance with Example 9, except that 1,3-diethoxy-5-ethynylbenzene was used in place of 1-ethynyl-3,5-dimethoxybenzene, the title compound was obtained as a colorless, amorphous substance. Table 7 shows the physical properties thereof.

Example 25

Synthesis of 1-(3-(4-amino-3-((3,5-diethoxyphenyl) ethynyl)-1H-pyrazolo[3,4-d]pyrimidin-1-yl)azetidin-1-yl)-4-(dimethylamino)but-2-en-1-one (compound of Example 25)

In accordance with Example 12, except that 1,3-diethoxy-5-ethynylbenzene was used in place of l-ethynyl-3,5-dimethoxybenzene, the title compound was obtained as a colorless, amorphous substance. Table 7 shows the physical properties thereof.

Example 26

Synthesis of 1-(3-((4-amino-3-((3,5-dimethoxyphenyl)ethynyl)-1H-pyrazolo[3,4-d]pyrimidin-1-yl) methyl)pyrrolidin-1-yl)prop-2-en-1-one (compound of Example 26)

(Step 1) Synthesis of tert-butyl 3-((4-amino-3-((3,5-dimethoxyphenyl)ethynyl)-1H-pyrazolo[3,4-d]pyrimidin-1-yl)methyl)pyrrolidine-1-carboxylate DIAD (197 µl) was added to a suspension of 3-((3,5-dimethoxyphenyl)ethynyl)-1H-pyrazolo[3,4-d]pyrimidin-4-amine (148 mg) obtained in Example 1 (Step 1), N-Boc-3-hydroxymethylpyrrolidine (154 mg), polymer supported triphenylphosphine (up to 3.0 mmol/g, 334 mg) in THF (5.0 ml), followed by stirring at room temperature for 3 hours. The insoluble matter was filtered out, and the solvent was distilled off under reduced pressure. The resulting residue was purified by basic silica gel column chromatography (developing solvent: hexane/ethyl acetate) to obtain the title compound as a colorless, amorphous substance (94.5 mg). Physical properties: m/z[M+H]) 479.1.

(Step 2) Synthesis of Compound of Example 26

In accordance with Example 1 (Step 4), except that tert-butyl 3-((4-amino-3-((3,5-dimethoxyphenyl)ethynyl)-1H-pyrazolo[3,4-d]pyrimidin-1-yl)methyl)pyrrolidine-1-carboxylate obtained in Step 1 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 7 shows the physical properties thereof.

Example 27

Synthesis of (S)-1-(3-(4-amino-3-((3,5-dimethoxyphenyl)ethynyl)-1H-pyrazolo[3,4-d]pyrimidin-1-yl) piperidin-1-yl)prop-2-en-1-one (compound of Example 27)

In accordance with Example 26, except that (R)-1-Boc-3-hydroxypiperidine was used in place of N-Boc-3-hydroxymethylpyrrolidine, the title compound was obtained as a white solid. Table 7 shows the physical properties thereof.

Example 28

Synthesis of 1-((2S,4S)-4-(4-amino-3-((3,5-dimethoxyphenyl)ethynyl)-1H-pyrazolo[3,4-d]pyrimidin-1-yl)-2-(hydroxymethyl)pyrrolidin-1-yl)prop-2-en-1-one (compound of Example 28)

(Step 1) Synthesis of (2S,4R)-tert-butyl 2-((tert-butyldiphenylsilyloxy)methyl)-4-hydroxypyrrolidine-1-carboxylate 1-N-Boc-(2S,4R)-4-hydroxy-2-(hydroxymethyl)-pyrrolidine (500 mg) was dissolved in DMF (4.0 ml), and imidazole (164 mg) was added to the dissolution. After cooling to 0° C., tert-butylchlorodiphenylsilane (616 µl) was added to the mixture, and stirred for 1 hour. Ethyl acetate and a saturated aqueous sodium bicarbonate solution were added to the reaction mixture to separate the organic layer. After being washed with a saturated sodium chloride solution, the organic layer was dried over anhydrous sodium sulfate, and the solvent was distilled off under reduced pressure. The resulting residue was purified by silica gel column chromatography (developing solvent: hexane/ethyl acetate) to obtain the title compound as a colorless, oily substance (655 mg). Physical properties: m/z[M+H]$^+$ 456.2.

(Step 2) Synthesis of (2S,4S)-tert-butyl 2-((tert-butyldiphenylsilyloxy)methyl)-4-(methylsulfonyloxy)pyrrolidine-1-carboxylate (2S,4R)-tert-Butyl 2-((tert-butyldiphenylsilyloxy) methyl)-4-hydroxypyrrolidine-1-carboxylate (300 mg) obtained in Step 1 above was dissolved in chloroform (3.0 ml). Triethylamine (137 µl) and methanesulfonyl chloride (56 µl) were added to the solution at 0° C. After stirring at room temperature for 2.0 hours, chloroform and water were added thereto to separate the organic layer. The organic layer was dried over anhydrous magnesium sulfate, and the solvent was distilled off under reduced pressure to obtain the title compound as a colorless, oily compound (389 mg). Physical properties: m/z[M+H]$^+$ 534.1.

(Step 3) Synthesis of (2S,4S)-tert-butyl 4-(4-amino-3-iodo-1H-pyrazolo[3,4-d]pyrimidin-1-yl)-2-((tert-butyldiphenylsilyloxy)methyl)pyrrolidine-1-carboxylate (2S,4S)-tert-butyl 2-((tert-butyldiphenylsilyloxy)methyl)-4-(methylsulfonyloxy)pyrrolidine-1-carboxylate (389 mg) obtained in Step 2 above, 3-iodo-1H-pyrazolo[3,4-d]pyrimidin-4-amine (188 mg), and potassium carbonate (363 mg) were suspended in DMF (4.0 ml), followed by stirring overnight at 80° C. Ethyl acetate and water were added thereto to separate the organic layer. The organic layer was dried over anhydrous magnesium sulfate, and the solvent was distilled off under reduced pressure. The resulting residue was purified by basic silica gel column chromatography (developing solvent: hexane/ethyl acetate) to obtain the title compound as a colorless, oily substance (191 mg). Physical properties: m/z[M+H]$^+$ 699.1.

(Step 4) Synthesis of (2S,4S)-tert-butyl 4-(4-amino-3-((3,5-dimethoxyphenyl)ethynyl)-1H-pyrazolo[3,4-d]pyrimidin-1-yl)-2-((tert-butyldiphenylsilyloxy) methyl)pyrrolidine-1-carboxylate PdCl$_2$ (dppf) CH$_2$Cl$_2$ (13 mg) was added to a mixture of (2S,4S)-tert-butyl 4-(4-amino-3-iodo-1H-pyrazolo[3,4-d]

pyrimidin-1-yl)-2-((tert-butyldiphenylsilyloxy)methyl)pyrrolidine-1-carboxylate (113 mg) obtained in Step 3 above, 1-ethynyl-3,5-dimethoxybenzene (52 mg), copper (I) iodide (6 mg), and triethylamine (0.4 ml) in THF (4 ml). After nitrogen purging, the mixture was stirred at 85° C. for 3 hours. Ethyl acetate and water were added to the reaction mixture to separate the organic layer. After washing with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (100 mg). Physical properties: m/z[M+H]$^+$ 733.3.

(Step 5) Synthesis of (2S,4S)-tert-butyl 4-(4-amino-3-((3,5-dimethoxyphenyl)ethynyl)-1H-pyrazolo[3,4-d]pyrimidin-1-yl)-2-(hydroxymethyl)pyrrolidine-1-carboxylate (2S,4S)-tert-butyl 4-(4-amino-3-((3,5-dimethoxyphenyl)ethynyl)-1H-pyrazolo[3,4-d]pyrimidin-1-yl)-2-((tert-butyldiphenylsilyloxy)methyl)pyrrolidine-1-carboxylate (25 mg) obtained in Step 4 above was dissolved in THF (1.0 ml). Silica gel-supported tetrabutylammonium fluoride (up to 1.5 mmol/g, 34 mg) was added thereto, followed by stirring overnight. Silica gel-supported tetrabutylammonium fluolide (up to 1.5 mmol/g, 30 mg) was further added thereto, and the mixture was further stirred for 2 days. After filtering the reagent off, the solvent was distilled off under reduced pressure. The resulting residue was purified by basic silica gel column chromatography (developing solvent: hexane/ethyl acetate) to obtain the title compound as a colorless, amorphous substance (62 mg). Physical properties: m/z[M+H]$^+$ 495.1.

(Step 6) Synthesis of Compound of Example 28

In accordance with Example 1 (Step 4), except that 4-(4-amino-3-((3,5-dimethoxyphenyl)ethynyl)-1H-pyrazolo[3,4-d]pyrimidin-1-yl)-2-(hydroxymethyl)pyrrolidine-1-carboxylate obtained in Step 5 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 8 shows the physical properties thereof.

Example 29

Synthesis of 1-(3-((4-amino-3-((3,5-dimethoxyphenyl)ethynyl)-1H-pyrazolo[3,4-d]pyrimidin-1-yl)methyl)azetidin-1-yl)prop-2-en-1-one (compound of Example 29)

In accordance with Example 26, except that 1-Boc-3-hydroxymethylazetidine was used in place of N-Boc-3-hydroxymethylpyrrolidine, the title compound was obtained as a light-yellow, amorphous substance. Table 8 shows the physical properties thereof.

Example 30

Synthesis of N-(3-(4-amino-3-((3,5-dimethoxyphenyl)ethynyl)-1H-pyrazolo[3,4-d]pyrimidin-1-yl)cyclobutyl)acrylamide (compound of Example 30)

In accordance with Example 1, except that tert-butyl 3-hydroxycyclobutylcarbamate was used in place of N-Boc-3-hydroxypyrrolidine, the title compound was obtained as a light-yellow, amorphous substance. Table 8 shows the physical properties thereof.

Example 31

Synthesis of 1-(4-(4-amino-3-((3,5-dimethoxyphenyl)ethynyl)-1H-pyrazolo[3,4-d]pyrimidin-1-yl)piperidin-1-yl)prop-2-en-1-one (compound of Example 31)

In accordance with Example 1, except that tert-butyl 4-bromopiperidin-1-carboxylate was used in place of tert-butyl 3-(methylsulfonyloxy)pyrrolidine-1-carboxylate, the title compound was obtained as a white solid. Table 8 shows the physical properties thereof.

Example 32

Synthesis of 1-((2S,4S)-4-(4-amino-3-((3,5-dimethoxyphenyl)ethynyl)-1H-pyrazolo[3,4-d]pyrimidin-1-yl)-2-ethynylpyrrolidin-1-yl)prop-2-en-1-one (compound of Example 32)

(Step 1) Synthesis of (2S,4S)-tert-butyl 4-(4-amino-3-((3,5-dimethoxyphenyl)ethynyl)-1H-pyrazolo[3,4-d]pyrimidin-1-yl)-2-ethynylpyrrolidine-1-carboxylate 3-((3,5-Dimethoxyphenyl)ethynyl)-1H-pyrazolo[3,4-d]pyrimidin-4-amine (14 mg) obtained in Example 1 (Step 1), (2S,4R)-tert-butyl 2-ethynyl-4-hydroxypyrrolidine-1-carboxylate (15 mg) synthesized by the method disclosed in WO2005/007083, and triphenylphosphine (23 mg) were suspended in THF (1.0 ml). DIAD (18 µl) was added to the suspension, and the mixture was stirred at room temperature for 1 hour. The reaction mixture was concentrated and dissolved in a solution of DMSO. The resulting solution was purified by preparative reversed-phase HPLC purification (water/acetonitrile (0.1% formic acid)) to obtain the title compound as a colorless, amorphous substance (5.0 mg). Physical properties: m/z [M+H]$^+$ 489.2.

(Step 2) Synthesis of Compound of Example 32

In accordance with Example 1 (Step 4), except that (2S,4S)-tert-butyl 4-(4-amino-3-((3,5-dimethoxyphenyl)ethynyl)-1H-pyrazolo[3,4-d]pyrimidin-1-yl)-2-ethynylpyrrolidine-1-carboxylate obtained in Step 1 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 9 shows the physical properties thereof.

Example 33

Synthesis of 1-(4-((4-amino-3-((3,5-dimethoxyphenyl)ethynyl)-1H-pyrazolo[3,4-d]pyrimidin-1-yl)methyl)piperidin-1-yl)prop-2-en-1-one (compound of Example 33)

In accordance with Example 26, except that 1-Boc-4-hydroxymethylpiperidine was used in place of N-Boc-3-hydroxymethylpyrrolidine, the title compound was obtained as a light-yellow, amorphous substance. Table 9 shows the physical properties thereof.

Example 34

Synthesis of N-(3-((4-amino-3-((3,5-dimethoxyphenyl)ethynyl)-1H-pyrazolo[3,4-d]pyrimidin-1-yl)methyl)phenyl)acrylamide (compound of Example 34)

In accordance with Example 26, except that (3-aminophenyl)methanol was used in place of N-Boc-3-hydroxymethylpyrrolidine, the title compound was obtained as a colorless, amorphous substance. Table 9 shows the physical properties thereof.

Example 35

Synthesis of 1-(3-((4-amino-3-((3,5-dimethoxyphenyl)ethynyl)-1H-pyrazolo[3,4-d]pyrimidin-1-yl)methyl)azetidin-1-yl)-4-(dimethylamino)but-2-en-1-one (compound of Example 35)

In accordance with Example 4, except that 1-(azetidin-3-ylmethyl)-3-((3,5-dimethoxyphenyl)ethynyl)-1H-pyrazolo[3,4-d]pyrimidin-4-amine (i.e., the intermediate obtained in Example 29) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 9 shows the physical properties thereof.

Example 36

Synthesis of 1-(4-(4-amino-3-((3,5-dimethoxyphenyl)ethynyl)-1H-pyrazolo[3,4-d]pyrimidin-1-yl)piperidin-1-yl)-4-(dimethylamino)but-2-en-1-one (compound of Example 36)

In accordance with Example 4, except that 3-((3,5-dimethoxyphenyl)ethynyl)-1-(piperidin-4-yl)-1H-pyrazolo[3,4-d]pyrimidin-4-amine (i.e., the intermediate obtained in Example 31) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 9 shows the physical properties thereof.

Example 37

Synthesis of 1-(4-((4-amino-3-((3,5-dimethoxyphenyl)ethynyl)-1H-pyrazolo[3,4-d]pyrimidin-1-yl)methyl)piperidin-1-yl)-4-(dimethylamino)but-2-en-1-one (compound of Example 37)

In accordance with Example 4, except that 3-((3,5-dimethoxyphenyl)ethynyl)-1-(piperidin-4-ylmethyl)-1H-pyrazolo[3,4-d]pyrimidin-4-amine (i.e., the intermediate obtained in Example 33) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 10 shows the physical properties thereof.

Example 38

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(dimethylamino)but-2-en-1-one (compound of Example 38)

(Step 1) Synthesis of (S)-tert-butyl 3-(4-chloro-5-iodo-7H-pyrrolo[2,3-d]pyrimidin-7-yl)pyrrolidine-1-carboxylate DIAD (1.41 ml) was added to a solution of 4-chloro-5-iodo-7H-pyrrolo[2,3-d]pyrimidine (1.00 g), (R)—N-Boc-3-pyrrolidinol (1.01 g), and triphenylphosphine (1.88 g) in tetrahydrofuran (40 ml), and the reaction mixture was stirred for 1 hour. The reaction mixture was concentrated and washed with ethyl acetate to obtain the title compound as a white solid (1.04 g). Physical properties: m/z[M+H]$^+$ 448.9.

(Step 2) Synthesis of (S)-tert-butyl 3-(4-amino-5-iodo-7H-pyrrolo[2,3-d]pyrimidin-7-yl)pyrrolidine-1-carboxylate Tetrahydrofuran (2.5 ml) and 28% aqueous ammonia (2.5 ml) were added to (S)-tert-butyl 3-(4-chloro-5-iodo-7H-pyrrolo[2,3-d]pyrimidin-7-yl)pyrrolidine-1-carboxylate (400 mg) obtained in Step 1 above. The reaction mixture was stirred at 100° C. for 1.5 hours using a microwave reactor. Chloroform and water were added thereto to separate the organic layer. The organic layer was dried over anhydrous sodium sulfate, and the solvent was distilled off under reduced pressure to obtain the title compound as a white, solid compound (382 mg). Physical properties: m/z[M+H]$^+$ 430.3.

(Step 3) Synthesis of (S)-tert-butyl 3-(4-amino-5-((3,5-dimethoxyphenyl)ethynyl)-7H-pyrrolo[2,3-d]pyrimidin-7-yl)pyrrolidine-1-carboxylate PdCl$_2$(dppf)$_2$CH$_2$Cl$_2$ (122 mg) was added to a mixture of (S)-tert-butyl 3-(4-amino-5-iodo-7H-pyrrolo[2,3-d]pyrimidin-7-yl)pyrrolidine-1-carboxylate (660 mg) obtained in Step 2 above, 1-ethynyl-3,5-dimethoxybenzene (374 mg), copper (I) iodide (44 mg), and triethylamine (2.0 ml) in THF (15 ml). After nitrogen purging, the resulting mixture was stirred at 80° C. for 3.5 hours. Ethyl acetate and water were added to the reaction mixture to separate the organic layer. After washing with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (714 mg). Physical properties: m/z[M+H]$^+$ 464.1.

(Step 4) Synthesis of Compound of Example 38

4N-Hydrochloric acid/1,4-dioxane (2 ml) was added to the (S)-tert-butyl 3-(4-amino-5-((3,5-dimethoxyphenyl)ethynyl)-7H-pyrrolo[2,3-d]pyrimidin-7-yl)pyrrolidine-1-carboxylate (30 mg) obtained in Step 3 above, and the mixture was stirred at room temperature for 1.5 hours. After distilling the solvent of the resulting reaction mixture off under reduced pressure, toluene azeotropic distillation was subsequently performed to obtain a crude product of (S)-5-((3,5-dimethoxyphenyl)ethynyl)-7-(pyrrolidin-3-yl)-7H-pyrrolo[2,3-d]pyrimidin-4-amine (30 mg). A portion of the resulting crude product (10 mg), 4-(dimethylamino)but-2-enoic acid hydrochloride (5.9 mg), and HATU (14 mg) were dissolved in DMF (1.0 ml). DIPEA (50 µl) was added thereto and stirred at room temperature for 5 minutes. Chloroform and water were added to the reaction mixture to separate the organic layer. After being washed with a saturated sodium chloride solution, the organic layer was dried over anhydrous sodium sulfate, and the solvent was distilled off under reduced pressure. The resulting residue was purified by preparative reversed-phase HPLC purification (water/acetonitrile (0.1% formic acid)) to obtain the title compound as a colorless, amorphous substance (3.9 mg). Table 10 shows the physical properties thereof.

Example 39

Synthesis of (S)-1-(3-(4-amino-5-((3,5-dimethoxyphenyl)ethynyl)-7H-pyrrolo[2,3-d]pyrimidin-7-yl)pyrrolidin-1-yl)prop-2-en-1-one (compound of Example 39)

In accordance with Example 1 (Step 4), except that (S)-tert-butyl 3-(4-amino-5-((3,5-dimethoxyphenyl)ethynyl)-7H-pyrrolo[2,3-d]pyrimidin-7-yl)pyrrolidine-1-carboxylate obtained in Example 38 (Step 3) was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of (S)-5-((3,5-dimethoxyphenyl)ethynyl)-7-(pyrrolidin-3-yl)-7H-pyrrolo[2,3-d]pyrimidin-4-amine was obtained by removing a Boc group under acidic conditions. Thereafter, amidation was conducted to obtain the title compound as a white solid. Table 10 shows the physical properties thereof.

Example 40

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(pyrrolidin-1-yl)but-2-en-1-one (compound of Example 40)

(Step 1) Synthesis of 4-(pyrrolidin-1-yl)but-2-enoic acid hydrochloride

Methyl 4-bromocrotonate (1.79 g) was dissolved in tetrahydrofuran (40 ml), pyrrolidine (1.67 ml) was added thereto at 0° C., and the mixture was stirred at room temperature for 1 hour. Diethyl ether and water were added to the reaction mixture to separate the organic layer. After being washed with a saturated sodium chloride solution, the organic layer was dried over anhydrous sodium sulfate, and the solvent was distilled off under reduced pressure. 3N Hydrochloric acid (40 ml) was added to the resulting product, and the mixture was heated under reflux at 100° C. for 1 hour. The reaction mixture was concentrated under reduced pressure, and then the resulting residue was washed with a mixed solvent of isopropanol and ethyl acetate to obtain the title compound as a white solid (939 mg). Physical properties: m/z[M+H]$^+$ 156.0.

(Step 2) Synthesis of Compound of Example 40

In accordance with Example 4 (Step 1), except that (S)-5-((3,5-dimethoxyphenyl)ethynyl)-7-(pyrrolidin-3-yl)-7H-pyrrolo[2,3-d]pyrimidin-4-amine (the intermediate obtained in Example 38 (Step 4)) and 4-(pyrrolidin-1-yl)but-2-enoic acid hydrochloride obtained in Step 1 above were used, the title compound was obtained as a colorless, amorphous substance. Table 10 shows the physical properties thereof.

Example 41

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(4-methylpiperazin-1-yl)but-2-en-1-one (compound of Example 41)

(Step 1) Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-bromobut-2-en-1-one The crude product (100 mg) of (S)-5-((3,5-dimethoxyphenyl)ethynyl)-7-(pyrrolidin-3-yl)-7H-pyrrolo[2,3-d]pyrimidin-4-amine (i.e., the intermediate obtained in Example 38 (Step 4)) was suspended in chloroform (3.0 ml). DIPEA (117 µl) was added to the suspension, and the mixture was cooled to 0° C. A solution of 4-bromobut-2-enoyl chloride (46 mg) obtained in Example 16 (Step 1) in chloroform (0.3 ml) was added thereto dropwise, and the resulting mixture was stirred at room temperature for 15 minutes. After halting the reaction using a saturated aqueous sodium bicarbonate solution, the resulting product was extracted with ethyl acetate. The organic layer was dried over anhydrous sodium sulfate, and the solvent was distilled off under reduced pressure to obtain the title compound as a crude product (140 mg). Physical properties: m/z[M+H]$^+$ 509.9, 511.9.

(Step 2) Synthesis of Compound of Example 41

The crude product (12 mg) of (S)-1-(3-(4-amino-5-((3,5-dimethoxyphenyl)ethynyl)-7H-pyrrolo[2,3-d]pyrimidin-7-yl)pyrrolidin-1-yl)-4-bromobut-2-en-1-one obtained in Step 1 above was dissolved in DMF (0.5 ml). N-methylpiperazine (4 mg) and DIPEA (10 µl) were added thereto, followed by stirring at room temperature overnight. After concentrating under reduced pressure, the resulting residue was purified by preparative reversed-phase HPLC purification (water/acetonitrile (0.1% formic acid)) to obtain the title compound as a colorless, amorphous substance (3.0 mg). Table 11 shows the physical properties thereof.

Example 42

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(4-hydroxypiperidin-1-yl)but-2-en-1-one (compound of Example 42)

In accordance with Example 41 (Step 2), except that 4-hydroxypiperidine was used in place of N-methylpiperazine, the title compound was obtained as a colorless, amorphous substance. Table 11 shows the physical properties thereof.

Example 43

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(4-fluoropiperidin-1-yl)but-2-en-1-one (compound of Example 43)

In accordance with Example 41 (Step 2), except that 4-fluoropiperidine was used in place of N-methylpiperazine, the title compound was obtained as a colorless, amorphous substance. Table 11 shows the physical properties thereof.

Example 44

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(3,3-difluoropyrrolidin-1-yl)but-2-en-1-one (compound of Example 44)

In accordance with Example 41 (Step 2), except that 3,3-difluoropyrrolidine was used in place of N-methylpiperazine, the title compound was obtained as a colorless, amorphous substance. Table 12 shows the physical properties thereof.

Example 45

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(4,4-difluoropiperidin-1-yl)but-2-en-1-one (compound of Example 45)

In accordance with Example 41 (Step 2), except that 4,4-difluoropiperidine was used in place of N-methylpiperazine, the title compound was obtained as a colorless, amorphous substance. Table 12 shows the physical properties thereof.

Example 46

Synthesis of (S)-1-(3-(4-amino-5-((3,5-dimethoxyphenyl)ethynyl)-7H-pyrrolo[2,3-d]pyrimidin-7-yl)pyrrolidin-1-yl)but-2-yn-1-one (compound of Example 46)

In accordance with Example 4 (Step 1), except that (S)-5-((3,5-dimethoxyphenyl)ethynyl)-7-(pyrrolidin-3-yl)-7H-pyrrolo[2,3-d]pyrimidin-4-amine (i.e., the intermediate obtained in Example 38 (Step 4)) and 2-butynoic acid were used, the title compound was obtained as a colorless, amorphous substance. Table 12 shows the physical properties thereof.

Example 47

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-hydroxy-4-methylpent-2-yn-1-one (compound of Example 47)

In accordance with Example 4 (Step 1), except that (S)-5-((3,5-dimethoxyphenyl)ethynyl)-7-(pyrrolidin-3-yl)-7H-pyrrolo[2,3-d]pyrimidin-4-amine (i.e., the intermediate obtained in Example 38 (Step 4)) and 4-hydroxy-4-methylpent-2-ynoic acid were used, the title compound was obtained as a colorless, amorphous substance. Table 12 shows the physical properties thereof.

Example 48

Synthesis of 1-((S)-3-(4-amino-5-((3,5-dimethoxyphenyl)ethynyl)-7H-pyrrolo[2,3-d]pyrimidin-7-yl)pyrrolidin-1-yl)-4-((R)-3-fluoropyrrolidin-1-yl)but-2-en-1-one (compound of Example 48)

In accordance with Example 41 (Step 2), except that (R)-3-fluoropyrrolidine was used in place of N-methylpiperazine, the title compound was obtained as a colorless, amorphous substance. Table 13 shows the physical properties thereof.

Example 49

Synthesis of 1-((S)-3-(4-amino-5-((3,5-dimethoxyphenyl)ethynyl)-7H-pyrrolo[2,3-d]pyrimidin-7-yl)pyrrolidin-1-yl)-4-((S)-3-fluoropyrrolidin-1-yl)but-2-en-1-one (compound of Example 49)

In accordance with Example 41 (Step 2), except that (S)-3-fluoropyrrolidine was used in place of N-methylpiperazine, the title compound was obtained as a colorless, amorphous substance. Table 13 shows the physical properties thereof.

Example 50

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(piperidin-1-yl)but-2-en-1-one (compound of Example 50)

In accordance with Example 41 (Step 2), except that piperidine was used in place of N-methylpiperazine, the title compound was obtained as a colorless, amorphous substance. Table 13 shows the physical properties thereof.

Example 51

Synthesis of 1-(3-(4-amino-5-((3,5-dimethoxyphenyl)ethynyl)-7H-pyrrolo[2,3-d]pyrimidin-7-yl)azetidin-1-yl)prop-2-en-1-one (compound of Example 51)

(Step 1) Synthesis of tert-butyl 3-(4-chloro-5-iodo-7H-pyrrolo[2,3-d]pyrimidin-7-yl)azetidine-1-carboxylate DIAD (1.41 ml) was added to a solution of 4-chloro-5-iodo-7H-pyrrolo[2,3-d]pyrimidine (1.00 g), N-Boc-3-hydroxyazetidine (930 mg), and triphenylphosphine (1.85 g) in tetrahydrofuran (40 ml), and the reaction mixture was stirred for 1 hour. After concentrating, the reaction mixture was washed with ethyl acetate to obtain the title compound as a white solid (1.07 g). Physical properties: m/z[M+H]$^+$ 435.0.

(Step 2) Synthesis of tert-butyl 3-(4-amino-5-iodo-7H-pyrrolo[2,3-d]pyrimidin-7-yl)azetidine-1-carboxylate Tetrahydrofuran (2.5 ml) and 28% aqueous ammonia (2.5 ml) were added to the tert-butyl 3-(4-chloro-5-iodo-7H-pyrrolo[2,3-d]pyrimidin-7-yl)azetidine-1-carboxylate (350 mg) obtained in Step 1 above. The reaction mixture was stirred at 100° C. for 1.5 hours using a microwave reactor. Chloroform and water were added thereto to separate the organic layer. The organic layer was dried over anhydrous sodium sulfate, and the solvent was distilled off under reduced pressure to obtain the title compound as a white solid (340 mg). Physical properties: m/z[M+H]$^+$ 416.0.

(Step 3) Synthesis of tert-butyl 3-(4-amino-5-((3,5-dimethoxyphenyl)ethynyl)-7H-pyrrolo[2,3-d]pyrimidin-7-yl)azetidine-1-carboxylate PdCl$_2$(dppf)CH$_2$Cl$_2$ (122 mg) was added to a mixture of tert-butyl 3-(4-amino-5-iodo-7H-pyrrolo[2,3-d]pyrimidin- 7-yl)azetidine-1-carboxylate (639 mg) obtained in Step 2 above, 1-ethynyl-3,5-dimethoxybenzene (374 mg), copper (I) iodide (44 mg), and triethylamine (2.0 ml) in THF (15 ml). After nitrogen purging, the resulting mixture was stirred at 80° C. for 3.5 hours. Ethyl acetate and water were added to the reaction mixture to separate the organic layer. After being washed with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (704 mg). Physical properties: m/z[M+H]$^+$ 450.1.

(Step 4) Synthesis of Compound of Example 51

In accordance with Example 1 (Step 4), except that tert-butyl 3-(4-amino-5-((3,5-dimethoxyphenyl)ethynyl)-7H-pyrrolo[2,3-d]pyrimidin-7-yl)azetidine-1-carboxylate obtained in Step 3 was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of 7-(azetidin-3-y)-5-((3,5-)dimethoxyphenyl)ethynyl)-7H-pyrrolo[2,3-d]pyrimidin-4-amine was obtained by removing a Boc group under acidic conditions. Thereafter, amidation was conducted to obtain the title compound as a white solid. Table 13 shows the physical properties thereof.

Example 52

Synthesis of 1-(3-(4-amino-5-((3,5-dimethoxyphenyl)ethynyl)-7H-pyrrolo[2,3-d]pyrimidin-7-yl)azetidin-1-yl)-4-(dimethylamino)but-2-en-1-one (Example Compound 52)

In accordance with Example 4 (Step 1), except that the tert-butyl 3-(4-amino-5-((3,5-dimethoxyphenyl)ethynyl)-7H-pyrrolo[2,3-d]pyrimidin-7-yl)azetidine-1-carboxylate obtained in Example 51 (Step 3) was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a colorless, amorphous substance. Table 14 shows the physical properties thereof.

Example 53

Synthesis of 1-(3-(4-amino-5-((3,5-dimethoxyphenyl)ethynyl)-7H-pyrrolo[2,3-d]pyrimidin-7-yl)azetidin-1-yl)-4-(pyrrolidin-1-yl)but-2-en-1-one (Example Compound 53)

In accordance with Example 4 (Step 1), the 7-(azetidin-3-yl)-5-((3,5-)dimethoxyphenyl)ethynyl)-7H-pyrrolo[2,3-d]pyrimidin-4-amine obtained in Example 51 (Step 4) as an intermediate, and the 4-(pyrrolidin-1-yl)but-2-enoic acid hydrochloride obtained in Example 40 (Step 1) were used to obtain the title compound as a colorless, amorphous substance. Table 14 shows the physical properties thereof.

Example 54

Synthesis of 1-(3-(4-amino-5-((3,5-dimethoxyphenyl)ethynyl)-7H-pyrrolo[2,3-d]pyrimidin-7-yl)azetidin-1-yl)but-2-yn-1-one (Example Compound 54)

In accordance with Example 4 (Step 1), the 7-(azetidin-3-yl)-5-((3,5-)dimethoxyphenyl)ethynyl)-7H-pyrrolo[2,3-d]pyrimidin-4-amine obtained as an intermediate in Example 51 (Step 4) and 2-butynoic acid were used to obtain the title compound as a colorless, amorphous substance. Table 14 shows the physical properties thereof.

Example 55

Synthesis of 1-(3-(4-amino-5-((3,5-dimethoxyphenyl)ethynyl)-7H-pyrrolo[2,3-d]pyrimidin-7-yl)azetidin-1-yl)-4-(azetidin-1-yl)but-2-en-1-one (Example Compound 55)

(Step 1) Synthesis of 1-(3-(4-amino-5-((3,5-dimethoxyphenyl)ethynyl)-7H-pyrrolo[2,3-d]pyrimidin-7-yl)azetidin-1-yl)-4-bromobut-2-en-1-one A crude product of 7-(azetidin-3-yl)-5-((3,5-dimethoxyphenyl)ethynyl)-7H-pyrrolo[2,3-d]pyrimidin-4-amine (160 mg) obtained in Example 52 (Step 4) as an intermediate was suspended in THF (3.0 ml). DIPEA (202 μl) was added thereto, and the mixture was cooled to 0° C. A solution of 4-bromobut-2-enoyl chloride (75 mg) obtained in Example 16 (Step 1) in THF (0.5 ml) was added to the mixture dropwise, and stirred at room temperature for 15 minutes. After halting the reaction using a saturated sodium bicarbonate solution, the resulting product was extracted with ethyl acetate. After drying the result over anhydrous sodium sulfate, the solvent was distilled off under reduced pressure to obtain the title compound as a crude product (204 mg). Physical properties: m/z[M+H]$^+$ 496.0, 498.0.

(Step 2) Synthesis of Example Compound 55

The crude product of 1-(3-(4-amino-5-((3,5-dimethoxyphenyl)ethynyl)-7H-pyrrolo[2,3-d]pyrimidin-7-yl)azetidin-1-yl)-4-bromobut-2-en-1-one (10 mg) obtained in Step 1 above was suspended in THF (0.5 ml). Azetidine (7 μl) was added thereto, and the resulting mixture was stirred for 1 hour at room temperature. After concentrating under reduced pressure, the resulting residue was purified by reversed-phase HPLC purification (water/acetonitrile (0.1% formic acid)) to obtain the title compound as a colorless, amorphous substance (1.6 mg). Table 14 shows the physical properties thereof.

Example 56

Synthesis of 1-(3-(4-amino-5-((3,5-dimethoxyphenyl)ethynyl)-7H-pyrrolo[2,3-d]pyrimidin-7-yl)azetidin-1-yl)-4-(ethyl(methyl)amino)but-2-en-1-one (Example Compound 56)

In accordance with Example 55 (Step 2), except that ethylmethylamine was used in place of azetidine, the title compound was obtained as a colorless, amorphous substance. Table 15 shows the physical properties thereof.

Example 57

Synthesis of 1-(3-(4-amino-5-((3,5-dimethoxyphenyl)ethynyl)-7H-pyrrolo[2,3-d]pyrimidin-7-yl)azetidin-1-yl)-4-(isopropylamino)but-2-en-1-one (Example Compound 57)

In accordance with Example 55 (Step 2), except that isopropylamine was used in place of azetidine, the title compound was obtained as a colorless, amorphous substance. Table 15 shows the physical properties thereof.

Example 58

Synthesis of 1-(3-(4-amino-5-((3,5-dimethoxyphenyl)ethynyl)-7H-pyrrolo[2,3-d]pyrimidin-7-yl)azetidin-1-yl)-4-(isopropyl(methyl)amino)but-2-en-1-one (Example Compound 58)

In accordance with Example 55 (Step 2), except that isopropylmethylamine was used in place of azetidine, the title compound was obtained as a colorless, amorphous substance. Table 15 shows the physical properties thereof.

Example 59

Synthesis of 1-(3-(4-amino-5-((3,5-dimethoxyphenyl)ethynyl)-7H-pyrrolo[2,3-d]pyrimidin-7-yl)azetidin-1-yl)-4-(diethylamino)but-2-en-1-one (Example Compound 59)

In accordance with Example 55 (Step 2), except that diethylamine was used in place of azetidine, the title compound was obtained as a colorless, amorphous substance. Table 16 shows the physical properties thereof.

Example 60

Synthesis of 1-(3-(4-amino-5-((3,5-dimethoxyphenyl)ethynyl)-7H-pyrrolo[2,3-d]pyrimidin-7-yl)azetidin-1-yl)-4-((2-methoxyethyl)(methyl)amino)but-2-en-1-one (Example Compound 60)

In accordance with Example 55 (Step 2), except that 2-methoxy-N-methylethanamine was used in place of azetidine, the title compound was obtained as a colorless, amorphous substance. Table 16 shows the physical properties thereof.

Example 61

Synthesis of 1-(3-(4-amino-5-((3,5-dimethoxyphenyl)ethynyl)-7H-pyrrolo[2,3-d]pyrimidin-7-yl)azetidin-1-yl)-4-(4-hydroxypiperidin-1-yl)but-2-en-1-one (Example Compound 61)

In accordance with Example 55 (Step 2), except that 4-hydroxypiperidin was used in place of azetidine, the title compound was obtained as a colorless, amorphous substance. Table 16 shows the physical properties thereof.

Example 62

Synthesis of (S)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Example Compound 62)

In accordance with Example 55 (Step 2), except that (S)-3-hydroxypyrrolidine was used in place of azetidine, the title compound was obtained as a colorless, amorphous substance. Table 17 shows the physical properties thereof.

Example 63

Synthesis of (R)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Example Compound 63)

In accordance with Example 55 (Step 2), except that (R)-3-hydroxypyrrolidine was used in place of azetidine, the title compound was obtained as a colorless, amorphous substance. Table 17 shows the physical properties thereof.

Example 64

Synthesis of 1-(4-(4-amino-5-((3,5-dimethoxyphenyl)ethynyl)-7H-pyrrolo[2,3-d]pyrimidin-7-yl)piperidin-1-yl)prop-2-en-1-one (Example Compound 64)

In accordance with Example 39, except that N-Boc-4-piperidinol was used in place of (R)—N-Boc-3-pyrrolidinol, the title compound was obtained as a light-yellow, amorphous substance. Table 17 shows the physical properties thereof.

Example 65

Synthesis of 1-(4-(4-amino-5-((3,5-dimethoxyphenyl)ethynyl)-7H-pyrrolo[2,3-d]pyrimidin-7-yl)piperidin-1-yl)-4-(dimethylamino)but-2-en-1-one (Example Compound 65)

In accordance with Example 38, except that N-Boc-4-piperidinol was used in place of (R)—N-Boc-3-pyrrolidinol, the title compound was obtained as a light-yellow, amorphous substance. Table 17 shows the physical properties thereof.

Example 66

Synthesis of (2S,4S)-methyl 1-acryloyl-4-(4-amino-5-((3,5-dimethoxyphenyl)ethynyl)-7H-pyrrolo[2,3-d]pyrimidin-7-yl)pyrrolidine-2-carboxylate (Example Compound 66)

(Step 1) Synthesis of 4-chloro-5-iodo-7-((2-(trimethylsilyl)ethoxy)methyl)-7H-pyrrolo[2,3-d]pyrimidine 4-Chloro-5-iodo-7H-pyrrolo[2,3-d]pyrimidine (7.01 g) synthesized by the method disclosed in WO2005/042556 was dissolved in anhydrous THF (125 ml). After cooling to 0° C., 60% sodium hydride (4.02 g) was added to the result, and the resulting mixture was stirred for 20 minutes. Subsequently, SEMCl (13.3 ml) was added thereto, and the mixture was stirred at room temperature overnight. After cooling to 0° C. again, water was added to the mixture, and the reaction was halted. The resulting product was extracted with ethyl acetate, and the organic layer was washed with a saturated sodium chloride solution. After drying the result over anhydrous sodium sulfate, the solvent was distilled off under reduced pressure. The resulting residue was purified by silica gel column chromatography (developing solvent:

hexane/ethyl acetate) to obtain the title compound as a white solid (7.28 g). Physical properties: m/z[M+H]$^+$ 410.0.

(Step 2) Synthesis of 5-iodo-7-((2-(trimethylsilyl) ethoxy)methyl)-7H-pyrrolo[2,3-d]pyrimidin-4-amine The 4-chloro-5-iodo-7-((2-(trimethylsilyl)ethoxy) methyl)-7H-pyrrolo[2,3-d]pyrimidine (200 mg) obtained in Step 1 above was dissolved in THF (2.0 ml). 28% Aqueous ammonia (2 ml) was added thereto, and the reaction mixture was then stirred at 105° C. for 1.5 hours using a microwave reactor. The resulting product was extracted with ethyl acetate, and the organic layer was washed with a saturated sodium chloride solution. After drying the result over anhydrous sodium sulfate, the solvent was distilled off under reduced pressure to obtain the title compound as a white solid (192 mg). Physical properties: m/z[M+H]$^+$ 391.0.

(Step 3) Synthesis of 5-((3,5-dimethoxyphenyl) ethynyl)-7-((2-(trimethylsilyl)ethoxy)methyl)-7H-pyrrolo[2,3-d]pyrimidin-4-amine In accordance with Example 1 (Step 1), except that the 5-iodo-7-((2-(trimethylsilyl)ethoxy)methyl)-7H-pyrrolo[2,3-d]pyrimidin-4-amine obtained in Step 2 above was used in place of 3-iodo-1H-pyrazolo[3,4-d]pyrimidin-4-amine, the title compound was obtained as a colorless solid. Physical properties: m/z [M+H]$^+$ 425.4.

(Step 4) Synthesis of 5-((3,5-dimethoxyphenyl) ethynyl)-7H-pyrrolo[2,3-d]pyrimidin-4-amine A solution of 5-((3,5-dimethoxyphenyl)ethynyl)-7-((2-(trimethylsilyl)ethoxy)methyl)-7H-pyrrolo[2,3-d]pyrimidin-4-amine (4.27 g) obtained in Step 3 in methylene chloride (20 ml) was cooled to 0° C., and TFA (10 ml) was added thereto. The reaction mixture was stirred at room temperature for 5 hours, and the solvent was distilled off under reduced pressure. THF (50 ml) was added to the residue, and the mixture was cooled to 0° C. 4N aqueous sodium hydroxide (12.5 ml) was added thereto, and the mixture was stirred at room temperature overnight. The result was extracted with ethyl acetate, and dried over anhydrous magnesium sulfate. Subsequently, the solvent was distilled off under reduced pressure, and chloroform was added to the resulting residue. The mixture was subjected to filtration to obtain the title compound as a white solid (2.60 g). Physical properties: m/z[M+H]$^+$ 295.3.

(Step 5) Synthesis of (2S,4R)-4-(methylsulfonyloxy)-pyrrolidine-1,2-dicarboxylic acid 1-tert-butylester-2-methylester In accordance with Example 1 (Step 2), except that (2S,4R)-4-hydroxy-pyrrolidine-1,2-dicarboxylic acid 1-tert-butylester-2-methylester was used in place of N-Boc-3-pyrrolidinol, the title compound was obtained as a colorless, amorphous substance.

(Step 6) Synthesis of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate In accordance with Example 1 (Step 3), except that the 5-((3,5-dimethoxyphenyl)ethynyl)-7H-pyrrolo[2,3-d]pyrimidin-4-amine obtained in Step 4, the (2S,4R)-4-(methyl-sulfonyloxy)-pyrrolidine-1,2-dicarboxylic acid 1-tert-butylester-2-methylester obtained in Step 5, sodium hydride, and NMP were individually used in place of 3-((3,5-dimethoxyphenyl)ethynyl)-1H-pyrazolo[3,4-d]pyrimidin-4-amine, tert-butyl 3-(methylsulfonyloxy)pyrrolidine-1-carboxylate, potassium carbonate, and DMF, the title compound was obtained as a colorless, amorphous substance. Physical properties: m/z[M+H]$^+$ 522.4.

(Step 7) Synthesis of (2S,4S)-methyl 4-(4-amino-5-((3,5-dimethoxyphenyl)ethynyl)-7H-pyrrolo[2,3-d] pyrimidin-7-yl)pyrrolidine-2-carboxylate A solution of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate (24 mg) obtained in Step 6 above in methylene chloride (2.0 ml) and TFA (2.0 ml) was stirred at room temperature for 30 minutes. The solvent was distilled off under reduced pressure, and the resulting residue was purified by basic silica gel column chromatography (developing solvent: chloroform/methanol). The title compound was thus obtained as a light-yellow, amorphous substance (11.9 mg). Physical properties: m/z[M+H]$^+$ 422.1.

(Step 8) Synthesis of Example Compound 66

Methylene chloride (2.0 ml) and triethylamine (16 μl) were added to the (2S,4S)-methyl 4-(4-amino-5-((3,5-dimethoxyphenyl)ethynyl)-7H-pyrrolo[2,3-d]pyrimidin-7-yl) pyrrolidine-2-carboxylate (12 mg) obtained in Step 7 above. After cooling to 0° C., chloroform (100 μl) in which acryloyl chloride (5 μl) was dissolved was added to the resulting mixture, and stirred at room temperature for 10 minutes. After halting the reaction using a saturated sodium bicarbonate solution, the resulting product was extracted with ethyl acetate. After drying the result over anhydrous sodium sulfate, the solvent was distilled off under reduced pressure. The resulting residue was purified by silica gel column chromatography (developing solvent: ethyl acetate/methanol) to obtain the title compound as a colorless, amorphous substance (4.2 mg). Table 18 shows the physical properties thereof.

Example 67

Synthesis of 1-((2S,4S)-4-(4-amino-5-((3,5-dimethoxyphenyl)ethynyl)-7H-pyrrolo[2,3-d]pyrimidin-7-yl)-2-((dimethylamino)methyl)pyrrolidin-1-yl) prop-2-en-1-one (Example Compound 67)

(Step 1) Synthesis of (2S,4S)-tert-butyl 2-((tert-butyldiphenylsilyloxy)methyl)-4-(4-chloro-5-iodo-7H-pyrrolo[2,3-d]pyrimidin-7-yl)pyrrolidine-1-carboxylate A solution of triphenylphosphine (443 mg) in THF (25 ml) was cooled to 0° C., and DIAD (340 μl) was added thereto dropwise. The reaction mixture was stirred at 0° C. for 1 hour. 4-Chloro-5-iodo-7H-pyrrolo[2,3-d]pyrimidine (363 mg) and the (2S,4R)-tert-butyl 2-((tert-butyldiphenylsilyloxy)methyl)-4-hydroxypyrrolidine-1-carboxylate (651.6 mg) obtained in Example 28 (Step 1) were added thereto, and stirred at room temperature overnight. Ethyl acetate and water were added to separate the organic layer. The organic layer was dried over anhydrous magnesium sulfate, and the solvent was distilled off under reduced pressure. The resulting residue was purified by silica gel column chromatography (developing solvent: hexane/ethyl acetate) to obtain the title compound as a light-yellow, amorphous substance (400 mg). m/z[M+H]$^+$ 718.5.

(Step 2) Synthesis of (2S,4S)-tert-butyl 4-(4-amino-5-iodo-7H-pyrrolo[2,3-d]pyrimidin-7-yl)-2-((tert-butyldiphenylsilyloxy)methyl)pyrrolidine-1-carboxylate THF (10 ml) and an 8N ammonia methanol solution (5 ml) were added to the (2S,4S)-tert-butyl 2-((tert-butyldiphenylsilyloxy)methyl)-4-(4-chloro-5-iodo-7H-pyrrolo[2,3-d]pyrimidin-7-yl)pyrrolidine-1-carboxylate (400 mg) obtained in Step 1. The mixture was stirred at 120° C. for 2 hours under microwave irradiation, and the solvent was distilled off under reduced pressure. The resulting residue was purified by silica gel column chromatography (developing solvent: chloroform/ethanol) to obtain the title compound as a light-yellow solid (293 mg). Physical properties: m/z[M+H]$^+$ 698.5.

(Step 3) Synthesis of (2S,4S)-tert-butyl 4-(4-(bis(tert-butoxycarbonyl)amino)-5-iodo-7H-pyrrolo[2,3-d]pyrimidin-7-yl)-2-((tert-butyldiphenylsilyloxy)methyl)pyrrolidine-1-carboxylate Boc$_2$O (188 mg) and DMAP (7 mg) were added to a solution of (2S,4S)-tert-butyl 4-(4-amino-5-iodo-7H-pyrrolo[2,3-d]pyrimidin-7-yl)-2-((tert-butyldiphenylsilyloxy)methyl)pyrrolidine-1-carboxylate (200 mg) obtained in Step 2 in THF (5 ml), and the resulting mixture was stirred at room temperature overnight. Ethyl acetate and water were added to the reaction mixture to separate the organic layer. The organic layer was dried over anhydrous magnesium sulfate, and the solvent was distilled off under reduced pressure. The resulting residue was purified by silica gel column chromatography (developing solvent: hexane/ethyl acetate) to obtain the title compound as a light-yellow, amorphous substance (238 mg). m/z[M+H]$^+$ 898.5.

(Step 4) Synthesis of (2S,4S)-tert-butyl 4-(4-(bis(tert-butoxycarbonyl)amino)-5-iodo-7H-pyrrolo[2,3-d]pyrimidin-7-yl)-2-(hydroxymethyl)pyrrolidine-1-carboxylate Silica gel-carrying tetrabutyl ammonium fluoride (700 mg) (up to 1.5 mmol/g) was added to a solution of (2S,4S)-tert-butyl 4-(4-(bis(tert-butoxycarbonyl)amino)-5-iodo-7H-pyrrolo[2,3-d]pyrimidin-7-yl)-2-((tert-butyldiphenylsilyloxy)methyl)pyrrolidine-1-carboxylate (237.5 mg) obtained in Step 3 in THF (5 ml), and the resulting mixture was stirred at room temperature overnight. Silica gel was separated by filtration, and the solvent of the filtrate was distilled off under reduced pressure. The resulting residue was purified by silica gel column chromatography (developing solvent: hexane/ethyl acetate) to obtain the title compound as a light-yellow, amorphous substance (185 mg). Physical properties: m/z[M+H]$^+$ 660.2.

(Step 5) Synthesis of (2S,4S)-tert-butyl 4-(4-(bis(tert-butoxycarbonyl)amino)-5-iodo-7H-pyrrolo[2,3-d]pyrimidin-7-yl)-2-formylpyrrolidine-1-carboxylate Dess-Martin periodinane (51 mg) was added to a solution of (2S,4S)-tert-butyl 4-(4-(bis(tert-butoxycarbonyl)amino)-5-iodo-7H-pyrrolo[2,3-d]pyrimidin-7-yl)-2-(hydroxymethyl)pyrrolidine-1-carboxylate (66 mg) obtained in Step 4 in methylene chloride (2 ml), and the resulting mixture was stirred at room temperature for 1 hour. Dess-Martin periodinane (100 mg) was further added to the mixture, and stirred at room temperature for 1 hour. Dess-Martin periodinane (70 mg) was additionally added thereto, and the resulting mixture was stirred at room temperature for 1 hour. Water was added to the reaction mixture to separate the organic layer. The organic layer was washed with a sodium hydrogen carbonate aqueous solution and a 10% sodium thiosulfate aqueous solution, and dried over anhydrous sodium sulfate. The solvent was distilled off under reduced pressure to obtain the title compound as a light-yellow, amorphous substance (68 mg). Physical properties: m/z[M+H]$^+$ 658.1.

(Step 6) Synthesis of (2S,4S)-tert-butyl 4-(4-(bis(tert-butoxycarbonyl)amino)-5-iodo-7H-pyrrolo[2,3-d]pyrimidin-7-yl)-2-((dimethylamino)methyl)pyrrolidine-1-carboxylate A 1M dimethylamine THF solution (0.3 ml) and acetic acid (0.2 ml) were added to a solution of (2S,4S)-tert-butyl 4-(4-(bis(tert-butoxycarbonyl)amino)-5-iodo-7H-pyrrolo[2,3-d]pyrimidin-7-yl)-2-formylpyrrolidine-1-carboxylate (68 mg) obtained in Step 5 in methylene chloride (2 ml), and the resulting mixture was cooled to 0° C. Sodium triacetoxyborohydride (127 mg) was added to the reaction mixture, and stirred at 0° C. for 2 hours. The reaction mixture was neutralized using a sodium hydrogen carbonate aqueous solution, and the organic layer was dried over anhydrous sodium sulfate. The solvent was distilled off under reduced pressure to obtain the title compound as a light-yellow, amorphous substance (31.9 mg). Physical properties: m/z[M+H]$^+$ 687.2.

(Step 7) Synthesis of (2S,4S)-tert-butyl 4-(4-(bis(tert-butoxycarbonyl)amino)-5-((3,5-dimethoxyphenyl)ethynyl)-7H-pyrrolo[2,3-d]pyrimidin-7-yl)-2-((dimethylamino)methyl)pyrrolidine-1-carboxylate In accordance with Example 1 (Step 1), except that the (2S,4S)-tert-butyl 4-(4-(bis(tert-butoxycarbonyl)amino)-5-iodo-7H-pyrrolo[2,3-d]pyrimidin-7-yl)-2-((dimethylamino)methyl)pyrrolidine-1-carboxylate obtained in Step 6 was used in place of 3-iodo-1H-pyrazolo[3,4-d]pyrimidin-4-amine, the title compound was obtained as a light-yellow, amorphous substance. Physical properties: m/z[M+H]$^+$ 721.5.

(Step 8) Synthesis of 5-((3,5-dimethoxyphenyl)ethynyl)-7-((3S,5S)-5-((dimethylamino)methyl)pyrrolidin-3-yl)-7H-pyrrolo[2,3-d]pyrimidin-4-amine In accordance with Example 66 (Step 7), except that the (2S,4S)-tert-butyl 4-(4-(bis(tert-butoxycarbonyl)amino)-5-((3,5-dimethoxyphenyl)ethynyl)-7H-pyrrolo[2,3-d]pyrimidin-7-yl)-2-((dimethylamino)methyl)pyrrolidine-1-carboxylate obtained in Step 7 was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance. Physical properties: m/z[M+H]$^+$ 421.1.

(Step 9) Synthesis of Example Compound 67

In accordance with Example 66 (Step 8), except that the 5-((3,5-dimethoxyphenyl)ethynyl)-7-((3S,5S)-5-((dimethylamino)methyl)pyrrolidin-3-yl)-7H-pyrrolo[2,3-d]pyrimidin-4-amine obtained in Step 8 was used in place of (2S,4S)-methyl 4-(4-amino-5-((3,5-dimethoxyphenyl)ethynyl)-7H-pyrrolo[2,3-d]pyrimidin-7-)pyrrolidine-2-carboxylate, the title compound was obtained as a colorless, amorphous substance. Table 18 shows the physical properties thereof.

Example 68

Synthesis of 1-((2S,4S)-4-(4-amino-5-((3,5-dimethoxyphenyl)ethynyl)-7H-pyrrolo[2,3-d]pyrimidin-7-yl)-2-(1,3,4-oxadiazol-2-yl)pyrrolidin-1-yl)prop-2-en-1-one (Example Compound 68)

(Step 1) Synthesis of (2S,4S)-4-(4-amino-5-((3,5-dimethoxyphenyl)ethynyl)-7H-pyrrolo[2,3-d]pyrimidin-7-yl)-1-(tert-butoxycarbonyl)pyrrolidine-2-carboxylic acid The (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate (393.8 mg) obtained in Example 66 (Step 6) was dissolved in methanol (6 ml). After cooling to 0° C., 4N aqueous sodium hydroxide (3 ml) was added thereto. The reaction suspension was stirred at room temperature for 3 hours. 5N hydrochloric acid was added to the reaction mixture to a pH of 5, and ethyl acetate and water were added to separate the organic layer. The organic layer was dried over anhydrous magnesium sulfate, and the solvent was distilled off under reduced pressure to obtain the title compound as a light-yellow solid (280 mg). Physical properties: m/z[M+H]$^+$ 508.3.

(Step 2) Synthesis of (2S,4S)-tert-butyl 4-(4-amino-5-((3,5-dimethoxyphenyl)ethynyl)-7H-pyrrolo[2,3-d]pyrimidin-7-yl)-2-(hydrazine carbonyl)pyrrolidine-1-carboxylate DIPEA (73 μl) and hydrazine monohydrate (46 μl) were added to a solution of (2S,4S)-4-(4-amino-5-((3,5-dimethoxyphenyl)ethynyl)-7H-pyrrolo[2,3-d]pyrimidin-7-yl)-1-(tert-butoxycarbonyl)pyrrolidine-2-carboxylic acid (106 mg) obtained in Step 1 above and TBTU (100 mg) in DMF (2 ml), and the resulting mixture was stirred at room temperature for 10 minutes. Ethyl acetate and water were added to the reaction mixture to separate the organic layer, and the organic layer was dried over anhydrous magnesium sulfate. The solvent was distilled off under reduced pressure to obtain the title compound as a light-yellow, amorphous substance (93.6 mg). Physical properties: m/z[M+H]$^+$ 522.4.

(Step 3) Synthesis of (2S,4S)-tert-butyl 4-(4-amino-5-((3,5-dimethoxyphenyl)ethynyl)-7H-pyrrolo[2,3-d]pyrimidin-7-yl)-2-(1,3,4-oxadiazol-2-yl)pyrrolidine-1-carboxylate Toluene (3 ml) and trimethyl orthoformate (79 μl) were added to the (2S,4S)-tert-butyl 4-(4-amino-5-((3,5-dimethoxyphenyl)ethynyl)-7H-pyrrolo[2,3-d]pyrimidin-7-yl)-2-(hydrazine carbonyl)pyrrolidine-1-carboxylate (93.6 mg) obtained in Step 2, and the resulting mixture was stirred at 110° C. overnight. Acetic acid (400 μl) was added to the reaction mixture, and stirred at 110° C. for 6 hours. Ethyl acetate and water were added to the reaction mixture to separate the organic layer. The organic layer was dried over anhydrous magnesium sulfate, and the solvent was distilled off under reduced pressure. The resulting residue was purified by silica gel column chromatography (developing solvent: chloroform/methanol) to obtain the title compound as a light-yellow, amorphous substance (50 mg). Physical properties: m/z [M+H]$^+$ 532.2.

(Step 4) Synthesis of 7-((3S,5S)-5-(1,3,4-oxadiazol-2-yl)pyrrolidin-3-yl)-5-((3,5-dimethoxyphenyl)ethynyl)-7H-pyrrolo[2,3-d]pyrimidin-4-amine In accordance with Example 66 (Step 7), except that the (2S,4S)-tert-butyl 4-(4-amino-5-((3,5-dimethoxyphenyl)ethynyl)-7H-pyrrolo[2,3-d]pyrimidin-7-yl)-2-(1,3,4-oxadiazol-2-yl)pyrrolidine-1-carboxylate (50 mg) obtained in Step 3 was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance (30.3 mg). m/z[M+H]$^+$ 432.0.

(Step 5) Synthesis of Example Compound 68

In accordance with Example 66 (Step 8), except that 7-((3S,5S)-5-(1,3,4-oxadiazol-2-yl)pyrrolidin-3-yl)-5-((3,5-dimethoxyphenyl)ethynyl)-7H-pyrrolo[2,3-d]pyrimidin-4-amine obtained in Step 4 was used in place of (2S,4S)-methyl 4-(4-amino-5-((3,5-dimethoxyphenyl)ethynyl)-7H-pyrrolo[2,3-d]pyrimidin-7-yl)pyrrolidine-2-carboxylate, the title compound was obtained as a light-yellow, amorphous substance. Table 18 shows the physical properties thereof.

Example 69

Synthesis of 1-((2S,4S)-4-(4-amino-5-((3,5-dimethoxyphenyl)ethynyl)-7H-pyrrolo[2,3-d]pyrimidin-7-yl)-2-(5-methyl-1,3,4-oxadiazol-2-yl)pyrrolidin-1-yl)prop-2-en-1-one (Example Compound 69)

(Step 1) Synthesis of (2S,4S)-tert-butyl 4-(4-amino-5-((3,5-dimethoxyphenyl)ethynyl)-7H-pyrrolo[2,3-d]pyrimidin-7-yl)-2-(5-methyl-1,3,4-oxadiazol-2-yl)pyrrolidine-1-carboxylate In accordance with Example 68 (Step 3), except that triethyl orthoacetate was used in place of trimethyl orthoformate, the title compound was obtained as a light-yellow, amorphous substance. Physical properties: m/z[M+H]$^+$ 546.5.

(Step 2) Synthesis of 5-((3,5-dimethoxyphenyl)ethynyl)-7-((3S,5S)-5-(5-methyl-1,3,4-oxadiazol-2-yl)pyrrolidin-3-yl)-7H-pyrrolo[2,3-d]pyrimidin-4-amine In accordance with Example 66 (Step 7), except that the (2S,4S)-tert-butyl 4-(4-amino-5-((3,5-dimethoxyphenyl)ethynyl)-7H-pyrrolo[2,3-d]pyrimidin-7-yl)-2-(5-methyl-1,3,4-oxadiazol-2-yl)pyrrolidine-1-carboxylate obtained in Step 1 was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance. Physical properties: m/z[M+H]$^+$ 466.0.

(Step 3) Synthesis of Example Compound 69

In accordance with Example 66 (Step 8), except that the 5-((3,5-dimethoxyphenyl)ethynyl)-7-((3S,5S)-5-(5-methyl- 1,3,4-oxadiazole-2-yl)pyrrolidin-3-yl)-7H-pyrrolo[2,3-d] pyrimidin-4-amine obtained in Step 2 was used in place of (2S,4S)-methyl 4-(4-amino-5-((3,5-dimethoxyphenyl)ethynyl)-7H-pyrrolo[2,3-d]pyrimidin-7-yl)pyrrolidine-2-carboxylate, the title compound was obtained as a light-yellow, amorphous substance. Table 18 shows the physical properties thereof.

Example 70

Synthesis of 1-((2S,4S)-4-(4-amino-5-((3,5-dimethoxyphenyl)ethynyl)-7H-pyrrolo[2,3-d]pyrimidin-7-yl)-2-(5-((dimethylamino)methyl)-1,3,4-oxadiazole-2-yl)pyrrolidin-1-yl)prop-2-en-1-one (Example Compound 70)

(Step 1) Synthesis of (2S,4S)-tert-butyl 4-(4-amino-5-((3,5-dimethoxyphenyl)ethynyl)-7H-pyrrolo[2,3-d] pyrimidin-7-yl)-2-(2-(2-(dimethylamino)acetyl)hydrazine carbonyl)pyrrolidine-1-carboxylate In accordance with Example 68 (Step 2), except that 2-(dimethylamino)acetohydrazide was used in place of hydrazine monohydrate, the title compound was obtained as a light-yellow, amorphous substance. Physical properties: m/z[M+H]$^+$ 607.3.

(Step 2) Synthesis of (2S,4S)-tert-butyl 4-(4-amino-5-((3,5-dimethoxyphenyl)ethynyl)-7H-pyrrolo[2,3-d] pyrimidin-7-yl)-2-(5-((dimethylamino)methyl)-1,3, 4-oxadiazole-2-yl)pyrrolidine-1-carboxylate DIPEA (105 µl) and tosyl chloride (56 mg) were added to a solution of (2S,4S)-tert-butyl 4-(4-amino-5-((3,5-dimethoxyphenyl)ethynyl)-7H-pyrrolo[2,3-d]pyrimidin-7-yl)-2-(2-(2-(dimethylamino)acetyl)hydrazine carbonyl)pyrrolidine-1-carboxylate (100 mg) obtained in Step 1 in acetonitrile (3 ml), and the mixture was stirred at 40° C. for 1 hour. Ethyl acetate and water were added to the reaction mixture to separate the organic layer. The organic layer was dried over anhydrous magnesium sulfate, and the solvent was distilled off under reduced pressure. The resulting residue was purified by silica gel column chromatography (developing solvent: chloroform/methanol) to obtain the title compound as a light-yellow, amorphous substance (40.5 mg). Physical properties: m/z[M+H]$^+$ 589.2.

Synthesis of (Step 3) 5-((3,5-dimethoxyphenyl) ethynyl)-7-((3S,5S)-5-(5-((dimethylamino)methyl)-1,3,4-oxadiazole-2-yl)pyrrolidin-3-yl)-7H-pyrrolo[2, 3-d]pyrimidin-4-amine In accordance with Example 66 (Step 7), except that the (2S,4S)-tert-butyl 4-(4-amino-5-((3,5-dimethoxyphenyl) ethynyl)-7H-pyrrolo[2,3-d]pyrimidin-7-yl)-2-(5-((dimethylamino)methyl)-1,3,4-oxadiazole-2-yl)pyrrolidine-1-carboxylate obtained in Step (2) was used in place of (2S,4S)-1-tert-butyl 2-methyl 4-(4-amino-5-((3,5-dimethoxyphenyl) ethynyl)-7H-pyrrolo[2,3-d]pyrimidin-7-yl)pyrrolidine-1,2-dicarboxylate, the title compound was obtained as a light-yellow, amorphous substance. Physical properties: m/z[M+H]$^+$ 489.2.

(Step 4) Synthesis of Example Compound 70

In accordance with Example 66 (Step 8), except that the 5-((3,5-dimethoxyphenyl)ethynyl)-7-((3S,5S)-5-(5-((dimethylamino)methyl)-1,3,4-oxadiazole-2-yl)pyrrolidin-3-yl)-7H-pyrrolo[2,3-d]pyrimidin-4-amine obtained in Step 3 was used in place of (2S,4S)-methyl 4-(4-amino-5-((3,5-dimethoxyphenyl)ethynyl)-7H-pyrrolo[2,3-d]pyrimidin-7-yl) pyrrolidine-2-carboxylate, the title compound was obtained as a light-yellow, amorphous substance. Table 19 shows the physical properties thereof.

Example 71

Synthesis of (2S,4S)-1-acryloyl-4-(4-amino-5-((3,5-dimethoxyphenyl)ethynyl)-7H-pyrrolo[2,3-d]pyrimidin-7-yl)-N-(2-(dimethylamino)ethyl)-N-methylpyrrolidine-2-carboxamide (Example Compound 71)

(Step 1) Synthesis of (2S,4S)-tert-butyl 4-(4-amino-5-((3,5-dimethoxyphenyl)ethynyl)-7H-pyrrolo[2,3-d] pyrimidin-7-yl)-2-((2-(dimethylamino)ethyl) (methyl)carbamoyl)pyrrolidine-1-carboxylate A solution of (2S,4S)-4-(4-amino-5-((3,5-dimethoxyphenyl)ethynyl)-7H-pyrrolo[2,3-d]pyrimidin-7-yl)-1-(tert-butoxycarbonyl)pyrrolidine-2-carboxylic acid (25.4 mg) obtained in Example 68 (Step 1), TBTU (17.7 mg), N,N, N'-trimethylethane-1,2-diamine (13 µl), and DIPEA (26 µl) in acetonitrile (3 ml) was stirred at room temperature for 1 hour. Ethyl acetate and water were added to separate the organic layer. The organic layer was dried over anhydrous sodium sulfate, and the solvent was distilled off under reduced pressure. The resulting residue was purified by basic silica gel column chromatography (developing solvent: chloroform/methanol) to obtain the title compound as a light-yellow, amorphous substance (3 mg). Physical properties: m/z[M+H]$^+$ 592.4.

(Step 2) Synthesis of (2S,4S)-4-(4-amino-5-((3,5-dimethoxyphenyl)ethynyl)-7H-pyrrolo[2,3-d]pyrimidin-7-yl)-N-(2-(dimethylamino)ethyl)-N-methylpyrrolidine-2-carboxamide In accordance with Example 66 (Step 7), except that the (2S,4S)-tert-butyl 4-(4-amino-5-((3,5-dimethoxyphenyl) ethynyl)-7H-pyrrolo[2,3-d]pyrimidin-7-yl)-2-((2-(dimethylamino)ethyl)(methyl)carbamoyl)pyrrolidine-1-carboxylate obtained in Step 1 above was used in place of (2S,4S)-1-tert-butyl 2-methyl 4-(4-amino-5-((3,5-dimethoxyphenyl) ethynyl)-7H-pyrrolo[2,3-d]pyrimidin-7-yl)pyrrolidine-1,2-dicarboxylate, the title compound was obtained as a colorless, amorphous substance. Physical properties: m/z [M+H]$^+$ 492.4.

(Step 3) Synthesis of Example Compound 71

In accordance with Example 66 (Step 8), except that the (2S,4S)-4-(4-amino-5-((3,5-dimethoxyphenyl)ethynyl)-7H-pyrrolo[2,3-d]pyrimidin-7-yl)-N-(2-(dimethylamino)ethyl)-N-methylpyrrolidine-2-carboxamide obtained in Step 2 was used in place of (2S,4S)-methyl 4-(4-amino-5-((3,5-dimethoxyphenyl)ethynyl)-7H-pyrrolo[2,3-d]pyrimidin-7-yl) pyrrolidine-2-carboxylate, the title compound was obtained as a colorless, amorphous substance. Table 19 shows the physical properties thereof.

Example 72

Synthesis of 1-(4-((4-amino-5-((3,5-dimethoxyphenyl)ethynyl)-7H-pyrrolo[2,3-d]pyrimidin-7-yl) methyl)piperidin-1-yl)-4-(dimethylamino)but-2-en-1-one (Example Compound 72)

In accordance with Example 38, except that N-Boc-4-hydroxymethylpiperidin was used in place of (R)—N-Boc- 3-pyrrolidinol, the title compound was obtained as a light-yellow, amorphous substance. Table 19 shows the physical properties thereof.

Example 73

Synthesis of (S)-1-(3-(4-amino-3-((3,5-dimethoxyphenyl)ethynyl)-1H-pyrrolo[3,2-c] pyridin-1-yl)pyrrolidin-1-yl)prop-2-en-1-one (Example Compound 73)

(Step 1) Synthesis of 4-chloro-3-iodo-1H-pyrrolo[3,2-c]pyridine

4-Chloro-1H-pyrrolo[3,2-c]pyridine (247 mg) synthesized by the method disclosed in WO2007/095223 was dissolved in DMF (7.0 ml). After cooling to 0° C., N-iodosuccinimide (382 mg) was added thereto. The resulting mixture was stirred at room temperature for 1 hour, and then chloroform and water were added thereto to separate the organic layer. After the organic layer was dried over anhydrous magnesium sulfate, the solvent was distilled off under reduced pressure. The resulting residue was purified by silica gel column chromatography (developing solvent: hexane/ethyl acetate) to obtain the title compound as a dark-brown solid (455 mg). Physical properties: m/z[M+H]$^+$ 279.1.

(Step 2) Synthesis of (S)-tert-butyl 3-(4-chloro-3-iodo-1H-pyrrolo[3,2-c]pyridin-1-yl)pyrrolidine-1-carboxylate The 4-chloro-3-iodo-1H-pyrrolo[3,2-c]pyridine (225 mg) obtained in Step 1 was dissolved in DMF (3.0 ml). After cooling to 0° C., 60% sodium hydride (64.5 mg) was added thereto. The (R)-tert-butyl 3-(methylsulfonyloxy)pyrrolidine-1-carboxylate (322 mg) obtained in Example 2 (Step 1) was added to the reaction mixture using DMF (2.0 ml), and the mixture was stirred overnight. 60% Sodium hydride (64.5 mg) was additionally added, and the mixture was stirred at 85° C. overnight. Ethyl acetate and water were added to the reaction mixture to separate the organic layer. The organic layer was dried over anhydrous magnesium sulfate, and the solvent was distilled off under reduced pressure. The resulting residue was purified by silica gel column chromatography (developing solvent: hexane/ethyl acetate) to obtain the title compound as a crude product (192 mg). Physical properties: m/z[M+H]$^+$ 448.3.

(Step 3) Synthesis of (S)-tert-butyl 3-(4-chloro-3-((3,5-dimethoxyphenyl)ethynyl)-1H-pyrrolo[3,2-c]pyridin-1-yl)pyrrolidine-1-carboxylate PdCl$_2$(dppf)CH$_2$Cl$_2$ (33 mg) was added to a mixture of the crude product of (S)-tert-butyl 3-(4-chloro-3-iodo-1H-pyrrolo[3,2-c]pyridin-1-yl)pyrrolidine-1-carboxylate (180 mg) obtained in Step 2, 1-ethynyl 3,5-dimethoxybenzene (97 mg), copper (I) iodide (15 mg), and triethylamine (1.0 ml) in THF (4.0 ml). After nitrogen purging, the resulting mixture was stirred at 50° C. for 30 minutes. Ethyl acetate and water were added to the reaction mixture to separate the organic layer. After being washed with a saturated sodium chloride solution, the organic layer was dried over anhydrous sodium sulfate, and the solvent was then distilled off under reduced pressure. The resulting residue was purified by silica gel column chromatography (developing solvent: hexane/ethyl acetate) to obtain the title compound as a colorless, amorphous substance (133 mg). Physical properties: m/z[M+H]$^+$ 482.4.

(Step 4) Synthesis of (S)-tert-butyl 3-(4-amino-3-((3,5-dimethoxyphenyl)ethynyl)-1H-pyrrolo[3,2-c]pyridin-1-yl)pyrrolidine-1-carboxylate Under a nitrogen atmosphere, the (S)-tert-butyl 3-(4-chloro-3-((3,5-dimethoxyphenyl)ethynyl)-1H-pyrrolo[3,2-c]pyridin-1-yl)pyrrolidine-1-carboxylate (120 mg) obtained in Step 3, 2,2'-bis(diphenylphosphino)-1,1'-binaphthalene (BINAP) (26 mg), sodium tert-butoxide (72 mg), benzophenone imine (92 mg), and tris (dibenzylideneacetone)dipalladium (36 mg) were suspended in toluene (10 ml), and the result was stirred at 115° C. for 90 minutes. After dilution with ethyl acetate, celite filtration was performed. The solvent was distilled off under reduced pressure. Hydroxyaminehydrochloride (366 mg), sodium bicarbonate (442 mg), methanol (16 ml), and water (4 ml) were added to the resulting residue, and the resulting mixture was stirred at room temperature for 2 hours. The solvent was distilled off under reduced pressure. Thereafter, ethyl acetate and a saturated sodium chloride solution were added to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (35 mg). Physical properties: m/z[M+H]$^+$ 463.4.

(Step 5) Synthesis of Example Compound 73

In accordance with Example 1 (Step 4), except that the (S)-tert-butyl 3-(4-amino-3-((3,5-dimethoxyphenyl)ethynyl)-1H-pyrrolo[3,2-c]pyridin-1-yl)pyrrolidine-1-carboxylate obtained in Step (3) was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 19 shows the physical properties thereof.

Reference Example 1

Synthesis of (R)-1-(3-(4-amino-3-(4-phenoxyphenyl)-1H-pyrazolo[3,4-d]pyrimidin-1-yl)piperidin-1-yl)prop-2-en-1-one (Reference Example Compound 1)

The compound was synthesized according to the method disclosed in WO2008/121742. Table 20 shows the physical properties thereof.

Reference Example 2

Synthesis of 3-cyclobutyl-1-(phenylethynyl)imidazo[1,5-a]pyrazin-8-amine (Reference Example Compound 2)

The compound was synthesized according to the method disclosed in WO2007/087395. Table 20 shows the physical properties thereof.

Reference Example 3

Synthesis of (S)-1-(3-(4-amino-3-((3,5-dimethoxyphenyl)ethynyl)-1H-pyrazolo[3,4-d]pyrimidin-1-yl)pyrrolidin-1-yl)propan-1-one (Reference Example Compound 3)

In accordance with Example 1, (S)-3-((3,5-dimethoxyphenyl)ethynyl)-1-(pyrrolidin-3-yl)-1H-pyrazolo[3,4-d]pyrimidin-4-amine and propionyl chloride were used to obtain the title compound as a white solid. Table 20 shows the physical properties thereof.

Reference Example 4

Synthesis of (S)-1-(3-(4-amino-3-((3,5-diisopropylphenyl)ethynyl)-1H-pyrazolo[3,4-d]pyrimidin-1-yl)pyrrolidin-1-yl)-4-(dimethylamino)but-2-en-1-one (Reference Example Compound 4)

(Step 1) Synthesis of 1-ethynyl-3,5-diisopropylbenzene

PdCl$_2$(dppf)CH$_2$Cl$_2$ (163 mg) was added to a mixture of trimethylsilylacetylene (589 mg), 1-bromo-3,5-diisopropylbenzene (480 mg), copper (I) iodide (76 mg), and triethylamine (0.11 ml) in THF (4 ml). After nitrogen purging, the resulting mixture was stirred at 80° C. for 4 hours. Ethyl acetate and water were added to the reaction mixture to separate the organic layer. After drying the result over anhydrous sodium sulfate, the solvent was distilled off under reduced pressure. A 2% potassium hydroxide methanol solution (10 ml) was added to the resulting residue, and the result was stirred at room temperature overnight. Chloroform and water were added to the reaction mixture to separate the organic layer. After drying the result over anhydrous sodium sulfate, the solvent was distilled off under reduced pressure. The resulting residue was purified by silica gel column chromatography (developing solvent: hexane) to obtain the title compound as a yellow, oily substance (181 mg).

(Step 2) Synthesis of (S)-tert-butyl 3-(4-amino-3-iodo-1H-pyrazolo[3,4-d]pyrimidin-1-yl)pyrrolidine-1-carboxylate A suspension of 3-iodo-1H-pyrazolo[3,4-d]pyrimidin-4-amine (446 mg), (R)-tert-butyl 3-(methylsulfonyloxy)pyrrolidine-1-carboxylate (450 mg), potassium carbonate (692 mg) in DMF (5.0 ml) was stirred at 85° C. for 6 hours. Ethyl acetate and water were added thereto to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a light-yellow, amorphous substance (354 mg). Physical properties: m/z [M+H]$^+$ 431.1.

(Step 3) Synthesis of (S)-tert-butyl 3-(4-amino-3-((3,5-diisopropylphenyl)ethynyl)-1H-pyrazolo[3,4-d]pyrimidin-1-yl)pyrrolidine-1-carboxylate PdCl$_2$(dppf)CH$_2$Cl$_2$ (8.2 mg) was added to a mixture of 1-ethynyl-3,5-diisopropylbenzene (56 mg) obtained in Step 1, (S)-tert-butyl 3-(4-amino-3-iodo-1H-pyrazolo[3,4-d]pyrimidin-1-yl)pyrrolidine-1-carboxylate (43 mg) obtained in Step 2, copper (I) iodide (3.8 mg), and triethylamine (0.2 ml) in THF (2.0 ml). After nitrogen purging, the resulting mixture was stirred at 80° C. for 1.5 hours. Ethyl acetate and water were added to the reaction mixture to separate the organic layer. The organic layer was washed with a saturated sodium chloride solution. After drying the result over anhydrous sodium sulfate, the solvent was distilled off under reduced pressure. The resulting residue was purified by basic silica gel column chromatography (developing solvent: hexane/ethyl acetate) to obtain the title compound as a colorless, amorphous substance (42 mg). Physical properties: m/z[M+H]$^+$ 489.2.

(Step 4) Synthesis of (S)-3-((3,5-diisopropylphenyl)ethynyl)-1-(pyrrolidin-3-yl)-1H-pyrazolo[3,4-d]pyrimidin-4-amine In accordance with Example 66 (Step 7), except that the (S)-tert-butyl 3-(4-amino-3-((3,5-diisopropylphenyl)ethynyl)-1H-pyrazolo[3,4-d]pyrimidin-1-yl)pyrrolidine-1-carboxylate obtained in Step (3) was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance.

(Step 5) Synthesis of Reference Example Compound 4

In accordance with Example 4, except that the (S)-3-((3,5-diisopropylphenyl)ethynyl)-1-(pyrrolidin-3-yl)-1H-pyrazolo[3,4-d]pyrimidin-4-amine obtained in Step (4) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 20 shows the physical properties thereof.

Reference Example 5

Synthesis of (S)-1-(3-(4-amino-3-((3-methoxyphenyl)ethynyl)-1H-pyrazolo[3,4-d]pyrimidin-1-yl)pyrrolidin-1-yl)-4-(dimethylamino)but-2-en-1-one (Reference Example Compound 5)

(Step 1) Synthesis of (S)-1-(3-(4-amino-3-iodo-1H-pyrazolo[3,4-d]pyrimidin-1-yl)pyrrolidin-1-yl)-4-(dimethylamino)but-2-en-1-one 4N-Hydrochloric acid/1,4-dioxane (4 ml) was added to the (S)-tert-butyl 3-(4-amino-3-iodo-1H-pyrazolo[3,4-d]pyrimidin-1-yl)pyrrolidine-1-carboxylate (488 mg) obtained in Reference Example 4 (Step 2), and the resulting mixture was stirred for 1 hour. The solvent was distilled off under reduced pressure. A solution of 4-(dimethylamino)but-2-enoic-acid hydrochloride (281 mg) and HATU (647 mg) in DMF (5.0 ml) was added to the resulting residue. Further, DIPEA (0.78 ml) was added thereto, and the mixture was stirred overnight. The reaction mixture was concentrated under reduced pressure, and chloroform (50 ml) and ethanol (50 ml) were added to the resulting residue. The insoluble matter was removed by filtration, and the filtrate was concentrated under reduced pressure. The resulting residue was washed with ethyl acetate (5.0 ml) and dried to obtain the crude product of the title compound (458 mg). Physical properties: m/z[M+H]$^+$ 442.0.

(Step 2) Synthesis of Reference Example Compound 5

PdCl$_2$(dppf)CH$_2$Cl$_2$ (1.3 mg) was added to a mixture of (S)-1-(3-(4-amino-3-iodo-1H-pyrazolo[3,4-d]pyrimidin-1-yl)pyrrolidin-1-yl)-4-(dimethylamino)but-2-en-1-one (8.0 mg) obtained in Step 1, 1-ethynyl-3-methoxybenzene (4.0 mg), copper (I) iodide (0.6 mg), and triethylamine (8.6 μl) in THF (1.0 ml). After nitrogen purging, the resulting mixture was stirred at 80° C. overnight. The reaction mixture was diluted with ethyl acetate and methanol. The resulting diluted solution was treated with basic silica gel, and then concentrated. The resulting residue was purified by reversed-phase HPLC purification (water/acetonitrile (0.1% formic acid)) to obtain the title compound as a colorless, amorphous substance (1.4 mg). Table 20 shows the physical properties thereof.

Reference Example 6

Synthesis of (S)—N-(3-((4-amino-1-(1-(4-(dimethylamino)but-2-enoyl)pyrrolidin-3-yl)-1H-pyrazolo[3,4-d]pyrimidin-3-yl)ethynyl)phenyl)acetamide (Reference Example Compound 6)

In accordance with Reference Example 5, except that N-(3-ethynylphenyl)acetamide was used in place of 1-ethynyl-3-methoxybenzene, the title compound was obtained as a colorless, amorphous substance. Table 20 shows the physical properties thereof.

Reference Example 7

Synthesis of (S)-1-(3-(4-amino-3-(pyridin-3-ylethynyl)-1H-pyrazolo[3,4-d]pyrimidin-1-yl)pyrrolidin-1-yl)-4-(dimethylamino)but-2-en-1-one (Reference Example Compound 7)

In accordance with Reference Example 5, 3-ethynyl pyridine was used in place of 1-ethynyl-3-methoxybenzene, the title compound was obtained as a colorless, amorphous substance. Table 20 shows the physical properties thereof.

TABLE 1

| Ex. Comp | Structural formula | Physical properties |
|---|---|---|
| 1 | 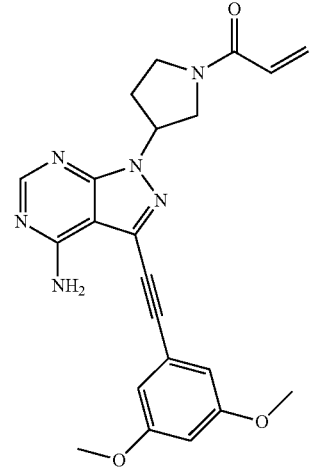 [SMILES: C=CC(=O)N1CCC(n2nc(C#Cc3cc(OC)cc(OC)c3)c3c(N)ncnc32)C1] | 1H-NMR (DMSO-d6) δ: 2.29-2.50 (2H, m), 3.55-4.10 (4H, m), 3.77 (6H, s), 5.40-5.55 (1H, m), 5.62-5.72 (1H, m), 6.10-6.20 (1H, m), 6.50-6.70 (1H, m), 6.64 (1H, d, J = 2.3 Hz), 6.90 (2H, d, J = 2.3 Hz), 8.26 (1H, s). m/z [M + H]$^+$ 419.0 |
| 2 | 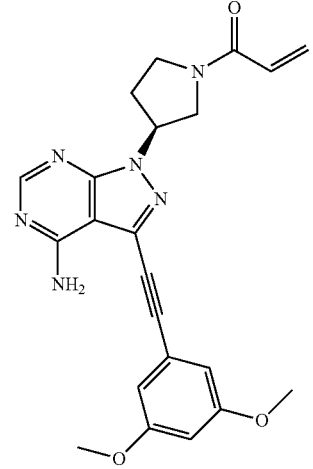 [SMILES: C=CC(=O)N1CC[C@H](n2nc(C#Cc3cc(OC)cc(OC)c3)c3c(N)ncnc32)C1] | 1H-NMR (DMSO-d6) δ: 2.29-2.50 (2H, m), 3.55-4.10 (4H, m), 3.77 (6H, s), 5.40-5.55 (1H, m), 5.62-5.72 (1H, m), 6.10-6.20 (1H, m), 6.50-6.70 (1H, m), 6.64 (1H, d, J = 2.3 Hz), 6.90 (2H, d, J = 2.3 Hz), 8.26 (1H, s). m/z [M + H]$^+$ 419.0 |

TABLE 1-continued
| Ex. Comp | Structural formula | Physical properties |
|---|---|---|
| 3 | 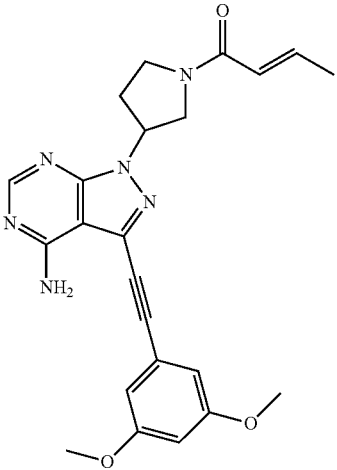 [SMILES: C/C=C/C(=O)N1CCC(n2nc(C#Cc3cc(OC)cc(OC)c3)c3c(N)ncnc32)C1] | 1H-NMR (DMSO-d6) δ: 1.81 (1.5H, dd, J = 6.8, 1.6 Hz), 1.85 (1.5H, dd, J = 6.8, 1.6 Hz), 2.29-2.50 (2H, m), 3.56-3.92 (3.5H, m), 3.77 (6H, s), 4.02-4.10 (0.5H, m), 5.42-5.53 (1H, m), 6.26 (0.5H, dd, J = 15.1, 1.6 Hz), 6.34 (0.5H, dd, J = 15.1, 1.6 Hz), 6.60 (1H, t, J = 2.4 Hz), 6.64-6.74 (1H, m), 6.91 (2H, d, J = 2.4 Hz), 8.25 (0.5H, S), 8.27 (0.5H, S). m/z [M + H]$^+$ 433.1 |
| 4 | 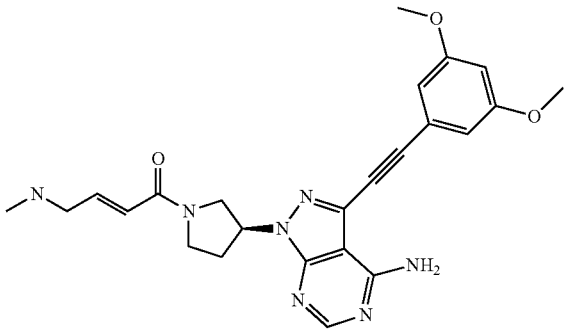 | 1H-NMR (DMSO-d6) δ: 2.05 (3H, s), 2.09 (3H, s), 2.20-2.45 (2H, m), 2.95 (1H, d, J = 5.9 Hz), 2.99 (1H, d, J = 5.9 Hz), 3.30-4.10 (4H, m), 5.30-5.50 (1H, m), 6.29 (0.5H, d, J = 15.0 Hz), 6.38 (0.5H, d, J = 15.0 Hz) 6.53-6.65 (3H, m), 6.84 (2H, s), 8.12 (1H, s). m/z [M + H]$^+$ 476.1 |
TABLE 2
| 5 | 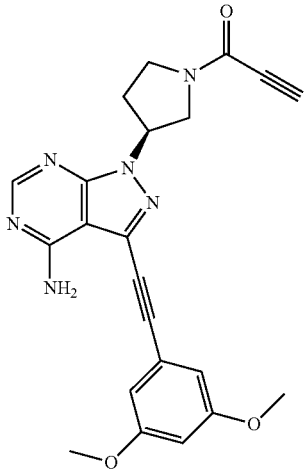 [SMILES: C#CC(=O)N1CC[C@H](n2nc(C#Cc3cc(OC)cc(OC)c3)c3c(N)ncnc32)C1] | m/z [M + H]$^+$ 417.0 |
|---|---|---|

TABLE 2-continued
| | | |
|---|---|---|
| 6 | 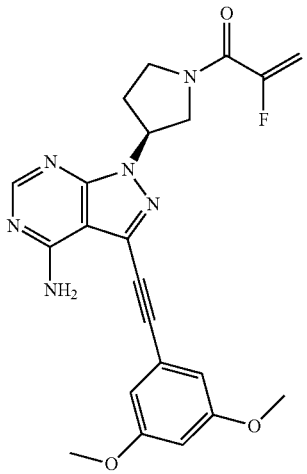 [SMILES: C=C(F)C(=O)N1CC[C@H](n2nc(C#Cc3cc(OC)cc(OC)c3)c3c(N)ncnc32)C1] | 1H-NMR (CDCl3) δ: 2.37-2.68 (2H, m), 3.74-3.82 (2H, m), 3.82 (6H, s), 4.07-4.21 (2H, m), 5.11-5.19 (1H, m), 5.50-5.56 (1H, m), 5.58 (1H, t, J = 46.8, 2.0 Hz), 5.85 (2H, s), 6.54 (1H, t, J = 2.0 Hz), 6.74 (2H, d, J = 2.4 Hz), 8.37 (1H, s)<br>m/z [M + H]+ 437.2 |
| 7 | 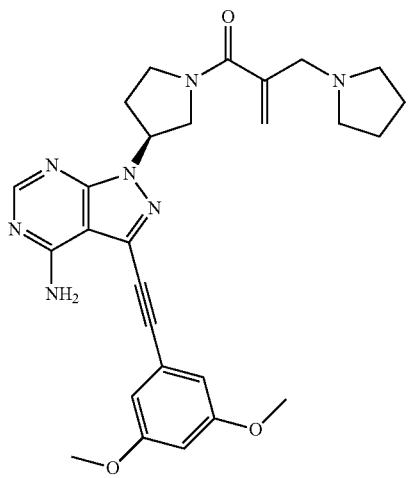 [SMILES: C=C(CN1CCCC1)C(=O)N1CC[C@H](n2nc(C#Cc3cc(OC)cc(OC)c3)c3c(N)ncnc32)C1] | 1H-NMR (CDCl3) δ: 1.70-1.80 (4H, m), 2.42-2.66 (6H, m), 3.20-3.32 (1H, m), 3.40-3.46 (1H, m), 3.76-3.82 (2H, m), 3.82 (6H, s), 3.91-4.15 (3H, m), 5.32-5.56 (3H, m), 5.91 (2H, s), 6.54 (1H, t, J = 2.0 Hz), 6.73 (2H, d, J = 2.4 Hz), 8.36 (1H, s)<br>m/z [M + H]+ 502.2 |
| 8 | 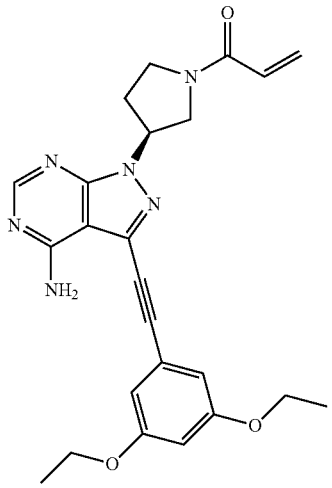 [SMILES: C=CC(=O)N1CC[C@H](n2nc(C#Cc3cc(OCC)cc(OCC)c3)c3c(N)ncnc32)C1] | 1H-NMR (CDCl3) δ: 1.42 (6H, t, J = 6.8 Hz), 2.39-2.72 (2H, m), 3.71-3.84 (1H, m), 3.96-4.12 (3H, m), 4.03 (4H, q, J = 6.8 Hz), 5.48-5.76 (2H, m), 5.84 (2H, br s), 6.38-6.56 (3H, m), 6.70-6.73 (2H, m), 8.36-8.38 (3H, m).<br>m/z [M + H]+ 447.2 |

TABLE 2-continued
| 9 | 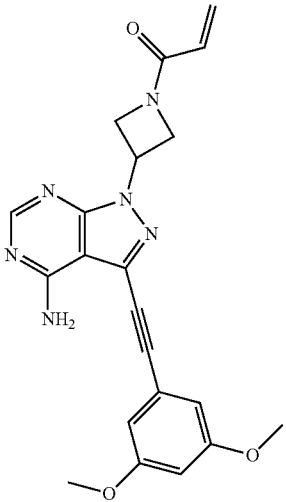 | 1H-NMR (DMSO-d6) δ: 3.78 (6H, s), 4.20-4.35 (1H, m), 4.40-4.50 (1H, m), 4.55-4.65 (1H, m), 4.70-4.80 (1H, m), 5.70-5.80 (2H, m), 6.16 (1H, dd, J = 17.1, 2.1 Hz), 6.38 (1H, dd, J = 17.1, 10.2 Hz), 6.61 (1H, t, J = 2.4 Hz), 6.94 (2H, d, J = 2.4 Hz), 8.26 (1H, s).<br>m/z [M + H]⁺ 405.1 |
TABLE 3
| 10 | 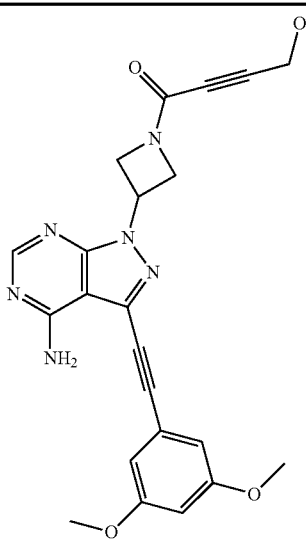 | 1H-NMR (DMSO-d6) δ: 3.73 (6H, s), 4.12-4.28 (3H, m), 4.35-4.50 (2H, m), 4.55-4.65 (1H, m), 5.55 (1H, brs), 5.67 (1H, brs), 6.56 (1H, s), 6.87 (2H, s), 8.40 (1H, s).<br>m/z [M + H]⁺ 433.3 |
| 11 | 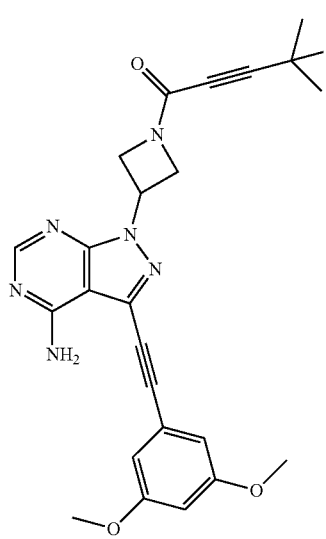 | 1H-NMR (DMSO-d6) δ: 1.32 (6H, s), 3.70 (6H, s), 4.14-4.19 (1H, m), 4.33-4.44 (2H, m), 4.57 (1H, t, J = 9.3 Hz), 5.61-5.70 (2H, m), 6.53 (1H, s), 6.87 (2H, d, J = 2.2 Hz), 8.18 (1H, s).<br>m/z [M + H]⁺ 461.4 |

TABLE 3-continued
| 12 | 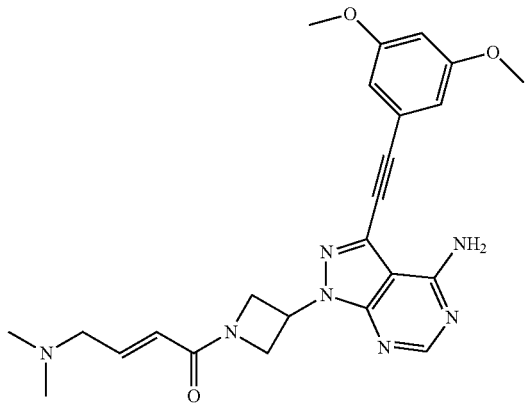 | 1H-NMR (DMSO-d6) δ: 2.08 (6H, s), 2.97 (2H, d, J = 6.2 Hz), 3.72 (6H, d, J = 3.7 Hz), 4.15-4.25 (1H, m), 4.30-4.48 (2H, m), 4.67 (1H, t, J = 9.0 Hz), 5.60-5.70 (1H, m), 6.11 (1H, d, J = 15.0 Hz), 6.55-6.61 (2H, m), 6.88 (2H, d, J = 1.8 Hz), 8.20 (1H, s).<br>m/z [M + H]⁺ 462.1 |
|---|---|---|
| 13 | 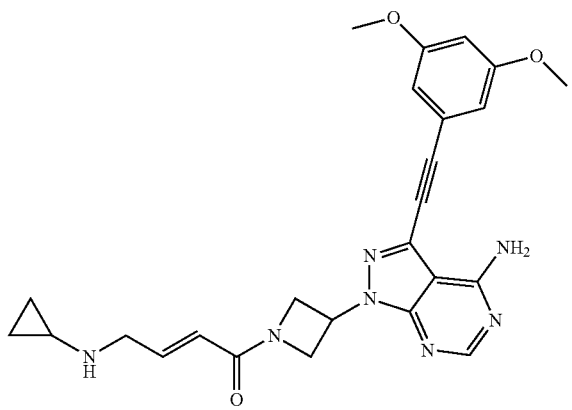 [SMILES: COc1cc(C#Cc2nn(C3CN(C(=O)/C=C/CNC4CC4)C3)c3ncnc(N)c23)cc(OC)c1] | 1H-NMR (DMSO-d6) δ: 0.00-0.03 (2H, m), 0.12-0.18 (2H, m), 1.84-1.90 (1H, m), 3.59 (6H, s), 4.04-4.09 (1H, m), 4.22 (1H, t, J = 9.3 Hz), 4.32-4.38 (1H, m), 4.52 (1H, t, J = 8.4 Hz), 5.48-5.54 (1H, m), 5.93 (1H, d, J = 15.4 Hz), 6.41 (1H, t, J = 2.3 Hz), 6.54 (1H, dt, J = 15.4, 5.5 Hz), 6.75 (2H, d, J = 2.3 Hz), 8.07 (1H, s).<br>m/z [M + H]⁺ 474.2 |
TABLE 4
| 14 | 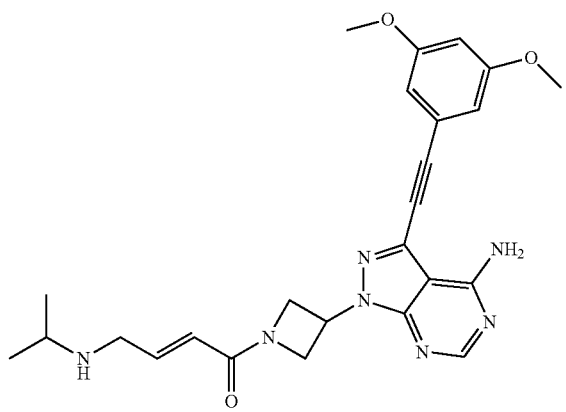 [SMILES: COc1cc(C#Cc2nn(C3CN(C(=O)/C=C/CNC(C)C)C3)c3ncnc(N)c23)cc(OC)c1] | 1H-NMR (DMSO-d6) δ: 0.98 (6H, d, J = 6.2 Hz), 2.70-2.76 (1H, m), 3.79 (6H, s), 4.24-4.29 (1H, m), 4.43 (1H, t, J = 9.3 Hz), 4.54-4.58 (1H, m), 4.72 (1H, t, J = 8.6 Hz), 5.70-5.74 (1H, m), 6.17 (1H, d, J = 15.4 Hz), 6.61 (1H, t, J = 2.5 Hz), 6.68-6.80 (1H, m), 6.95 (2H, d, J = 2.5 Hz), 8.33 (1H, s).<br>m/z [M + H]⁺ 476.2 |
|---|---|---|

TABLE 4-continued
| 15 | 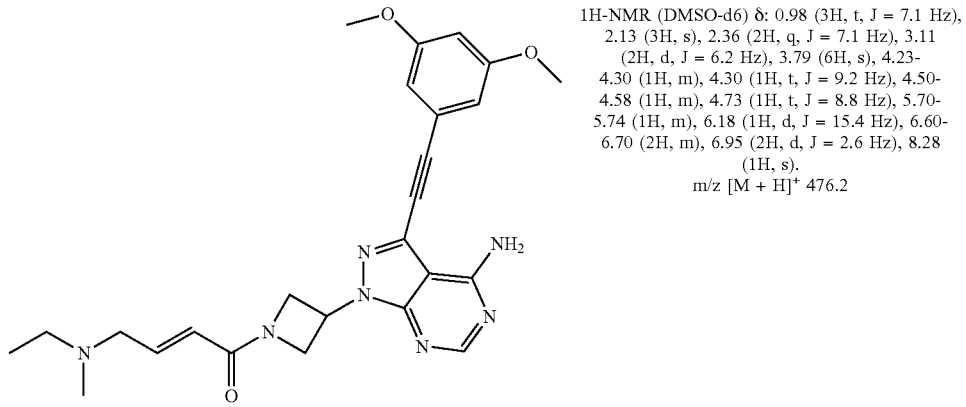 | 1H-NMR (DMSO-d6) δ: 0.98 (3H, t, J = 7.1 Hz), 2.13 (3H, s), 2.36 (2H, q, J = 7.1 Hz), 3.11 (2H, d, J = 6.2 Hz), 3.79 (6H, s), 4.23-4.30 (1H, m), 4.30 (1H, t, J = 9.2 Hz), 4.50-4.58 (1H, m), 4.73 (1H, t, J = 8.8 Hz), 5.70-5.74 (1H, m), 6.18 (1H, d, J = 15.4 Hz), 6.60-6.70 (2H, m), 6.95 (2H, d, J = 2.6 Hz), 8.28 (1H, s). m/z [M + H]$^+$ 476.2 |
|---|---|---|
| 16 | 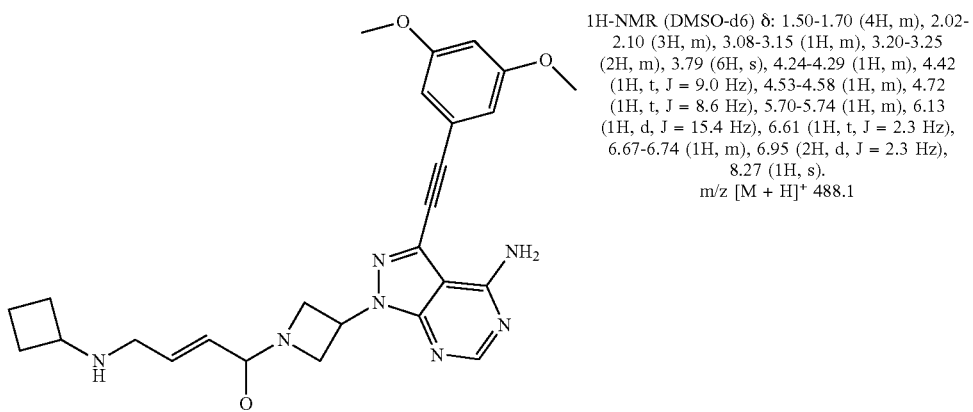 | 1H-NMR (DMSO-d6) δ: 1.50-1.70 (4H, m), 2.02-2.10 (3H, m), 3.08-3.15 (1H, m), 3.20-3.25 (2H, m), 3.79 (6H, s), 4.24-4.29 (1H, m), 4.42 (1H, t, J = 9.0 Hz), 4.53-4.58 (1H, m), 4.72 (1H, t, J = 8.6 Hz), 5.70-5.74 (1H, m), 6.13 (1H, d, J = 15.4 Hz), 6.61 (1H, t, J = 2.3 Hz), 6.67-6.74 (1H, m), 6.95 (2H, d, J = 2.3 Hz), 8.27 (1H, s). m/z [M + H]$^+$ 488.1 |
TABLE 5
| 17 | 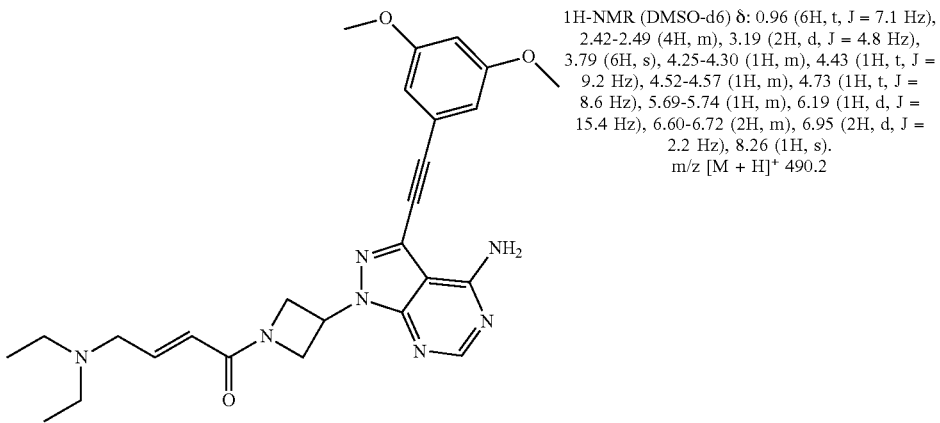 | 1H-NMR (DMSO-d6) δ: 0.96 (6H, t, J = 7.1 Hz), 2.42-2.49 (4H, m), 3.19 (2H, d, J = 4.8 Hz), 3.79 (6H, s), 4.25-4.30 (1H, m), 4.43 (1H, t, J = 9.2 Hz), 4.52-4.57 (1H, m), 4.73 (1H, t, J = 8.6 Hz), 5.69-5.74 (1H, m), 6.19 (1H, d, J = 15.4 Hz), 6.60-6.72 (2H, m), 6.95 (2H, d, J = 2.2 Hz), 8.26 (1H, s). m/z [M + H]$^+$ 490.2 |
|---|---|---|

TABLE 5-continued
| 18 | 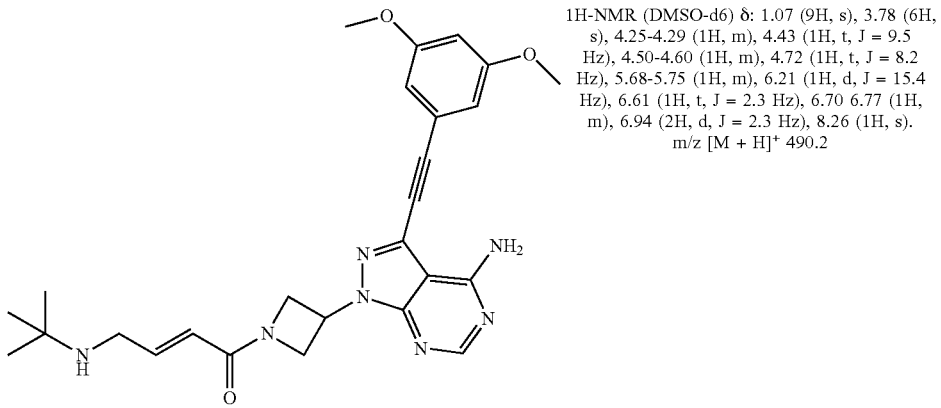 | 1H-NMR (DMSO-d6) δ: 1.07 (9H, s), 3.78 (6H, s), 4.25-4.29 (1H, m), 4.43 (1H, t, J = 9.5 Hz), 4.50-4.60 (1H, m), 4.72 (1H, t, J = 8.2 Hz), 5.68-5.75 (1H, m), 6.21 (1H, d, J = 15.4 Hz), 6.61 (1H, t, J = 2.3 Hz), 6.70 6.77 (1H, m), 6.94 (2H, d, J = 2.3 Hz), 8.26 (1H, s). m/z [M + H]⁺ 490.2 |
|---|---|---|
| 19 | 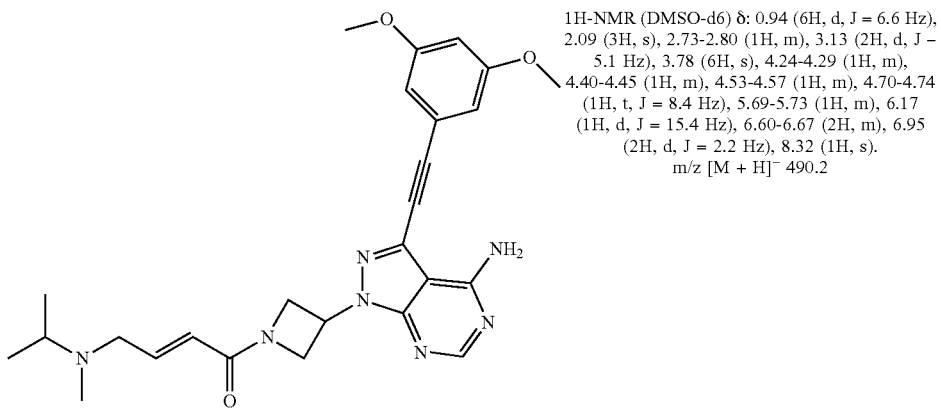 | 1H-NMR (DMSO-d6) δ: 0.94 (6H, d, J = 6.6 Hz), 2.09 (3H, s), 2.73-2.80 (1H, m), 3.13 (2H, d, J = 5.1 Hz), 3.78 (6H, s), 4.24-4.29 (1H, m), 4.40-4.45 (1H, m), 4.53-4.57 (1H, m), 4.70-4.74 (1H, t, J = 8.4 Hz), 5.69-5.73 (1H, m), 6.17 (1H, d, J = 15.4 Hz), 6.60-6.67 (2H, m), 6.95 (2H, d, J = 2.2 Hz), 8.32 (1H, s). m/z [M + H]⁻ 490.2 |
| 20 | 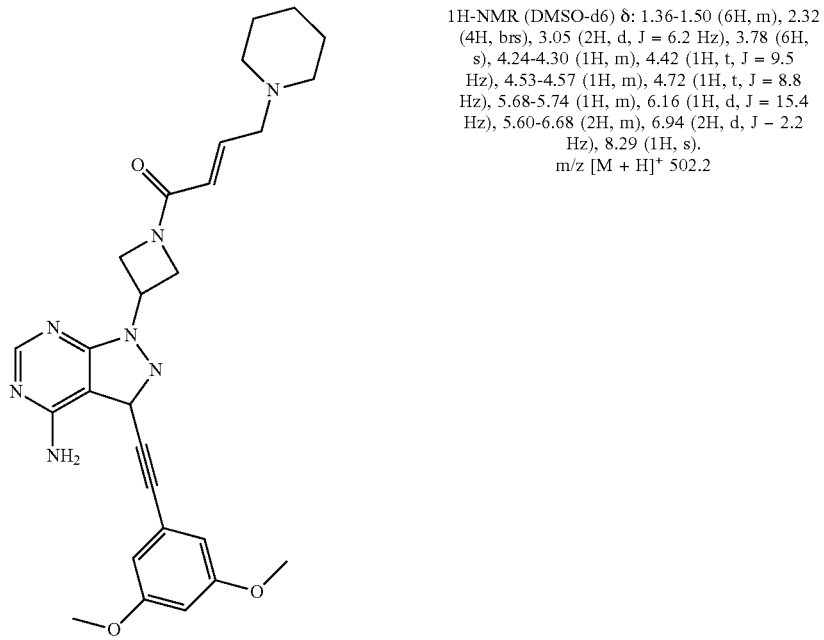 | 1H-NMR (DMSO-d6) δ: 1.36-1.50 (6H, m), 2.32 (4H, brs), 3.05 (2H, d, J = 6.2 Hz), 3.78 (6H, s), 4.24-4.30 (1H, m), 4.42 (1H, t, J = 9.5 Hz), 4.53-4.57 (1H, m), 4.72 (1H, t, J = 8.8 Hz), 5.68-5.74 (1H, m), 6.16 (1H, d, J = 15.4 Hz), 5.60-6.68 (2H, m), 6.94 (2H, d, J = 2.2 Hz), 8.29 (1H, s). m/z [M + H]⁺ 502.2 |

TABLE 6
| 21 | 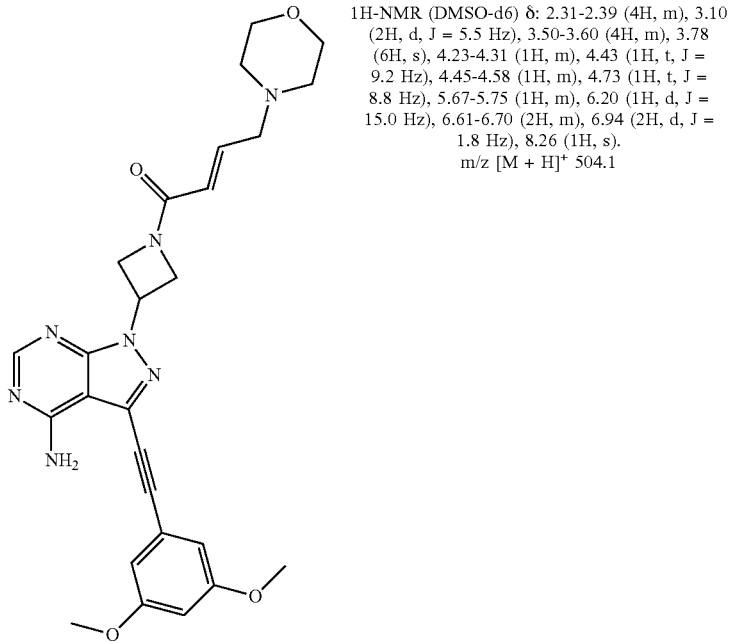 | 1H-NMR (DMSO-d6) δ: 2.31-2.39 (4H, m), 3.10 (2H, d, J = 5.5 Hz), 3.50-3.60 (4H, m), 3.78 (6H, s), 4.23-4.31 (1H, m), 4.43 (1H, t, J = 9.2 Hz), 4.45-4.58 (1H, m), 4.73 (1H, t, J = 8.8 Hz), 5.67-5.75 (1H, m), 6.20 (1H, d, J = 15.0 Hz), 6.61-6.70 (2H, m), 6.94 (2H, d, J = 1.8 Hz), 8.26 (1H, s).<br>m/z [M + H]+ 504.1 |
|---|---|---|
| 22 | 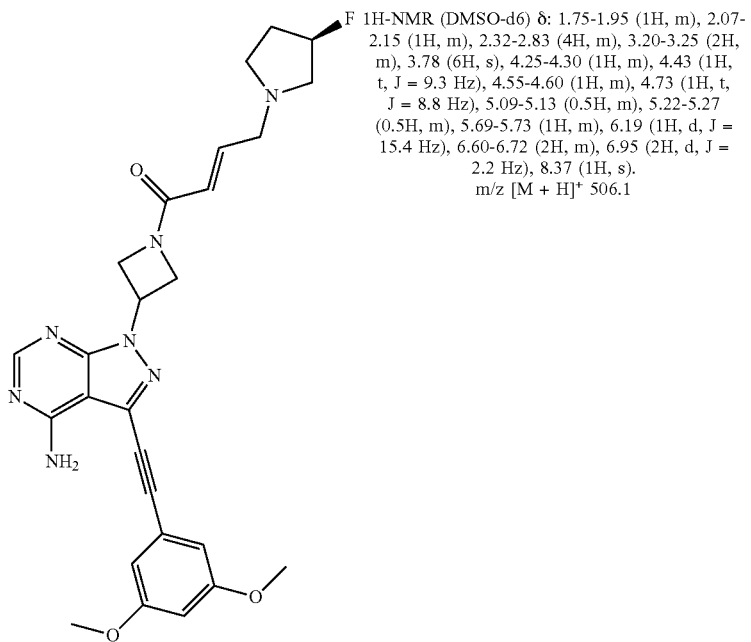 | 1H-NMR (DMSO-d6) δ: 1.75-1.95 (1H, m), 2.07-2.15 (1H, m), 2.32-2.83 (4H, m), 3.20-3.25 (2H, m), 3.78 (6H, s), 4.25-4.30 (1H, m), 4.43 (1H, t, J = 9.3 Hz), 4.55-4.60 (1H, m), 4.73 (1H, t, J = 8.8 Hz), 5.09-5.13 (0.5H, m), 5.22-5.27 (0.5H, m), 5.69-5.73 (1H, m), 6.19 (1H, d, J = 15.4 Hz), 6.60-6.72 (2H, m), 6.95 (2H, d, J = 2.2 Hz), 8.37 (1H, s).<br>m/z [M + H]+ 506.1 |

TABLE 6-continued
| 23 | 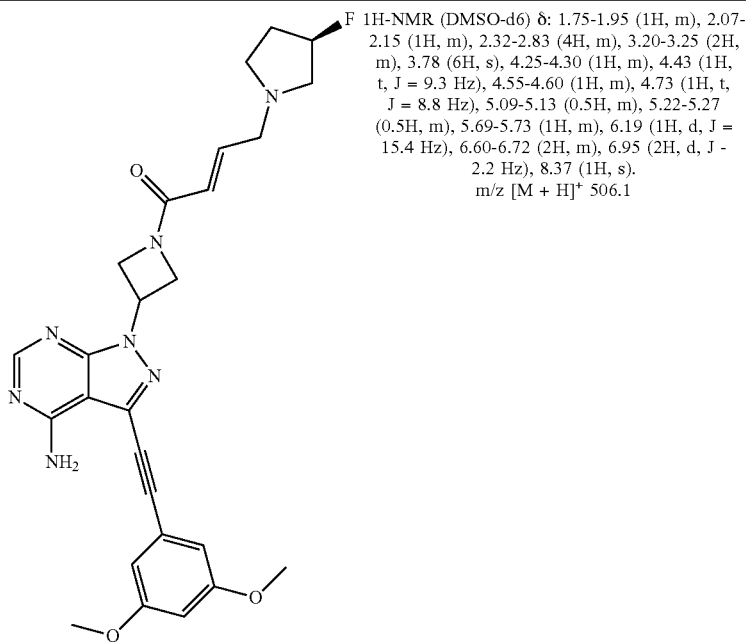 | F 1H-NMR (DMSO-d6) δ: 1.75-1.95 (1H, m), 2.07-2.15 (1H, m), 2.32-2.83 (4H, m), 3.20-3.25 (2H, m), 3.78 (6H, s), 4.25-4.30 (1H, m), 4.43 (1H, t, J = 9.3 Hz), 4.55-4.60 (1H, m), 4.73 (1H, t, J = 8.8 Hz), 5.09-5.13 (0.5H, m), 5.22-5.27 (0.5H, m), 5.69-5.73 (1H, m), 6.19 (1H, d, J = 15.4 Hz), 6.60-6.72 (2H, m), 6.95 (2H, d, J - 2.2 Hz), 8.37 (1H, s).<br>m/z [M + H]⁺ 506.1 |
|---|---|---|
TABLE 7
| 24 | 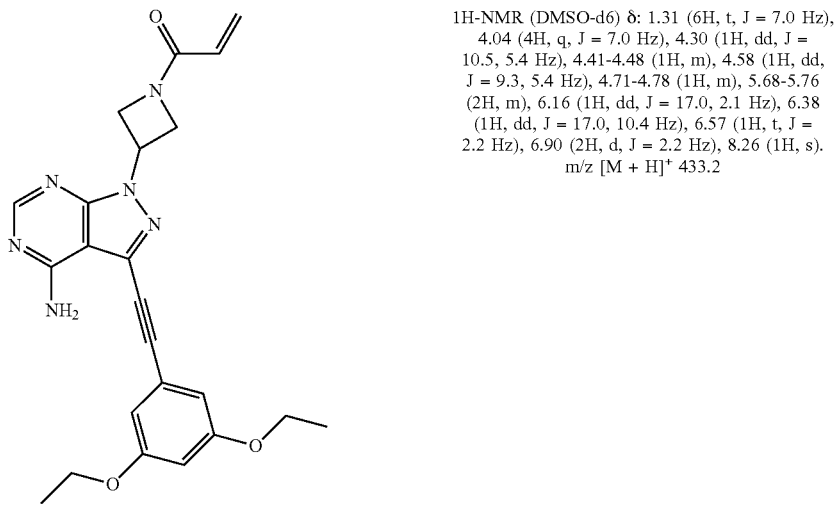 | 1H-NMR (DMSO-d6) δ: 1.31 (6H, t, J = 7.0 Hz), 4.04 (4H, q, J = 7.0 Hz), 4.30 (1H, dd, J = 10.5, 5.4 Hz), 4.41-4.48 (1H, m), 4.58 (1H, dd, J = 9.3, 5.4 Hz), 4.71-4.78 (1H, m), 5.68-5.76 (2H, m), 6.16 (1H, dd, J = 17.0, 2.1 Hz), 6.38 (1H, dd, J = 17.0, 10.4 Hz), 6.57 (1H, t, J = 2.2 Hz), 6.90 (2H, d, J = 2.2 Hz), 8.26 (1H, s).<br>m/z [M + H]⁺ 433.2 |
|---|---|---|
| 25 | 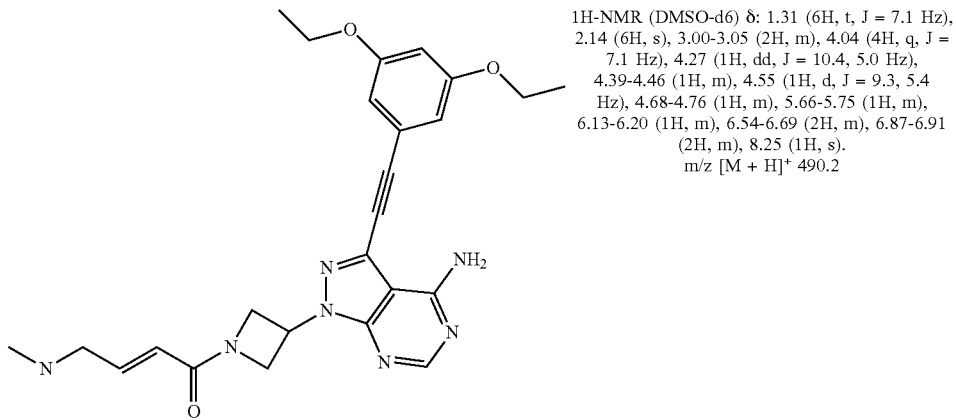 | 1H-NMR (DMSO-d6) δ: 1.31 (6H, t, J = 7.1 Hz), 2.14 (6H, s), 3.00-3.05 (2H, m), 4.04 (4H, q, J = 7.1 Hz), 4.27 (1H, dd, J = 10.4, 5.0 Hz), 4.39-4.46 (1H, m), 4.55 (1H, d, J = 9.3, 5.4 Hz), 4.68-4.76 (1H, m), 5.66-5.75 (1H, m), 6.13-6.20 (1H, m), 6.54-6.69 (2H, m), 6.87-6.91 (2H, m), 8.25 (1H, s).<br>m/z [M + H]⁺ 490.2 |

TABLE 7-continued
| | | |
|---|---|---|
| 26 | 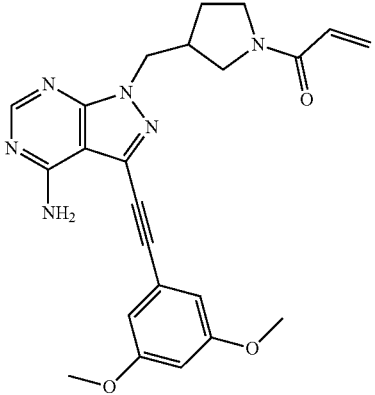 [SMILES: C=CC(=O)N1CCC(Cn2nc(C#Cc3cc(OC)cc(OC)c3)c3c(N)ncnc32)C1] | 1H-NMR (DMSO-d6) δ: 1.57-1.92 (2H, m), 2.64-2.85 (1H, m), 3.10-3.65 (4H, m), 3.72 (6H, s), 4.28 4.35 (2H, m), 5.53-5.59 (1H, m), 5.95-6.06 (1H, m), 6.38-6.55 (2H, m), 6.83-6.86 (2H, m), 8.16-8.19 (1H, m). m/z [M + H]⁺ 433.1 |
| 27 | 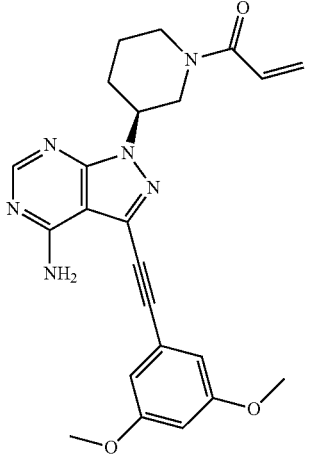 [SMILES: C=CC(=O)N1CCC[C@H](n2nc(C#Cc3cc(OC)cc(OC)c3)c3c(N)ncnc32)C1] | 1H-NMR (DMSO-d6) δ: 1.55-2.32 (4H, m), 2.87-4.71 (5H, m), 3.78 (6H, m), 5.50 5.75 (1H, m), 6.05-6.20 (1H, m), 6.61 (1H, t, J = 2.2 Hz), 6.65-6.91 (1H, m), 6.91 (2H, d, J = 2.2 Hz), 8.27 (1H, s). m/z [M + H]⁺ 433.1 |
TABLE 8
| | | |
|---|---|---|
| 28 | 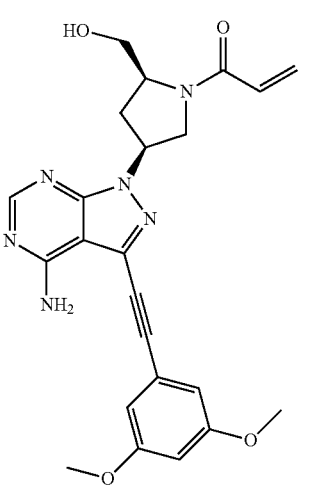 [SMILES: C=CC(=O)N1C[C@@H](n2nc(C#Cc3cc(OC)cc(OC)c3)c3c(N)ncnc32)C[C@H]1CO] | 1H-NMR (DMSO-d6) δ: 2.48-2.50 (2H, m), 3.27 4.35 (11H, m), 4.89 (0.5H, t, J = 5.7 Hz), 5.02 (0.5H, t, J = 5.7 Hz), 5.28 5.37 (1H, m), 5.66-5.71 (1H, m), 6.13-6.20 (1H, m), 6.60 (1H, t, J = 2.3 Hz), 6.93 (2H, d, J = 2.3 Hz), 8.26 (1H, s). m/z [M + H]⁺ 449.1 |

TABLE 8-continued
| 29 | 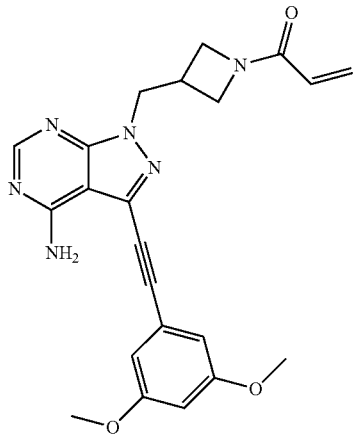 [SMILES: C=CC(=O)N1CC(Cn2nc(C#Cc3cc(OC)cc(OC)c3)c3c(N)ncnc32)C1] | 1H-NMR (CDCl3) δ: 3.20-3.35 (1H, m), 3.81 (6H, s), 3.91-4.02 (1H, m), 4.14-4.38 (3H, m), 4.58 4.70 (2H, m), 5.66 (1H, d, J = 10.5 Hz), 5.85-6.05 (2H, m), 6.16 (1H, dd, J = 17.0, 10.4 Hz), 6.33 (1H, d, J = 17.1 Hz), 6.54 (1H, s), 6.74 (2H, dd, J = 3.3, 2.6 Hz), 8.35 (1H, s). m/z [M + H]$^+$ 419.1 |
| --- | --- | --- |
| 30 | 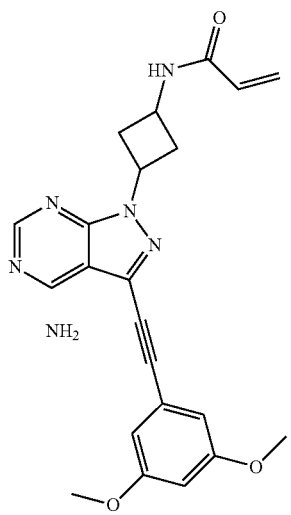 | m/z [M + H]$^+$ 419.2 |
| 31 | 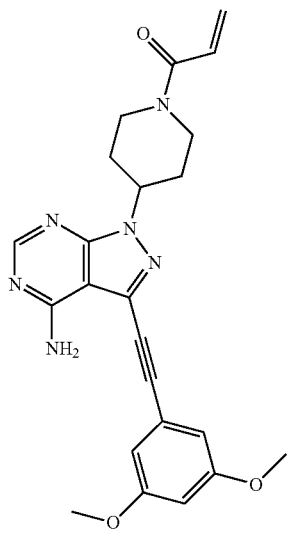 [SMILES: C=CC(=O)N1CCC(n2nc(C#Cc3cc(OC)cc(OC)c3)c3c(N)ncnc32)CC1] | 1H-NMR (CDCl3) δ: 2.08-2.10 (2H, m), 2.20-2.30 (4H, m), 2.81-2.98 (1H, m), 3.22-3.40 (1H, m), 3.82 (6H, s), 4.15-4.25 (1H, m), 4.80-4.88 (1H, m) 4.96-5.04 (1H, m), 5.72 (1H, dd, J = 10.8, 2.0 Hz), 6.30 (1H, dd, J = 16.8, 2.0 Hz), 6.54 (1H, t, J = 2.0 Hz) 6.61 (1H, dd, J = 17.2, 10.8 Hz), 6.73 (2H, d, J = 2.4 Hz), 8.42 (1H, s) m/z [M + H]$^+$ 433.2 |

TABLE 9
| | | |
|---|---|---|
| 32 | 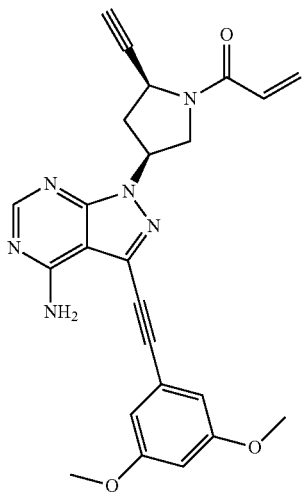 [SMILES: C#C[C@@H]1C[C@H](n2nc(C#Cc3cc(OC)cc(OC)c3)c3c(N)ncnc32)CN1C(=O)C=C] | 1H-NMR (CDCl3) δ: 2.34-2.42 (1H, m), 2.80-3.10 (2H, m), 3.82 (6H, s), 4.05-4.20 (2H, m), 4.20-4.50 (1H, m), 4.70-4.95 (1H, m), 5.30-5.40 (1H, m), 5.75-5.80 (1H, m), 5.98 (2H, brs), 6.40-6.50 (1H, m), 6.54 (1H, s), 6.70-6.73 (2H, m), 8.38 (1H, m).<br>m/z [M + H]⁺ 443.1 |
| 33 | 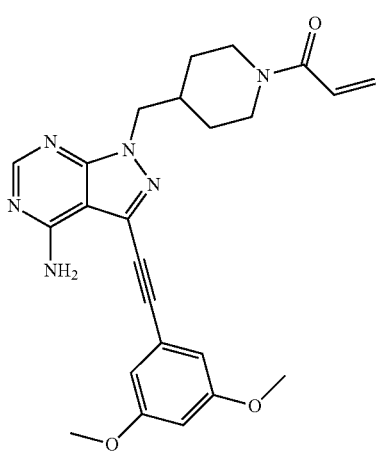 [SMILES: C=CC(=O)N1CCC(Cn2nc(C#Cc3cc(OC)cc(OC)c3)c3c(N)ncnc32)CC1] | m/z [M + H]⁺ 447.2 |
| 34 | 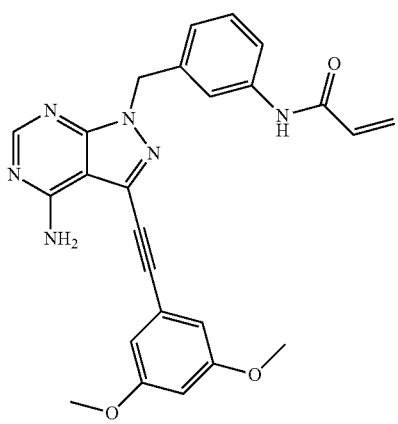 | 1H-NMR (DMSO-d6) δ: 3.77 (6H, s), 5.50 (2H, s), 5.72 (1H, dd, J = 10.2, 2.1 Hz), 6.22 (1H, dd, J = 17.1, 2.1 Hz), 6.38 (1H, dd, J = 17.1, 10.2 Hz), 6.59 (1H, t, J = 2.3 Hz), 6.90 (2H, d, J = 2.3 Hz), 7.00 (1H, d, J = 7.8 Hz), 7.29 (1H, t, J = 7.8 Hz), 7.45 (1H, s), 7.63-7.66 (1H, m), 8.28 (1H, s), 10.12 (1H, s).<br>m/z [M + H]⁺ 465.2 |

TABLE 9-continued

| | | |
|---|---|---|
| 35 | (structure) | m/z [M + H]⁺ 476.2 |
| 36 | (structure) | 1H-NMR (CDCl3) δ: 2.09 (2H, d, J = 10.7 Hz), 2.29 (8H, m), 2.80-2.98 (1H, m), 3.12 (2H, d, J = 4.9 Hz), 3.19-3.40 (1H, m), 3.81 (6H, s), 4.12-4.32 (1H, m), 4.74-4.90 (1H, m), 4.94-4.96 (1H, m), 5.74-5.85 (2H, m), 6.43-6.55 (2H, m), 6.73 (2H, s), 6.80-6.80 (1H, m), 8.37 (1H, s). m/z [M + H]⁺ 490.2 |

TABLE 10

| | | |
|---|---|---|
| 37 | (structure) | m/z [M + H]⁺ 504.2 |
| 38 | (structure) | 1H-NMR (DMSO-d6) δ: 2.13 (3H, s), 2.17 (3H, S), 2.29-2.49 (2H, m), 3.01 (1H, d, J = 6.3 Hz), 3.06 (1H, d, J = 6.3 Hz), 3.40-4.10 (4H, m), 3.76 (6H, m), 5.23-6.37 (1H, m), 6.36 (0.5H, d, J = 15.0 Hz), 6.43 (0.5H, d, J = 15.0 Hz), 6.54 (1H, t, J = 2.2 Hz), 6.60-6.69 (1H, m), 6.74 (2H, d, J = 2.2 Hz), 7.71 (0.5H, s), 7.76 (0.5H, s), 8.16 (1H, t, J = 2.2 Hz). m/z [M + H]⁺ 475.1 |

TABLE 10-continued
| | | |
|---|---|---|
| 39 | 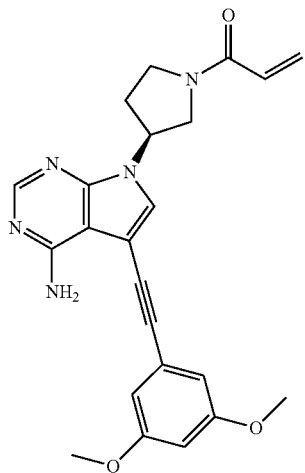 [SMILES: C=CC(=O)N1CC[C@H](n2cc(C#Cc3cc(OC)cc(OC)c3)c3c(N)ncnc32)C1] | 1H-NMR (DMSO-d6) δ: 2.30-2.50 (2H, m), 3.40-4.15 (4H, m), 3.77 (6H, m), 5.20-5.40 (1H, m), 5.60-5.80 (1H, m), 6.10-6.20 (1H, m), 6.54 (1H, s), 6.54-6.74 (1H, m), 6.74 (2H, s), 7.72 (0.5H, s), 7.76 (0.5H, s), 8.18 (1H, s). m/z [M + H]$^+$ 418.0 |
| 40 | 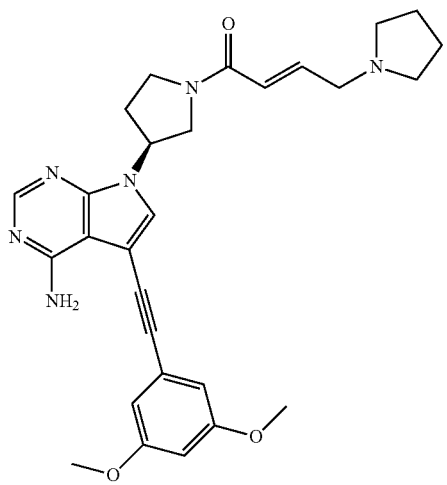 [SMILES: COc1cc(C#Cc2cn([C@H]3CCN(C(=O)/C=C/CN4CCCC4)C3)c3ncnc(N)c23)cc(OC)c1] | 1H-NMR (DMSO-d6) δ: 1.62-1.72 (4H, m), 2.28-2.51 (6H, m), 3.17 (1H, d, J = 5.9 Hz), 3.21 (1H, d, J = 5.9 Hz), 3.52-3.90 (9.5H, m), 4.02-4.12 (0.5H, m), 5.20-5.35 (1H, m), 6.30-6.45 (1H, m), 6.53 (1H, t, J = 2.4 Hz), 6.60-6.80 (3H, m), 7.71 (0.5H, s), 7.75 (0.5H, s), 8.17 (0.5H, s), 8.18 (0.5H, m). m/z [M + H]$^+$ 501.1 |
TABLE 11
| | | |
|---|---|---|
| 41 | 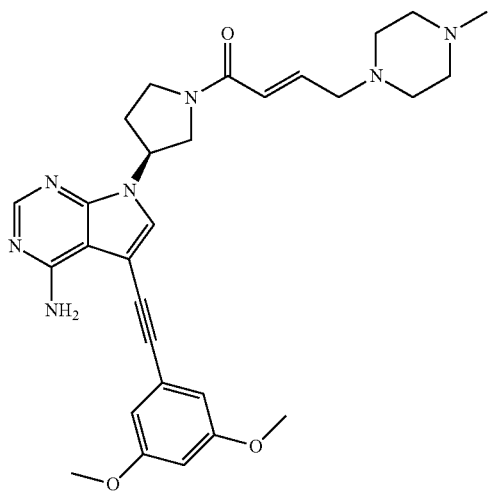 [SMILES: COc1cc(C#Cc2cn([C@H]3CCN(C(=O)/C=C/CN4CCN(C)CC4)C3)c3ncnc(N)c23)cc(OC)c1] | 1H-NMR (DMSO-d6) δ: 2.15 (1.5H, s), 2.17 (1.5H, s), 2.18-2.42 (10H, m), 3.05 (1H, d, J = 6.2 Hz), 3.10 (1H, d, J = 6.2 Hz), 3.47-3.94 (9.5H, m), 4.02-4.10 (0.5H, m), 5.22-5.38 (1H, m), 6.32-6.45 (1H, m), 6.54 (1H, d, J = 1.8 Hz), 6.57-6.70 (1H, m), 6.74 (2H, d, J = 1.5 Hz), 7.70 (0.5H, s), 7.75 (0.5H, s), 8.14-8.17 (1H, m). m/z [M + H]$^+$ 530.2 |

TABLE 11-continued
| | | |
|---|---|---|
| 42 | 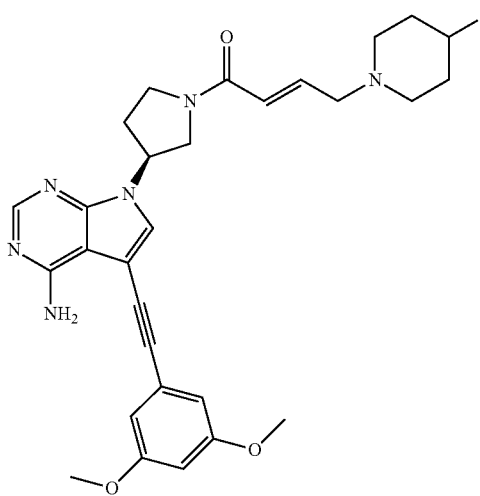 | 1H-NMR (DMSO-d6) δ: 1.32-1.42 (2H, m), 1.60-1.75 (2H, m), 1.95-2.06 (2H, m), 2.29-2.52 (2H, m), 2.60-2.70 (2H, m), 3.04 (1H, d, J = 6.2 Hz), 3.08 (1H, d, J = 6.2 Hz), 3.35-3.94 (10.5H, m), 4.05-4.10 (0.5H, m), 5.23-5.37 (1H, m), 6.34 (0.5H, d, J = 15.4 Hz), 6.41 (0.5H, d, J = 15.4 Hz), 6.53 (1H, t, J = 2.4 Hz), 6.59-6.68 (1H, m), 6.74 (2H, d, J = 1.5 Hz), 7.71 (0.5H, s), 7.75 (0.5H, s), 8.15-8.17 (1H, m). <br> m/z [M + H]+ 531.1 |
| 43 | 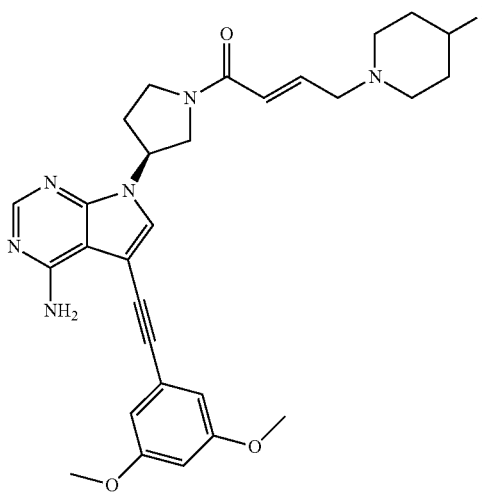 | 1H-NMR (DMSO-d6) δ: 1.60-1.90 (4H, m), 2.20-2.50 (6H, m), 3.07 (1H, d, J = 6.1 Hz), 3.12 (1H, d, J = 6.1 Hz), 3.52-3.89 (9.5H, m), 4.03-4.10 (0.5H, m), 4.55 4.80 (1H, m), 5.20-5.40 (1H, m), 6.35-6.46 (1H, m), 6.53 (1H, t, J = 2.2 Hz), 6.55-6.70 (1H, m), 6.74 (2H, d, J = 2.2 Hz), 7.71 (0.5H, s), 7.76 (0.5H, s), 8.17 (0.5H, s), 8.18 (0.5H, m). <br> m/z [M + H]+ 533.1 |
TABLE 12
| | | |
|---|---|---|
| 44 | 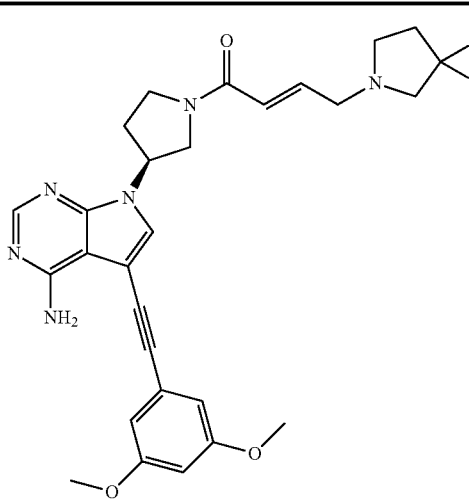 | 1H-NMR (DMSO-d6) δ: 2.18-2.54 (2H, m), 2.66-2.93 (4H, m), 3.18-3.24 (2H, m), 3.65-3.93 (9.5H, m), 4.04-4.10 (0.5H, m), 5.24-5.38 (1H, m), 6.35-6.50 (1H, m), 6.53 (3H, t, J = 2.2 Hz), 6.59-6.69 (1H, m), 6.74 (2H, d, J = 2.2 Hz), 7.71 (0.5H, s), 7.76 (0.5H, s), 8.17 (0.5H, s), 8.18 (0.5H, m). <br> m/z [M + H]+ 537.1 |

TABLE 12-continued
| 45 | 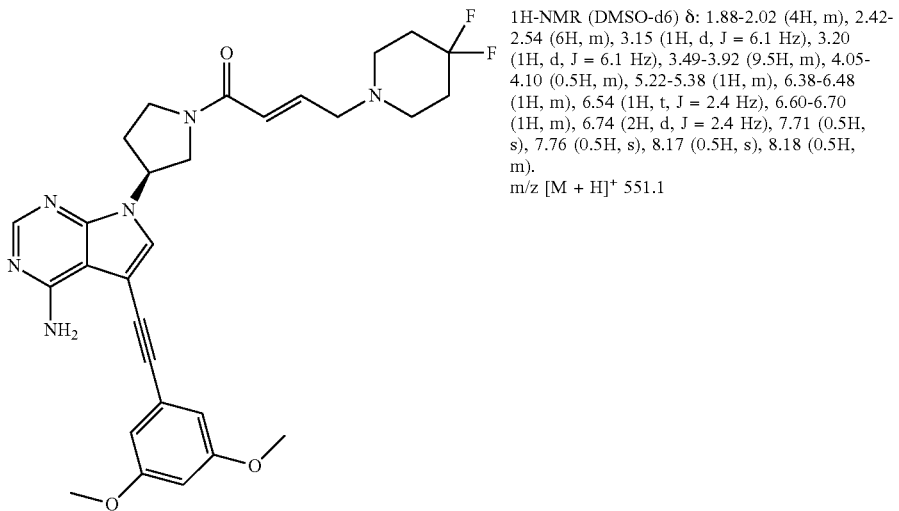 | 1H-NMR (DMSO-d6) δ: 1.88-2.02 (4H, m), 2.42-2.54 (6H, m), 3.15 (1H, d, J = 6.1 Hz), 3.20 (1H, d, J = 6.1 Hz), 3.49-3.92 (9.5H, m), 4.05-4.10 (0.5H, m), 5.22-5.38 (1H, m), 6.38-6.48 (1H, m), 6.54 (1H, t, J = 2.4 Hz), 6.60-6.70 (1H, m), 6.74 (2H, d, J = 2.4 Hz), 7.71 (0.5H, s), 7.76 (0.5H, s), 8.17 (0.5H, s), 8.18 (0.5H, m).<br>m/z [M + H]$^+$ 551.1 |
|---|---|---|
| 46 | 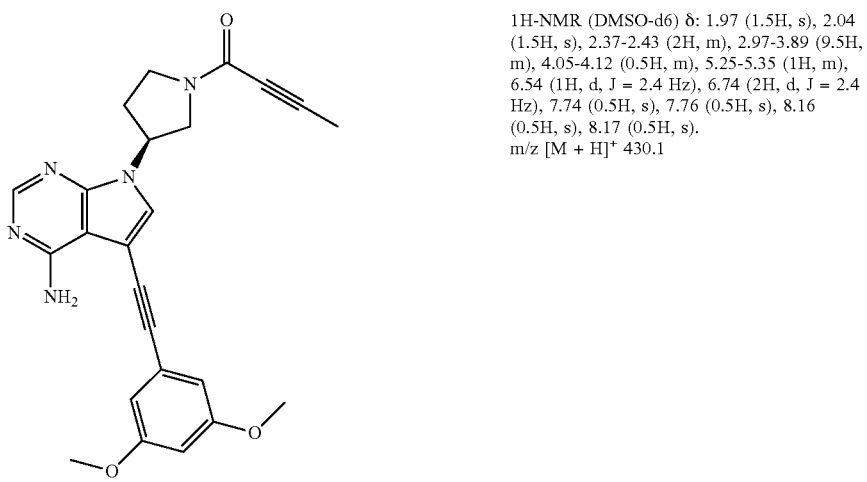 | 1H-NMR (DMSO-d6) δ: 1.97 (1.5H, s), 2.04 (1.5H, s), 2.37-2.43 (2H, m), 2.97-3.89 (9.5H, m), 4.05-4.12 (0.5H, m), 5.25-5.35 (1H, m), 6.54 (1H, d, J = 2.4 Hz), 6.74 (2H, d, J = 2.4 Hz), 7.74 (0.5H, s), 7.76 (0.5H, s), 8.16 (0.5H, s), 8.17 (0.5H, s).<br>m/z [M + H]$^+$ 430.1 |
| 47 | 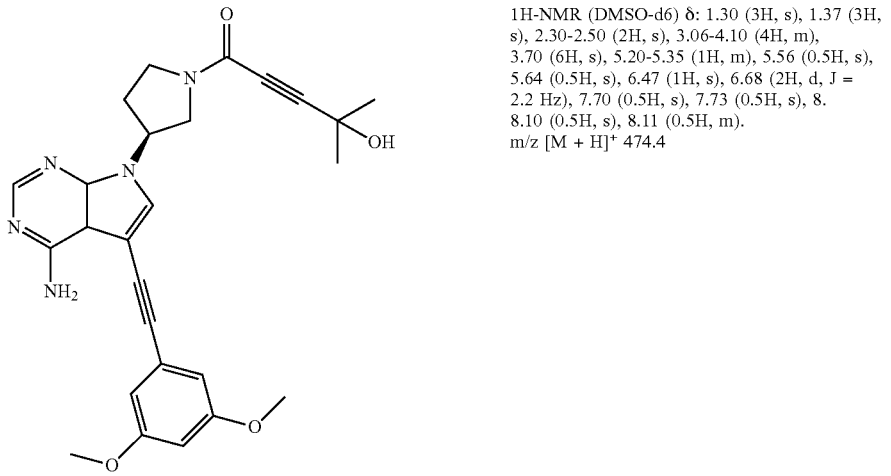 | 1H-NMR (DMSO-d6) δ: 1.30 (3H, s), 1.37 (3H, s), 2.30-2.50 (2H, s), 3.06-4.10 (4H, m), 3.70 (6H, s), 5.20-5.35 (1H, m), 5.56 (0.5H, s), 5.64 (0.5H, s), 6.47 (1H, s), 6.68 (2H, d, J = 2.2 Hz), 7.70 (0.5H, s), 7.73 (0.5H, s), 8. 8.10 (0.5H, s), 8.11 (0.5H, m).<br>m/z [M + H]$^+$ 474.4 |

TABLE 13
48 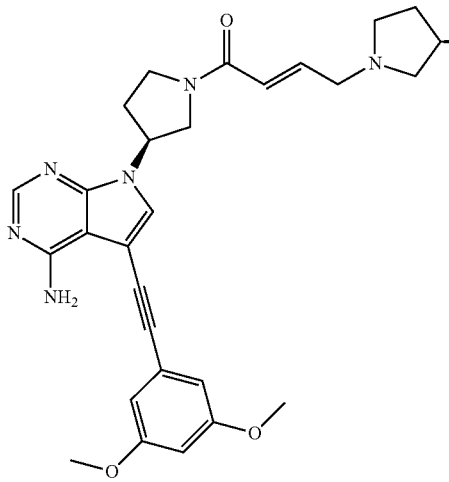
1H NMR (DMSO-d6) δ: 1.76-2.85 (8H, m), 3.16-4.08 (12H, m), 5.05-5.38 (2H, m), 6.35-6.48 (1H, m), 6.53 (1H, t, J = 2.3 Hz), 6.62-6.72 (1H, m), 6.74 (2H, d, J = 2.3 Hz), 7.71 (0.5H, s), 7.76 (0.5H, s), 8.17 (0.5H, s), 8.18 (0.5H, m).
m/z [M + H]+ 519.1
49 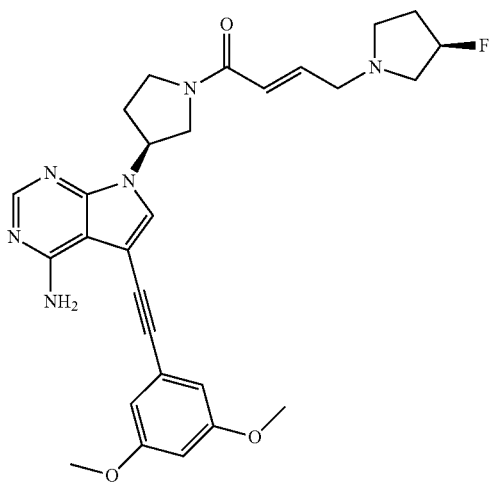 [SMILES: COc1cc(C#Cc2cn([C@H]3CCN(C(=O)/C=C/CN4CC[C@@H](F)C4)C3)c3ncnc(N)c23)cc(OC)c1]
1H-NMR (DMSO-d6) δ: 1.76-2.85 (8H, m), 3.16-4.08 (12H, m), 5.05-5.38 (2H, m), 6.35-6.48 (1H, m), 6.53 (1H, t, J = 2.3 Hz), 6.62-6.72 (1H, m), 6.74 (2H, d, J = 2.3 Hz), 7.71 (0.5H, s), 7.76 (0.5H, s), 8.17 (0.5H, s), 8.18 (0.5H, m).
m/z [M + H]+ 519.1
50 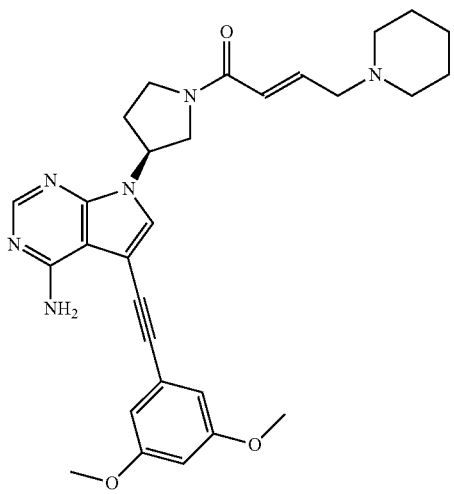 [SMILES: COc1cc(C#Cc2cn([C@H]3CCN(C(=O)/C=C/CN4CCCCC4)C3)c3ncnc(N)c23)cc(OC)c1]
1H-NMR (DMSO-d6) δ: 1.20 1.50 (6H, m), 2.19-2.43 (6H, m), 2.96 (1H, d, J = 6.2 Hz), 3.00 (1H, d, J = 5.5 Hz), 3.31-4.02 (4H, m), 3.73 (6H, s), 5.15-5.30 (1H, m), 6.31 (1H, dd, J = 28.7, 15.0 Hz), 6.47 (1H, d, J = 2.1 Hz), 6.50-6.65 (1H, m), 6.66 (2H, d, J = 2.1 Hz), 7.63 (0.5H, s), 7.68 (0.5H, s), 8.10 (1H, s).
m/z [M + H]+ 515.1

TABLE 13-continued
| 51 | 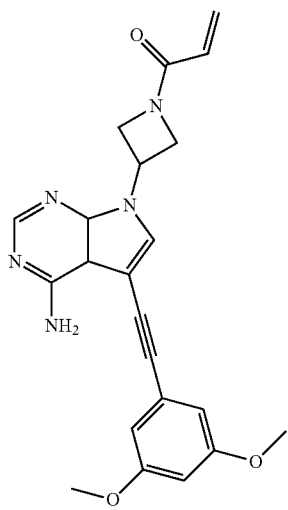 [SMILES: C=CC(=O)N1CC(N2C=C(C#Cc3cc(OC)cc(OC)c3)C3C(N)=NC=NC32)C1] | 1H-NMR (DMSO-d6) δ: 3.76 (6H, s,), 4.20-4.27 (1H, m), 4.30-4.39 (1H, m), 4.50-4.60 (1H, m), 4.62-4.68 (1H, m), 5.50-5.60 (1H, m), 5.64 (1H, dd, J = 10.3, 2.3 Hz), 6.08 (1H, dd, J = 16.9, 2.3 Hz), 6.29 (1H, dd, J = 16.9, 10.3 Hz), 6.47 (1H, t, J = 2.1 Hz), 6.67 (2H, d, J = 2.1 Hz), 7.98 (1H, s), 8.09 (1, s). m/z [M + H]$^+$ 404.0 |
TABLE 14
| 52 | 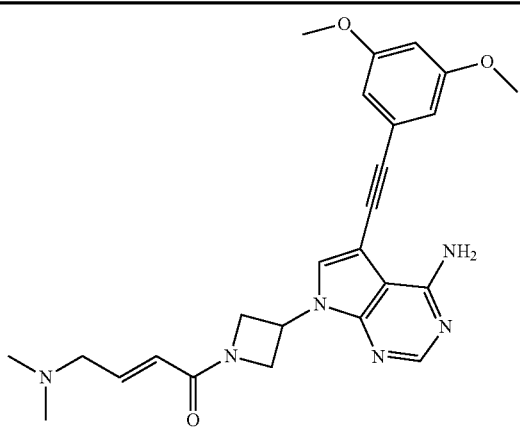 | 1H-NMR (DMSO-d6) δ: 2.72 (6H, s), 3.76 (6H, s), 3.84 (2H, d, J = 6.8 Hz), 4.30-4.35 (1H, m), 4.44 (1H, t, J = 9.5 Hz), 4.60-4.75 (2H, m), 5.50-5.60 (1H, m), 6.42 (1H, d, J = 15.4 Hz), 6.54 (1H, t, J = 2.4 Hz), 6.59-6.67 (1H, m), 6.73 (2H, d, J = 2.4 Hz), 8.03 (1H, s), 8.15 (1H, s). m/z [M + H]$^+$ 461.1 |
| 53 | 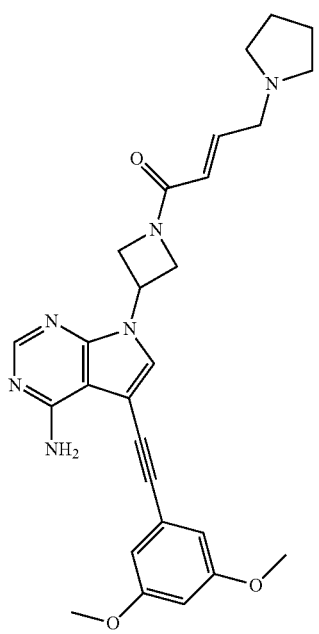 [SMILES: COc1cc(C#Cc2cn(C3CN(C(=O)/C=C/CN4CCCC4)C3)c3ncnc(N)c23)cc(OC)c1] | 1H-NMR (DMSO-d6) δ: 1.69 (4H, brs), 2.35-2.55 (4H, m), 3.22 (2H, brs), 3.76 (6H, s), 4.25-4.45 (2H, m), 4.55-4.75 (2H, m), 5.49-5.59 (1H, t, m), 6.15 (1H, d, J = 15.5 Hz), 6.54 (1H, t, J = 2.3 Hz), 6.66 (1H, dt, J = 15.5, 6.0 Hz), 6.74 (2H, d, J = 2.3 Hz), 8.05 (1H, s), 8.15 (1H, s). m/z [M + H]$^+$ 487.1 |

TABLE 14-continued
| 54 | 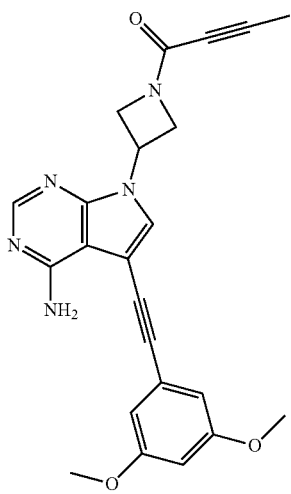 [SMILES: CC#CC(=O)N1CC(n2cc(C#Cc3cc(OC)cc(OC)c3)c3c(N)ncnc32)C1] | 1H-NMR (DMSO-d6) δ: 2.01 (3H, s), 3.77 (6H, s), 4.25-4.41 (1H, m), 4.38 (1H, t, J = 9.3 Hz), 4.52-4.63 (2H, m), 5.52-5.57 (1H, m), 6.54 (1H, t, J = 2.2 Hz), 6.74 (2H, d, J = 2.2 Hz), 8.03 (1H, s), 8.16 (1H, s).<br>m/z [M + H]⁺ 416.4 |
|---|---|---|
| 55 | 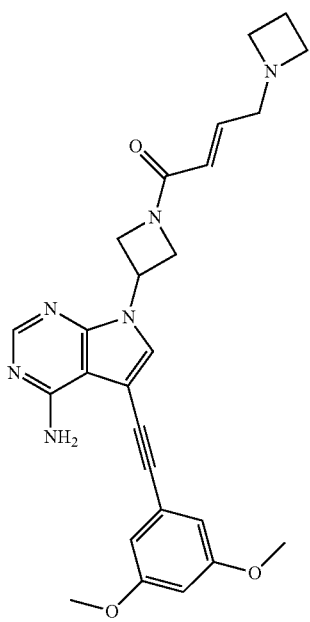 [SMILES: COc1cc(C#Cc2cn(C3CN(C(=O)/C=C/CN4CCC4)C3)c3ncnc(N)c23)cc(OC)c1] | 1H-NMR (DMSO-d6) δ: 1.94-2.00 (2H, m), 3.11-3.15 (6H, t, J = 7.0 Hz), 3.77 (6H, s), 4.25-4.28 (1H, m), 4.39 (1H, t, J = 9.3 Hz), 4.58-4.75 (2H, m), 5.50-5.58 (1H, m), 6.07 (1H, d, J = 15.4 Hz), 6.50-6.58 (2H, m), 6.74 (2H, d, J = 2.6 Hz), 8.05 (1H, s), 8.15 (1H, s).<br>m/z [M + H]⁺ 473.1 |
TABLE 15
| 56 | 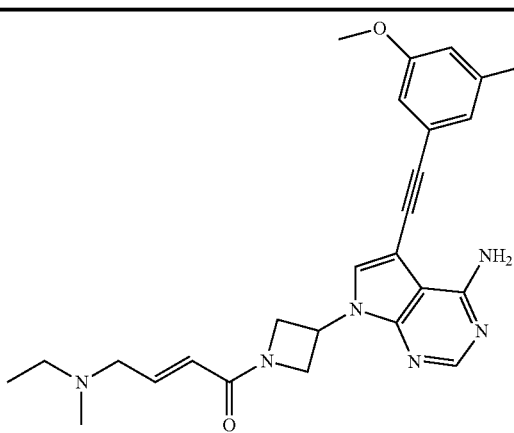 | 1H-NMR (DMSO-d6) δ: 0.98 (3H, t, J = 7.1 Hz),<br>2.13 (3H, s), 2.35 (2H, q, J = 7.2 Hz), 3.10 (2H, d, J = 6.2 Hz), 3.77 (6H, s), 4.24-4.29 (1H, m), 4.40 (1H, t, J = 9.5 Hz), 4.65-4.75 (2H, m), 5.53-5.57 (1H, m), 6.15 (1H, d, J = 15.4 Hz), 6.54 (1H, t, J = 2.5 Hz), 6.64 (1H, dt, J = 15.4, 6.1 Hz), 6.74 (2H, d, J = 2.5 Hz), 8.05 (1H, s), 8.15 (1H, s).<br>m/z [M + H]⁺ 475.1 |
|---|---|---|

TABLE 15-continued
| 57 | 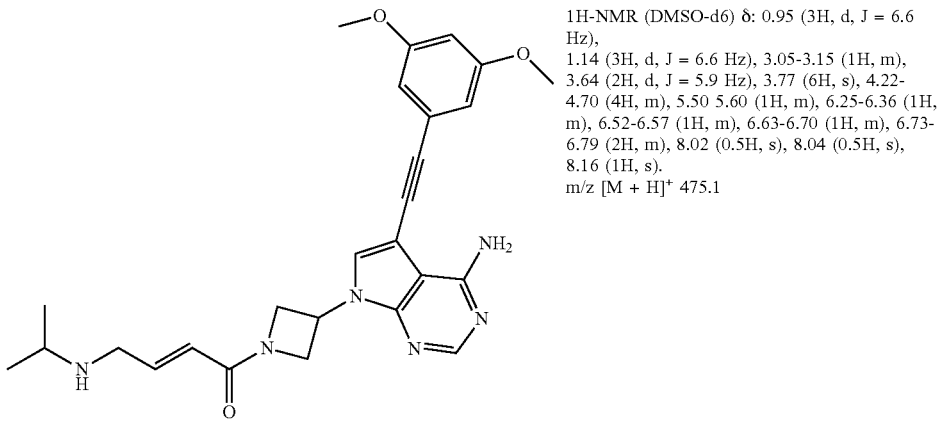 | 1H-NMR (DMSO-d6) δ: 0.95 (3H, d, J = 6.6 Hz), 1.14 (3H, d, J = 6.6 Hz), 3.05-3.15 (1H, m), 3.64 (2H, d, J = 5.9 Hz), 3.77 (6H, s), 4.22-4.70 (4H, m), 5.50 5.60 (1H, m), 6.25-6.36 (1H, m), 6.52-6.57 (1H, m), 6.63-6.70 (1H, m), 6.73-6.79 (2H, m), 8.02 (0.5H, s), 8.04 (0.5H, s), 8.16 (1H, s). m/z [M + H]+ 475.1 |
| 58 | 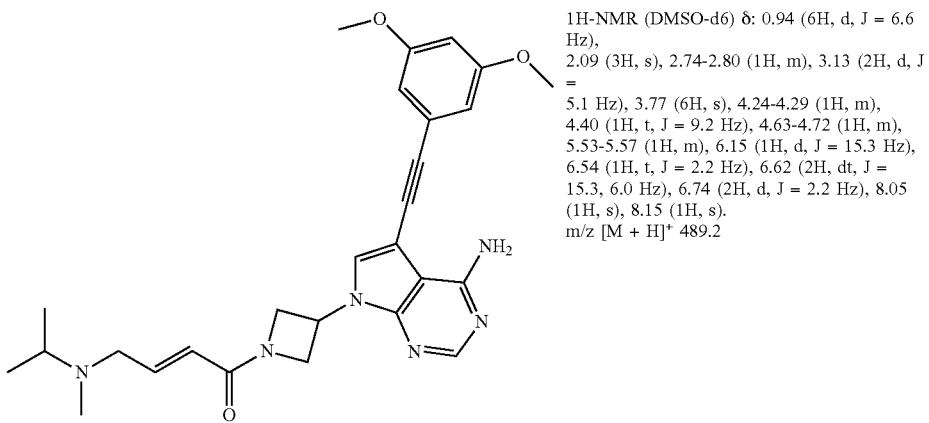 | 1H-NMR (DMSO-d6) δ: 0.94 (6H, d, J = 6.6 Hz), 2.09 (3H, s), 2.74-2.80 (1H, m), 3.13 (2H, d, J = 5.1 Hz), 3.77 (6H, s), 4.24-4.29 (1H, m), 4.40 (1H, t, J = 9.2 Hz), 4.63-4.72 (1H, m), 5.53-5.57 (1H, m), 6.15 (1H, d, J = 15.3 Hz), 6.54 (1H, t, J = 2.2 Hz), 6.62 (2H, dt, J = 15.3, 6.0 Hz), 6.74 (2H, d, J = 2.2 Hz), 8.05 (1H, s), 8.15 (1H, s). m/z [M + H]+ 489.2 |
TABLE 16
| 59 | 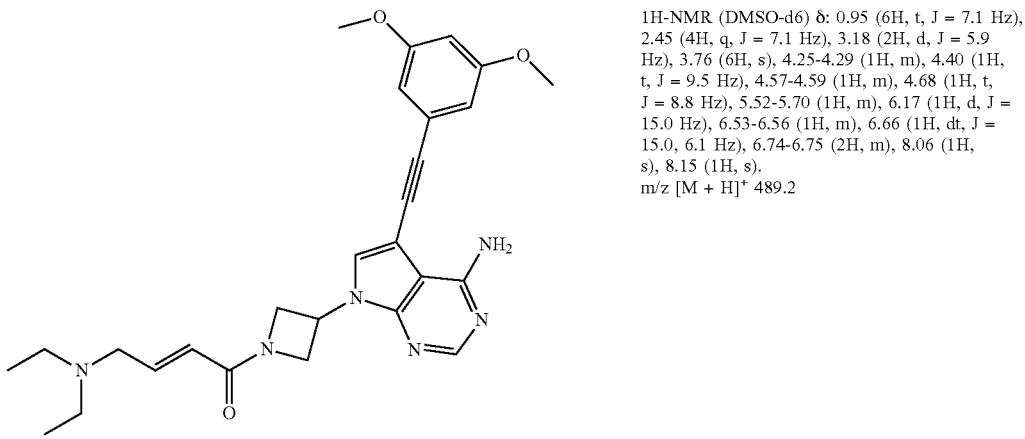 | 1H-NMR (DMSO-d6) δ: 0.95 (6H, t, J = 7.1 Hz), 2.45 (4H, q, J = 7.1 Hz), 3.18 (2H, d, J = 5.9 Hz), 3.76 (6H, s), 4.25-4.29 (1H, m), 4.40 (1H, t, J = 9.5 Hz), 4.57-4.59 (1H, m), 4.68 (1H, t, J = 8.8 Hz), 5.52-5.70 (1H, m), 6.17 (1H, d, J = 15.0 Hz), 6.53-6.56 (1H, m), 6.66 (1H, dt, J = 15.0, 6.1 Hz), 6.74-6.75 (2H, m), 8.06 (1H, s), 8.15 (1H, s). m/z [M + H]+ 489.2 |

TABLE 16-continued
| 60 | 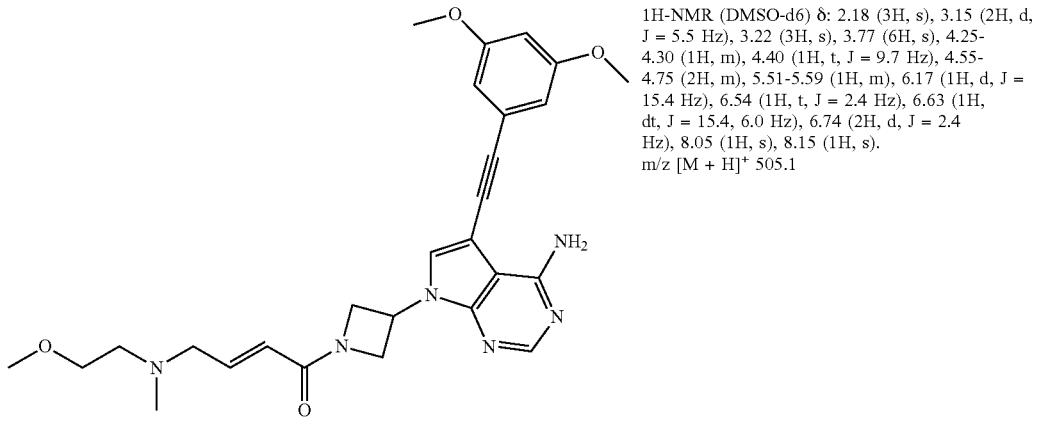 | 1H-NMR (DMSO-d6) δ: 2.18 (3H, s), 3.15 (2H, d, J = 5.5 Hz), 3.22 (3H, s), 3.77 (6H, s), 4.25-4.30 (1H, m), 4.40 (1H, t, J = 9.7 Hz), 4.55-4.75 (2H, m), 5.51-5.59 (1H, m), 6.17 (1H, d, J = 15.4 Hz), 6.54 (1H, t, J = 2.4 Hz), 6.63 (1H, dt, J = 15.4, 6.0 Hz), 6.74 (2H, d, J = 2.4 Hz), 8.05 (1H, s), 8.15 (1H, s).<br>m/z [M + H]+ 505.1 |
| --- | --- | --- |
| 61 | 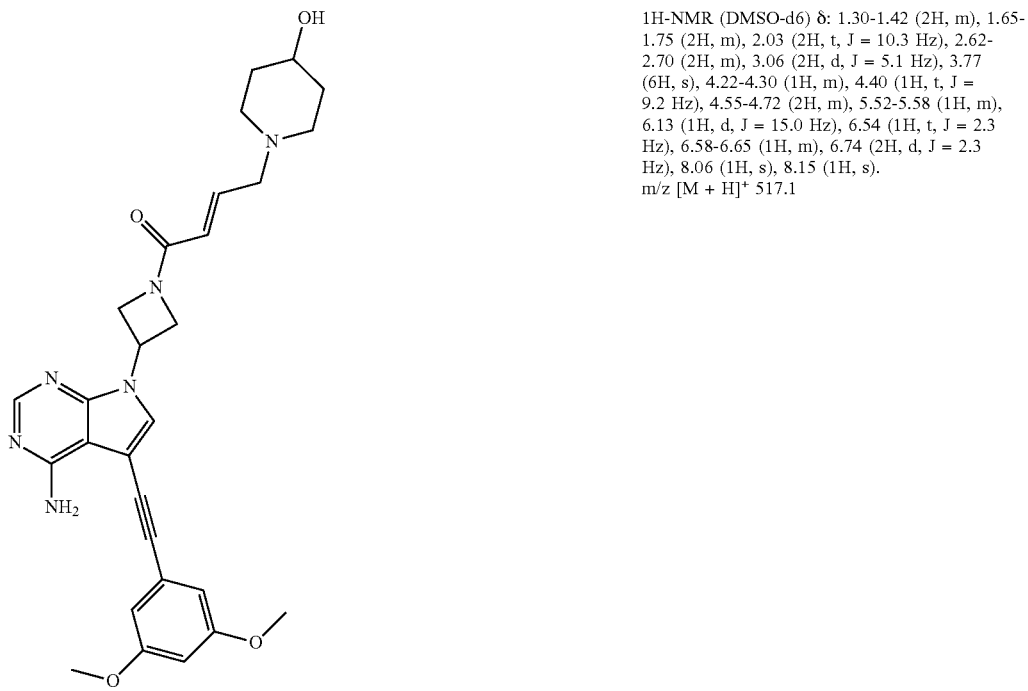 | 1H-NMR (DMSO-d6) δ: 1.30-1.42 (2H, m), 1.65-1.75 (2H, m), 2.03 (2H, t, J = 10.3 Hz), 2.62-2.70 (2H, m), 3.06 (2H, d, J = 5.1 Hz), 3.77 (6H, s), 4.22-4.30 (1H, m), 4.40 (1H, t, J = 9.2 Hz), 4.55-4.72 (2H, m), 5.52-5.58 (1H, m), 6.13 (1H, d, J = 15.0 Hz), 6.54 (1H, t, J = 2.3 Hz), 6.58-6.65 (1H, m), 6.74 (2H, d, J = 2.3 Hz), 8.06 (1H, s), 8.15 (1H, s).<br>m/z [M + H]+ 517.1 |

TABLE 17
| | | |
|---|---|---|
| 62 | 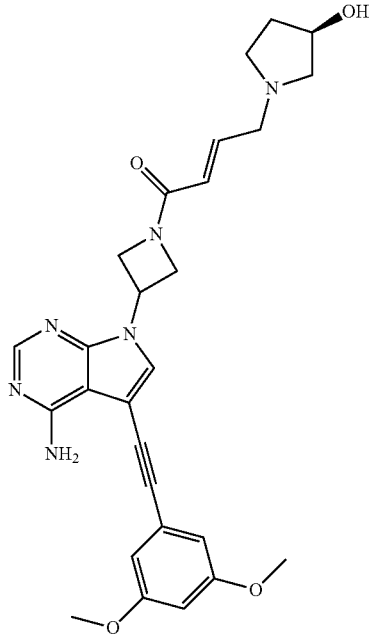 [SMILES: COc1cc(C#Cc2cn(C3CN(C(=O)/C=C/CN4CC[C@@H](O)C4)C3)c3ncnc(N)c23)cc(OC)c1] | 1H-NMR (DMSO-d6) δ: 1.48-1.58 (1H, m), 1.92-2.00 (1H, m), 2.31-2.71 (4H, m), 3.19 (2H, brs), 3.77 (6H, s), 4.15-4.30 (2H, m), 4.35-4.44 (1H, m), 4.55-4.72 (2H, m), 5.50-5.60 (1H, m), 6.15 (1H, d, J = 15.4 Hz), 6.54 (1H, t, J = 2.2 Hz), 6.60-6.70 (1H, m), 6.75 (2H, d, J = 2.2 Hz), 8.05 (1H, s), 8.15 (1H, d, J = 1.8 Hz). m/z [M + H]$^+$ 503.1 |
| 63 | 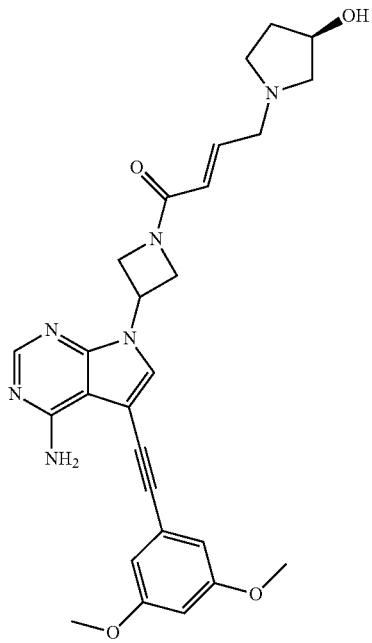 [SMILES: COc1cc(C#Cc2cn(C3CN(C(=O)/C=C/CN4CC[C@@H](O)C4)C3)c3ncnc(N)c23)cc(OC)c1] | 1H-NMR (DMSO-d6) δ: 1.48-1.58 (1H, m), 1.92-2.00 (1H, m), 2.31-2.71 (4H, m), 3.19 (2H, brs), 3.77 (6H, s), 4.15-4.30 (2H, m), 4.35-4.44 (1H, m), 4.55-4.72 (2H, m), 5.50-5.60 (1H, m), 6.15 (1H, d, J = 15.4 Hz), 6.54 (1H, t, J = 2.2 Hz), 6.60-6.70 (1H, m), 6.75 (2H, d, J = 2.2 Hz), 8.05 (1H, s), 8.15 (1H, d, J = 1.8 Hz). m/z [M + H]$^+$ 503.1 |

TABLE 17-continued

| 64 | (structure) | 1H-NMR (CDCl3) δ: 1.67-2.22 (4H, m), 2.71-2.95 (1H, m), 3.19-3.35 (1H, m), 3.81 (6H, s), 4.09-4.25 (1H, m), 4.83-4.95 (2H, m), 5.61-5.78 (3H, m), 6.28 6.68 (5H, m), 7.24 (1H, s), 8.31 (1H, s). m/z [M + H]+ 432.2 |
| --- | --- | --- |
| 65 | (structure) | 1H-NMR (CDCl3) δ: 1.65-2.00 (4H, m), 2.29 (6H, s), 2.77-2.92 (1H, m), 3.12 (2H, d, J = 5.9 Hz), 3.22-3.38 (1H, m), 3.81 (6H, s), 4.14-4.30 (1H, m), 4.85-4.97 (2H, m), 5.66 (2H, br s), 6.44-6.55 (2H, m), 6.65 (2H, d, J = 2.2 Hz), 6.84-6.95 (1H, m), 7.24 (1H, s), 8.31 (1H, s). m/z [M + H]+ 489.2 |

TABLE 18

| 66 | (structure) | 1H-NMR (CDCl3) δ: 2.37-2.48 (1H, m), 2.82-2.93 (1H, m), 3.41-3.52 (1H, m), 3.82 (9H, s), 3.86-3.95 (1H, m), 4.25-4.38 (1H, m), 4.69 (1H, t, J = 8.3 Hz), 5.43-5.56 (1H, m), 5.65-5.83 (2H, m), 6.36-6.50 (3H, m), 6.65 (2H, d, J = 2.0 Hz), 7.37 (1H, s), 8.30 (1H, s). m/z [M + H]+ 476.2 |
| --- | --- | --- |

TABLE 18-continued
| 67 | 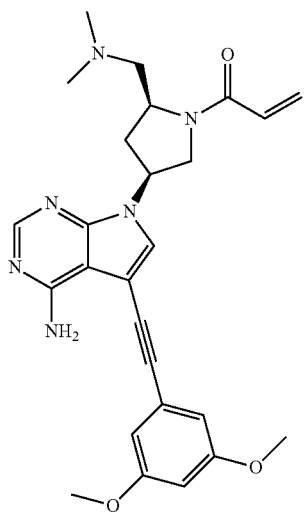 [SMILES: C=CC(=O)N1C[C@@H](n2cc(C#Cc3cc(OC)cc(OC)c3)c3c(N)ncnc32)C[C@H]1CN(C)C] | m/z [M + H]⁺ 475.2 |
| 68 | 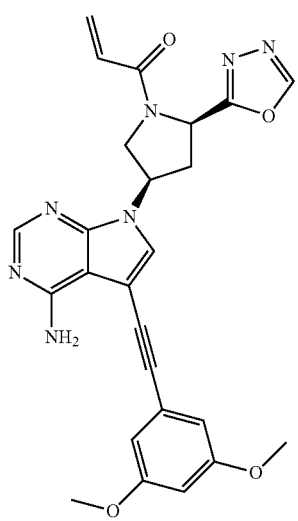 [SMILES: C=CC(=O)N1C[C@H](n2cc(C#Cc3cc(OC)cc(OC)c3)c3c(N)ncnc32)C[C@@H]1c1nnco1] | 1H-NMR (CDCl3) δ: 2.75-2.95 (1H, m), 2.99-3.15 (1H, m), 3.82 (6H, s), 4.00 (1H, t, J = 9.8 Hz), 4.32-4.50 (1H, m), 5.44-5.85 (5H, m), 6.44 (2H, d, J = 5.9 Hz), 6.49 (1H, t, J = 2.2 Hz), 6.66 (2H, d, J = 2.2 Hz), 7.44 (1H, br s), 8.30 (1H, s), 8.40 (1H, s).<br>m/z [M + H]⁺ 486.1 |
| 69 | 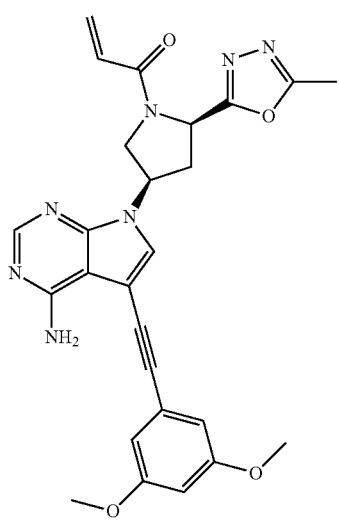 [SMILES: C=CC(=O)N1C[C@H](n2cc(C#Cc3cc(OC)cc(OC)c3)c3c(N)ncnc32)C[C@@H]1c1nnc(C)o1] | m/z [M + H]⁺ 500.2 |

TABLE 18-continued

| 70 | [structure] | 1H-NMR (CDCl3) δ: 2.36 (6H, br s), 2.69-2.90 (1H, m), 2.94-3.10 (1H, m), 3.69-3.80 (2H, m), 3.82 (6H, s), 3.92-4.05 (1H, m), 4.32-4.47 (1H, m), 5.39-5.83 (5H, m), 6.35-6.47 (2H, m), 6.49 (1H, t, J = 2.1 Hz), 6.65 (2H, d, J = 2.2 Hz), 7.44 (1H, br s), 8.30 (1H, s).<br>m/z [M + H]+ 543.2 |
|---|---|---|

TABLE 19

| 71 | [structure] | 1H-NMR (CDCl3) δ: 2.30 (6H, d, J = 7.6 Hz), 2.35-2.68 (3H, m), 2.77-2.92 (1H, m), 3.14 (3H, d, J = 79.5 Hz), 3.31-3.47 (1H, m), 3.69-3.81 (1H, m), 3.82 (6H, s), 3.95 (2H, q, J = 9.9 Hz), 4.35 (1H, t, J = 8.9 Hz), 5.08 (1H, t, J = 7.3 Hz), 5.50-5.79 (4H, m), 6.37-6.52 (3H, m), 6.65 (2H, t, J = 2.2 Hz), 7.59 (1H, d, J = 28.0 Hz), 8.30 (1H, s).<br>m/z [M + H]+ 546.3 |
|---|---|---|
| 72 | [structure] | m/z [M + H]+ 503.3 |

TABLE 19-continued
| | | |
|---|---|---|
| 73 | 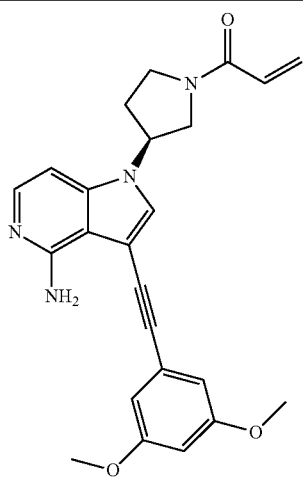 | 1H-NMR (DMSO-d6) δ: 2.21-2.44 (2H, m), 3.34-3.87 (9.5H, m), 4.00-4.10 (0.5H, m), 5.02-5.18 (1H, m), 5.58-5.68 (1H, m), 5.88 (2H, brs), 6.05-6.18 (1H, m), 6.45-6.65 (4H, m), 6.82-6.88 (1H, m), 7.60-7.63 (2H, m). m/z [M + H]$^+$ 417.5 |
TABLE 20
| Ref. Ex. Comp. | Structural formula | Physical properties |
|---|---|---|
| 1 | 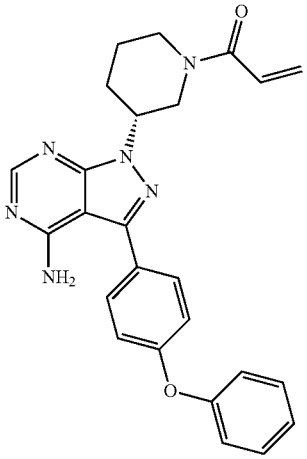 [SMILES: C=CC(=O)N1CCC[C@@H](n2nc(-c3ccc(Oc4ccccc4)cc3)c3c(N)ncnc32)C1] | m/z [M + H]$^+$ 441.2 |
| 2 | 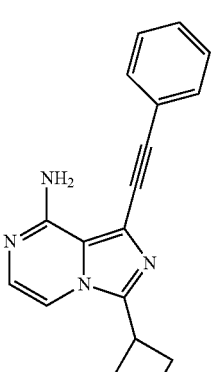 | m/z [M + H]$^+$ 289.1 |

TABLE 20-continued
| Ref. Ex. Comp. | Structural formula | Physical properties |
|---|---|---|
| 3 | 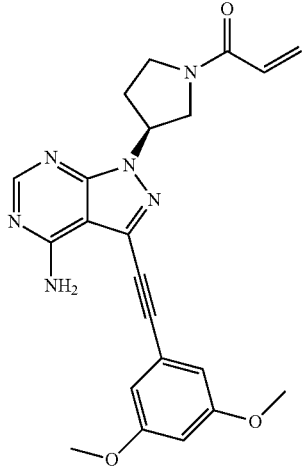 [SMILES: C=CC(=O)N1CC[C@H](n2nc(C#Cc3cc(OC)cc(OC)c3)c3c(N)ncnc32)C1] | m/z [M + H]+ 421.2 |
| 4 | 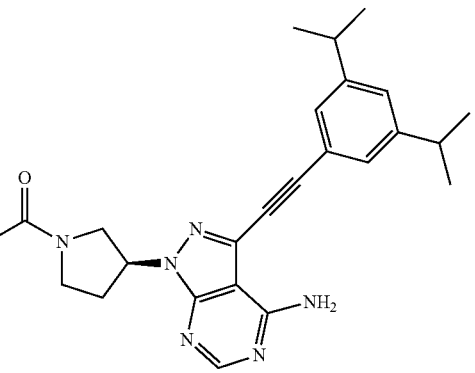 | m/z [M + H]+ 500.3 |
| 5 | 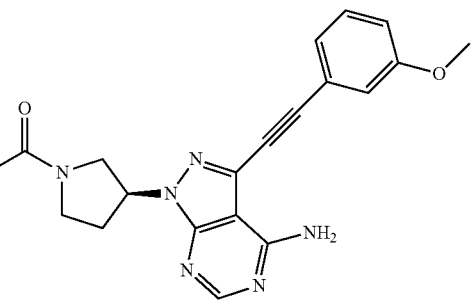 | m/z [M + H]+ 446.2 |
| 6 | 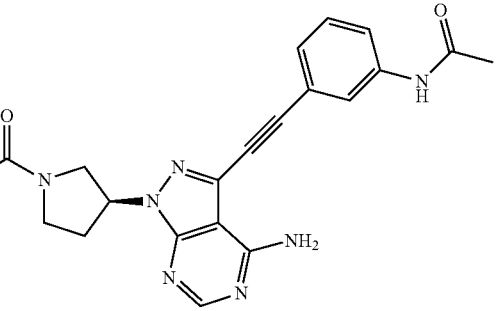 | m/z [M + H]+ 473.2 |

TABLE 20-continued

| Ref. Ex. Comp. | Structural formula | Physical properties |
|---|---|---|
| 7 | [structure] | m/z [M + H]$^+$ 417.2 |

Test Example 1

Measurement of Inhibitory Effect on FGFR2 Kinase Activity

When setting conditions for the measurement of the inhibitory effect of the compounds on FGFR2 kinase activity, FL-Peptide 22 (Caliper Life Sciences, Inc.) was used as a substrate. The purified recombinant human FGFR2 protein used in the test was purchased from Carna Biosciences, Inc. In the measurement of the inhibitory effect of the compounds, first, a test compound was gradually diluted with dimethylsulfoxide (DMSO) to a concentration that was 20 times higher than the final concentration. Next, the purified human FGFR2 protein, FL-Peptide 22 (final concentration: 1.5 μM), magnesium chloride (final concentration: 5 mM), ATP (final concentration: 75 μM), and the test compound DMSO solution (final concentration of DMSO: 5%) were added to a reaction buffer (15 mM Tris-HCl pH 7.5, 0.01% Tween-20, 2 mM DTT), and the mixture was incubated at 25° C. for 120 minutes to perform a kinase reaction. EDTA (final concentration: 30 mM) diluted with a separation buffer (Caliper Life Sciences, Inc.) was added thereto to terminate the kinase reaction. Finally, using a LabChip (registered trademark) 3000 system (Caliper Life Sciences, Inc.; excitation wavelength: 488 nm, detection wavelength: 530 nm), phosphorylated peptides and non-phosphorylated peptides were separated, and the amount of each peptide was measured. The level of phosphorylation was determined from the quantitative ratio. The compound concentration at which phosphorylation was inhibited by 50% was defined as the IC$_{50}$ value (nM). Table 21 shows the results.

The results demonstrated that all of the compounds of the present invention, represented by the test compounds, which had a dialkoxy benzene ethynyl group and a partial structure of α,β-unsaturated amide, exhibited a high FGFR2 inhibitory effect. Conversely, the compounds of the Reference Examples, which did not have a dialkoxy benzene ethynyl group or a partial structure of α,β unsaturated amide, showed a remarkably lower FGFR2 inhibitory effect.

TABLE 21

| Test compound | IC$_{50}$ value (nM) |
|---|---|
| Ex. Compound 1 | 2.4 |
| Ex. Compound 2 | 1.1 |
| Ex. Compound 5 | 1.1 |
| Ex. Compound 8 | 6.9 |
| Ex. Compound 9 | 1.1 |
| Ex. Compound 10 | 1.2 |
| Ex. Compound 12 | 2.2 |
| Ex. Compound 14 | 3.8 |
| Ex. Compound 15 | 3.0 |
| Ex. Compound 16 | 3.8 |
| Ex. Compound 17 | 4.1 |
| Ex. Compound 18 | 4.3 |
| Ex. Compound 19 | 2.7 |
| Ex. Compound 20 | 3.3 |
| Ex. Compound 22 | 5.6 |
| Ex. Compound 23 | 6.8 |
| Ex. Compound 24 | 7.2 |
| Ex. Compound 28 | 3.7 |
| Ex. Compound 29 | 9.3 |
| Ex. Compound 32 | 0.4 |
| Ex. Compound 38 | 4.7 |
| Ex. Compound 39 | 0.4 |
| Ex. Compound 40 | 3.2 |
| Ex. Compound 42 | 6.6 |
| Ex. Compound 46 | 4.3 |
| Ex. Compound 47 | 2.0 |
| Ex. Compound 48 | 6.8 |
| Ex. Compound 49 | 7.0 |
| Ex. Compound 50 | 5.8 |
| Ex. Compound 51 | <0.3 |
| Ex. Compound 52 | 1.0 |
| Ex. Compound 53 | 0.6 |
| Ex. Compound 55 | 2.5 |
| Ex. Compound 56 | 1.5 |
| Ex. Compound 57 | 1.5 |
| Ex. Compound 59 | 1.2 |
| Ex. Compound 60 | 1.5 |
| Ex. Compound 61 | 2.3 |
| Ex. Compound 63 | 1.0 |
| Ex. Compound 64 | 7.9 |
| Ex. Compound 65 | 7.0 |
| Ex. Compound 66 | <0.3 |
| Ex. Compound 68 | 1.2 |
| Ex. Compound 69 | 8.8 |
| Ex. Compound 73 | 4.9 |
| Ref. Ex. Compound 1 | 280 |
| Ref. Ex. Compound 2 | 270 |
| Ref. Ex. Compound 3 | 190 |
| Ref. Ex. Compound 4 | >10000 |
| Ref. Ex. Compound 5 | 190 |
| Ref. Ex. Compound 6 | 110 |
| Ref. Ex. Compound 7 | 1600 |

Test Example 2

Cell Growth-Inhibitory Effect on Human-Derived Gastric Cancer Cell Line with High Expression of FGFR Human-derived gastric cancer OCUM-2MD3 cells, which overexpressed FGFR2, were subcultured daily in a Dulbecco's modified Eagle's medium (DMEM) containing 10% fetal bovine serum (FBS) at a cell density of not more than 80%. In order to initiate a test of the cell growth-inhibitory effect of the compounds, the OCUM-2MD3 cells were suspended in the above DMEM medium and seeded in a 96-well flat-bottom plate so that each well contained 3,000 cells. Then, the cells were cultured in an incubator containing 5% carbon dioxide gas at 37° C. for one day. On the following day, the test compound was gradually diluted with DMSO to a concentration 100 times higher than the final concentration. The DMSO solution of the test compound was diluted with the medium used for cultivation, and the diluted solution was added to each well of the cell culture plate so that the final concentration of DMSO became 0.5%. Then, the cells were cultured in an incubator containing 5% carbon dioxide gas at 37° C. for 72 hours. The number of cells was measured at the time of the addition of the test compound and 72 hours later after culture by using a Cell Counting Kit-8 (produced by Dojindo Laboratories) according to a protocol recommended by Dojindo Laboratories. The reagent of the kit was added to each plate, and a color reaction was performed in an incubator containing 5% carbon dioxide gas at 37° C. for a predetermined time. After completion of the reaction, the absorbance at a wavelength of 450 nm was measured by a microplate reader. The cell-growth inhibition rate was calculated by the following formula, and the concentration of the test compound at which the cell growth was inhibited by 50% ($GI_{50}$ (nM)) was determined. Table 22 shows the results.

The results demonstrated that all of the compounds of the present invention, represented by the test compounds, showed a high growth inhibitory effect on the human-derived gastric cancer OCUM-2MD3 cell line.

Growth inhibition rate (%)=(C-T)/(C-C0)×100

T: absorbance of well to which test compound was added
C: absorbance of well to which test compound was not added
C0: absorbance of well measured before addition of compound

TABLE 22

| Test compound | $GI_{50}$ (nM) |
| --- | --- |
| Ex. Compound 2 | <4.6 |
| Ex. Compound 4 | 17 |
| Ex. Compound 8 | 5 |
| Ex. Compound 12 | <4.6 |
| Ex. Compound 15 | <4.6 |
| Ex. Compound 17 | 4.6 |
| Ex. Compound 19 | <4.6 |
| Ex. Compound 24 | 13 |
| Ex. Compound 25 | 13 |
| Ex. Compound 28 | 5 |
| Ex. Compound 29 | 20 |
| Ex. Compound 32 | <4.6 |
| Ex. Compound 39 | <4.6 |
| Ex. Compound 40 | 7 |
| Ex. Compound 64 | 12 |
| Ex. Compound 65 | 13 |
| Ex. Compound 66 | <4.6 |
| Ex. Compound 68 | 8 |
| Ex. Compound 73 | 7 |

Test Example 3

Measurement of Inhibitory Effect on FGFR1 Kinase Activity

When setting conditions for the measurement of the inhibitory effect of the compounds on FGFR1 kinase activity, a biotinylated peptide (biotin-EEPLYWSFPAKKK) was synthesized for use as a substrate by utilizing the amino acid sequence of FL-Peptide 22 (Caliper Life Sciences, Inc.) with biotin. The purified recombinant human FGFR1 protein used in the test was purchased from Carna Biosciences, Inc. In the measurement of the inhibitory effect of the compounds, first, a test compound was gradually diluted with dimethylsulfoxide (DMSO) to a concentration 20 times higher than the final concentration. Next, the purified human FGFR1 protein, substrate peptide (final concentration: 250 nM), magnesium chloride (final concentration: 5 mM), ATP (final concentration: 190 µM), and the test compound DMSO solution (final concentration of DMSO: 5%) were added to a reaction buffer (15 mM Tris-HCl pH 7.5, 0.01% Tween-20, 2 mM DTT), and the mixture was incubated at 25° C. for 120 minutes to perform a kinase reaction. EDTA was added thereto to a final concentration of 40 mM to thereby terminate the reaction. Then, a detection solution containing Eu-labeled anti-phosphorylated tyrosine antibody PT66 (PerkinElmer) and SureLight APC-SA (PerkinElmer) was added, and the resulting mixture was allowed to stand at room temperature for 2 hours or more. Finally, the intensity of fluorescence when excitation light with a wavelength of 337 nm was irradiated was measured by a PHERAstar FS (BMG LABTECH) at two wavelengths of 620 nm and 665 nm. The amount of phosphorylation was determined from the fluorescence intensity ratio of the two wavelengths. The compound concentration at which phosphorylation was inhibited by 50% was defined as the $IC_{50}$ value (nM). Table 23 below shows the results.

Test Example 4

Measurement of Inhibitory Effect on FGFR3 Kinase Activity

The inhibitory effect of the compounds on FGFR3 kinase activity was measured according to the method of Test Example 3. Purified recombinant human FGFR3 protein was purchased from Carna Biosciences, Inc. The final concentration of ATP was 50 µM. Table 23 shows the results.

Test Example 5

Measurement of Inhibitory Effect on FGFR4 Kinase Activity

The inhibitory effect of the compounds on FGFR4 kinase activity was measured according to the method of Test Example 3. Purified recombinant human FGFR4 protein was purchased from Carna Biosciences, Inc. The final concentration of ATP was 200 µM. Table 23 shows the results.

The results of Test Examples 3 to 5 demonstrated that all of the compounds of the present invention, represented by the test compound, showed a high inhibitory effect on FGFR1, FGFR3, and FGFR4, and served as pan-FGFR inhibitors.

TABLE 23

| Test compound | IC$_{50}$ value (nM) | | |
| --- | --- | --- | --- |
| | Test Example 3 | Test Example 4 | Test Example 5 |
| Ex. Compound 2 | 3.6 | 0.5 | 3.4 |
| Ex. Compound 5 | 1.4 | 0.2 | 0.5 |
| Ex. Compound 9 | 3.2 | 0.3 | 4.9 |
| Ex. Compound 47 | 20 | 0.5 | 11 |
| Ex. Compound 51 | 1.2 | 0.1 | 1.7 |
| Ex. Compound 52 | 2.8 | 0.7 | 21 |
| Ex. Compound 62 | 3.1 | 0.7 | 19 |

Test Example 6

HEK293 cells were established in which a dovitinib-resistant FGFR2 mutant N550H or E566G, or K660M, which is known as a mutation in uterine cancer, was expressed. Further, HEK293 cell lines were also established in which V565I, which is a mutation of the 565th valine at the gatekeeper site to isoleucine, was expressed. These cell lines were incubated with the compound of Example 2 and further with a known FGFR inhibitor AZD4547 or BGJ-398. Then, the effect of inhibiting intracellular FGFR2 phosphorylation and cell growth was examined.

The results of Table 24 revealed that the inhibitory activity of both AZD4547 and BGJ-398 on the dovitinib-resistant FGFR2 mutant N550H or E566G was less than that on wild-type FGFR2. The results demonstrated that the mutants known to be resistant to the FGFR inhibitor dovitinib also exhibited cross resistance to other FGFR inhibitors. It was shown that the inhibitory activity of the compound of Example 2, which is a novel FGFR inhibitor, on these resistant FGFR2 mutants was equivalent to that on the wild type. The inhibitory activity of both AZD4547 and BGJ-398 on the gatekeeper mutant V565I was significantly less than that on the wild type; however, the compound of Example 2 maintained inhibitory activity on this mutant almost equivalent to that on the wild type. These results demonstrated that the compound of Example 2 had inhibitory activity on the mutants resistant to dovitinib, AZD4547, and BGJ-398 equivalent to that on the wild type.

The same experiment was performed on K660M, which is a mutant found in uterine cancer. The results indicated that the inhibitory activity of both AZD4547 and BGJ-398 on this mutant was less than that on the wild type, whereas the inhibitory activity of the compound of Example 2 on this mutant was equivalent to that on the wild type. These results demonstrated that the inhibitory activity of the compound of Example 2 on tumor lines having FGFR mutations refractory to dovitinib, AZD4547, and BGJ-398 was equivalent to that on the wild-type FGFR2.

TABLE 24

| | pFGFR2 inhibition IC$_{50}$ (nM) | | | | |
| --- | --- | --- | --- | --- | --- |
| | FGFR2 wild type | N550H | E566G | K660M | V565I |
| Ex. Compound 2 | 0.9 | 3.6 | 2.4 | 5.2 | 1.3 |
| AZD4547 | 11.1 | >300 | 189.1 | 167.0 | 93.8 |
| BGJ398 | 6.0 | >300 | 33.6 | 118.9 | >3000 |

Test Example 7

Gastric cancer OCUM-2MD3 cells, for which FGFR2 gene amplification had been reported, were cultured for about 3 months in the presence of AZD4547, and cell clones resistant to this drug were isolated. FGFR2 gene was isolated from the resistant clones, and the base sequence of the gene was decoded and compared with that of wild-type FGFR2. Further, the resistant cell lines were incubated with the compound of Example 2. Then, the effect of inhibiting intracellular FGFR2 phosphorylation and cell growth was examined.

Gastric cancer OCUM-2MD3 cells, for which FGFR2 gene amplification had been reported, were cultured for about 3 months in the presence of AZD4547, and a plurality of cell clones resistant to this drug were isolated. When the base sequence of FGFR2 gene of these cell lines was examined, a mutation of the 660th amino acid K to N was observed. These cell lines were incubated with AZD4547, and the inhibition of intracellular FGFR2 phosphorylation was examined. As a result, the inhibition in these cell lines was less than that in wild-type cell lines. Mutations in the FGFR2 gene were considered to be one cause of acquired resistance. When these clones were treated with the compound of Example 2, FGFR2 phosphorylation and growth were inhibited to the same extent as in the wild type (Tables 25 and 26).

TABLE 25

| | pFGFR2 inhibition, IC$_{50}$ (nM) | |
| --- | --- | --- |
| Treatment | Parent cell | AZD4547 resistant cells |
| Ex. Compound 2 | 1.7 | 3.1 (range; 2.4-3.8) |
| AZD4547 | 4.6 | 59.2 (33.0-94.3) |
| BGJ398 | 4.5 | 22.6 (12.7-30.1) |

TABLE 26

| | Cell growth inhibition, IC$_{50}$ (nM) | |
| --- | --- | --- |
| Treatment | Parent cell | AZD4547 resistant cells |
| Ex. Compound 2 | 1.4 | 4.8 (range; 2.0-9.8) |
| AZD4547 | 6.1 | 158.6 (79.2-240.8) |
| BGJ398 | 7.6 | 55.6 (33.9-98.7) |

The invention claimed is:

1. A method for treating a tumor patient comprising administering a 3,5-disubstituted benzene alkynyl compound represented by Formula (I) to a patient in need of such treatment:

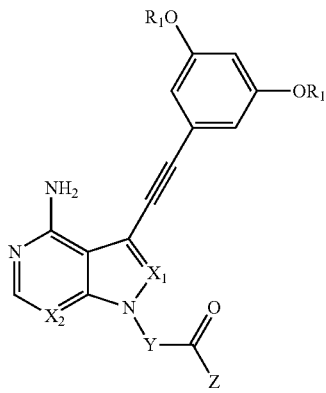

or a salt thereof, wherein $R_1$ is the same or different, and each represents $C_1$-$C_6$ alkyl;

$X_1$ and $X_2$ independently represent N or CH;

Y is a group represented by Formula (A):

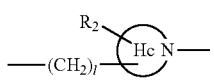

wherein the divalent moiety represented by

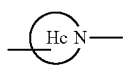

is a nitrogen-containing $C_3$-$C_{10}$ heterocycloalkylene group, a group represented by Formula (B):

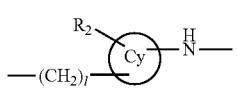

wherein the divalent moiety represented by

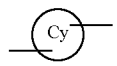

is a $C_3$-$C_{10}$ cycloalkylene group, or a group represented by Formula (C):

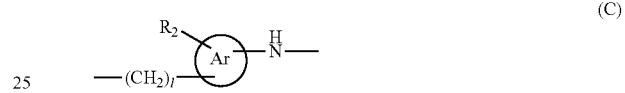

wherein the divalent moiety represented by

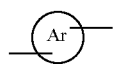

is a $C_6$-$C_{12}$ arylene group;

$R_2$ is hydrogen, $C_2$-$C_6$ alkynyl, —C(=O)$OR_x$, —C(=O)N($R_x$)($R_y$), hydroxy-$C_1$-$C_6$ alkyl, di($C_1$-$C_6$ alkyl)amino-$C_1$-$C_6$ alkyl, or $C_2$-$C_9$ heteroaryl optionally having $R_3$; and $R_3$ is $C_1$-$C_6$ alkyl or di($C_1$-$C_6$ alkyl)amino-$C_1$-$C_6$ alkyl;

Z is —C($R_4$)=C($R_5$)($R_6$) or —C≡C—$R_7$;

$R_4$, $R_5$, and $R_6$ are the same or different, and each represents hydrogen, halogen, $C_1$-$C_6$ alkyl optionally having $R_8$, or a group represented by Formula (D):

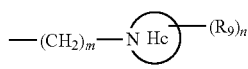

wherein the monovalent moiety represented by

is a nitrogen-containing $C_3$-$C_{10}$ heterocycloalkyl group, $R_7$ is hydrogen, $C_1$-$C_6$ alkyl, or hydroxy-$C_1$-$C_6$ alkyl;

$R_8$ is —$OR_x$ or —N($R_x$)($R_y$);

$R_9$ is $C_1$-$C_6$ alkyl, halogen, or —$OR_x$;

$R_x$ and $R_y$ are the same or different, and each represents hydrogen, $C_1$-$C_6$ alkyl, $C_3$-$C_{10}$ cycloalkyl, di($C_1$-$C_6$ alkyl)amino-$C_1$-$C_6$ alkyl, or $C_1$-$C_6$ alkoxy-$C_1$-$C_6$ alkyl;

l is an integer of 0 to 3;

m is an integer of 1 to 3; and n is an integer of 0 to 2 wherein said tumor patient has a tumor which is resistant to an FGFR inhibitor.

2. The method according to claim 1, wherein the tumor is resistant to at least one FGFR inhibitor selected from the group consisting of ponatinib, regorafenib, intedanib, dovitinib lactate, lenvatinib mesylate, cediranib, oratinib, brivanib alaninate, AZD4547, NVP-BGJ398, sulfatinib, ARQ-087, S-49076, IMCA1, PRO001, and R3Mab.

3. The method according to claim 1, wherein the tumor patient has a mutation at N550 of FGFR2.

4. The method according to claim 1, wherein the tumor patient has a mutation at V565 of FGFR2.

5. The method according to claim 1, wherein the tumor patient has a mutation at E566 of FGFR2.

6. The method according to claim 1, wherein the tumor patient has a mutation at K660 of FGFR2.

7. The method according to claim 1, wherein in Formula (I), (1) when $X_2$ is N, $X_1$ is N or CH, and (2) when $X_2$ is CH, $X_1$ is CH; l is 0 or 1; and (1) when Y is a group represented by Formula (A), the group represented by

is azetidinylene, pyrrolidinylene, piperidinylene, piperazinylene, or morpholinylene, (2) when Y is a group represented by Formula (B), the group represented by

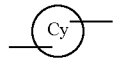

is cyclopropylene or cyclobutylene, and (3) when Y is a group represented by Formula (C), the group represented by

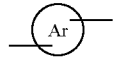

is phenylene.

8. The method according to claim 1, wherein the 3,5-disubstituted benzene alkynyl compound or a salt thereof is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or a salt thereof.

* * * * *

UNITED STATES PATENT AND TRADEMARK OFFICE
CERTIFICATE OF CORRECTION

PATENT NO. : 10,124,003 B2
APPLICATION NO. : 14/905047
DATED : November 13, 2018
INVENTOR(S) : Sootome It is certified that error appears in the above-identified patent and that said Letters Patent is hereby corrected as shown below:

Page 2, Column 1, Line 6, under item (56), Other Publications should read:
NAKATSURU et al., "Significant in vivo Antitumor Activity by a Highly Potent, irreversible FGFR inhibitor, TAS-2985", European Journal of Cancer, 2012, Vol.48, Suppl.6, p.117, 383.

Signed and Sealed this
Twenty-eighth Day of May, 2019

Andrei Iancu
*Director of the United States Patent and Trademark Office*

SEQUENCE LISTING

<160> NUMBER OF SEQ ID NOS: 1

<210> SEQ ID NO 1
<211> LENGTH: 822
<212> TYPE: PRT

-continued

<213> ORGANISM: Homo sapiens

<400> SEQUENCE: 1

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400
```

```
Met Lys Asn Thr Thr Lys Lys Pro Asp Phe Ser Ser Gln Pro Ala Val
            405                 410                 415
His Lys Leu Thr Lys Arg Ile Pro Leu Arg Arg Gln Val Thr Val Ser
            420                 425                 430
Ala Glu Ser Ser Ser Met Asn Ser Asn Thr Pro Leu Val Arg Ile
        435                 440                 445
Thr Thr Arg Leu Ser Ser Thr Ala Asp Thr Pro Met Leu Ala Gly Val
            450                 455                 460
Ser Glu Tyr Glu Leu Pro Glu Asp Pro Lys Trp Glu Phe Pro Arg Asp
465                 470                 475                 480
Lys Leu Thr Leu Gly Lys Pro Leu Gly Glu Gly Cys Phe Gly Gln Val
            485                 490                 495
Val Met Ala Glu Ala Val Gly Ile Asp Lys Asp Lys Pro Lys Glu Ala
            500                 505                 510
Val Thr Val Ala Val Lys Met Leu Lys Asp Asp Ala Thr Glu Lys Asp
            515                 520                 525
Leu Ser Asp Leu Val Ser Glu Met Glu Met Met Lys Met Ile Gly Lys
            530                 535                 540
His Lys Asn Ile Ile Asn Leu Leu Gly Ala Cys Thr Gln Asp Gly Pro
545                 550                 555                 560
Leu Tyr Val Ile Val Glu Tyr Ala Ser Lys Gly Asn Leu Arg Glu Tyr
                565                 570                 575
Leu Arg Ala Arg Arg Pro Pro Gly Met Glu Tyr Ser Tyr Asp Ile Asn
            580                 585                 590
Arg Val Pro Glu Glu Gln Met Thr Phe Lys Asp Leu Val Ser Cys Thr
            595                 600                 605
Tyr Gln Leu Ala Arg Gly Met Glu Tyr Leu Ala Ser Gln Lys Cys Ile
            610                 615                 620
His Arg Asp Leu Ala Ala Arg Asn Val Leu Val Thr Glu Asn Asn Val
625                 630                 635                 640
Met Lys Ile Ala Asp Phe Gly Leu Ala Arg Asp Ile Asn Asn Ile Asp
                645                 650                 655
Tyr Tyr Lys Lys Thr Thr Asn Gly Arg Leu Pro Val Lys Trp Met Ala
                660                 665                 670
Pro Glu Ala Leu Phe Asp Arg Val Tyr Thr His Gln Ser Asp Val Trp
            675                 680                 685
Ser Phe Gly Val Leu Met Trp Glu Ile Phe Thr Leu Gly Gly Ser Pro
            690                 695                 700
Tyr Pro Gly Ile Pro Val Glu Glu Leu Phe Lys Leu Leu Lys Glu Gly
705                 710                 715                 720
His Arg Met Asp Lys Pro Ala Asn Cys Thr Asn Glu Leu Tyr Met Met
                725                 730                 735
Met Arg Asp Cys Trp His Ala Val Pro Ser Gln Arg Pro Thr Phe Lys
                740                 745                 750
Gln Leu Val Glu Asp Leu Asp Arg Ile Leu Thr Leu Thr Thr Asn Glu
            755                 760                 765
Glu Tyr Leu Asp Leu Ser Gln Pro Leu Glu Gln Tyr Ser Pro Ser Tyr
770                 775                 780
```

```
Pro Asp Thr Arg Ser Ser Cys Ser Ser Gly Asp Asp Ser Val Phe Ser
785             790             795             800

Pro Asp Pro Met Pro Tyr Glu Pro Cys Leu Pro Gln Tyr Pro His Ile
            805             810             815

Asn Gly Ser Val Lys Thr
            820
```